US011566057B2

(12) United States Patent
Palani et al.

(10) Patent No.: US 11,566,057 B2
(45) Date of Patent: Jan. 31, 2023

(54) LONG-ACTING CO-AGONISTS OF THE GLUCAGON AND GLP-1 RECEPTORS

(71) Applicant: Merck Sharp & Dohme Corp., Rahway, NJ (US)

(72) Inventors: Anandan Palani, Needham, MA (US); Qiaolin Deng, Edison, NJ (US); Chunhui Huang, Arlington, MA (US); Yuping Zhu, Basking Ridge, NJ (US); Elisabetta Bianchi, Pomezia (IT); Federica Orvieto, Rome (IT)

(73) Assignee: Merck Sharp & Dohme LLC, Rahway, NJ (US)

( * ) Notice: Subject to any disclaimer, the term of this patent is extended or adjusted under 35 U.S.C. 154(b) by 29 days.

(21) Appl. No.: 16/643,881

(22) PCT Filed: Sep. 21, 2018

(86) PCT No.: PCT/US2018/052124
§ 371 (c)(1),
(2) Date: Mar. 3, 2020

(87) PCT Pub. No.: WO2019/060660
PCT Pub. Date: Mar. 28, 2019

(65) Prior Publication Data
US 2020/0270325 A1 Aug. 27, 2020

Related U.S. Application Data

(60) Provisional application No. 62/562,674, filed on Sep. 25, 2017.

(51) Int. Cl.
A61K 38/28 (2006.01)
A61K 38/26 (2006.01)
C07K 14/605 (2006.01)
A61P 3/10 (2006.01)
C07K 14/62 (2006.01)
A61K 38/00 (2006.01)

(52) U.S. Cl.
CPC .............. C07K 14/605 (2013.01); A61P 3/10 (2018.01); C07K 14/62 (2013.01); A61K 38/00 (2013.01)

(58) Field of Classification Search
CPC combination set(s) only.
See application file for complete search history.

(56) References Cited

U.S. PATENT DOCUMENTS

2016/0114000 A1* 4/2016 Bianchi .................. A61K 38/26
530/308

FOREIGN PATENT DOCUMENTS

| KR | 20170073638 A | 6/2017 | | |
|---|---|---|---|---|
| WO | WO2003022304 | 3/2003 | | |
| WO | WO2004062685 A2 | 7/2004 | | |
| WO | WO2006134340 A9 | 12/2006 | | |
| WO | WO2008101017 A2 | 8/2008 | | |
| WO | 2009155258 A2 | 12/2009 | | |
| WO | WO2010096052 A1 | 8/2010 | | |
| WO | 2011075393 A2 | 6/2011 | | |
| WO | 2012177443 A2 | 12/2012 | | |
| WO | 2012177444 A2 | 12/2012 | | |
| WO | 2016065090 A1 | 4/2016 | | |
| WO | WO-2017074798 A2 * | 5/2017 | ............. | A61K 38/28 |
| WO | 2017160669 A1 | 9/2017 | | |

OTHER PUBLICATIONS

Cornier et al., "The metabolic syndrome," Endo. Rev. 29:777-822 (2008) (Year: 2008).*
Metabolic disease, Encyclopedia Britannica, accessed Feb. 12, 2020 at URL: britannica.com/science/metabolic-disease; pp. 1-17 (2019) (Year: 2019).*
Baggio et al., Oxyntomodulin and Glucagon-Like Peptide-1 Differentially, Gastroenterol., 2004, pp. 546-558, 127.
Choudhri et al., Differential hypothalamic neuronal activation following peripheral injection of GLP-1 and oxyntomodulin in mice detected by manganese-enhanced magnetic resonance imaging, Biochem. Biophys. Res. Commun., 2006, pp. 298-306, 350.
Cohen et al., Oxyntomodulin Suppresses Appetite and Reduces Food intake in Humans, J. Clin Endocrinol. Metab., 2003, pp. 4696-4701, 88.
Dakin et al., Oxyntomodulin ameliorates glucose intolerance in mice fed a high-fat diet, Am. J. Physiol. Endocrinol. Metab., 2008, pp. E142-E147, 294.
Dakin et al., Oxyntomodulin Inhibits Food Intake in the Rat, Endocrinology, 2001, pp. 4244-4250, 142.
Dakin et al., Peripheral Oxyntomodulin Reduces Food Intake and Body Weight Gain in Rats, Endocrinology, 2004, pp. 2687-2695, 145.
Dakin et al., Repeated ICV administration of oxyntomodulin causes a greater reduction in body weight gain than in pair-fed rats. Am. J Physiol Endocrinol. Metab., 2002, pp. E1173-E1177, 283.
Day, Jonathan W., A New Glucagon and GLP 1 co agonist eliminates obesity in rodents, Nature Chemical Biology, 2009, No. 10 pp. 749-757, 5.
Drucker et al., Biologic actions and therapeutic potential of the proglucagon-derived peptides, J. Nat. Clin. Pract. Endocrinol. Metab., 2005, pp. 22-31, 1.
Habegger et al., The metabolic actions of glucagon revisited, Nat. Rev. Endocrinol., 2010, pp. 689-697, 6.
Holst, Gut hormones as pharmaceuticals From enteroglucagon to GLP-1 and GLP-2, Regul. Pept., 2000, pp. 15-51, 93.
Jarrouse et al., A Pure Enteroglucagon, Oxyntomodulin (Glucagon 37), Stimulates Insulin Release in Perfused Rat Pancreas, Endocrinol., 1984, pp. 102-105, 115.
Jiang et al., Glucagon and regulation of glucose metabolism, Am. J. Physiol. Endocrinol. Metab., 2003, pp. E671-E678, 284.
Jorgensen et al., Oxyntomodulin Differentially Affects Glucagon-Like Peptide-1 Receptor Beta-Arrestin Recruitment and Signaling through G alpha s, J Pharma. Exp. Therapeut., 2007, pp. 148-154, 322.

(Continued)

Primary Examiner — Julie Ha
Assistant Examiner — Kristina M Hellman
(74) Attorney, Agent, or Firm — Baerbel R. Brown; Catherine D. Fitch

(57) ABSTRACT

Long-acting co-agonists of the glucagon and GLP-1 receptors are described.

24 Claims, No Drawings
Specification includes a Sequence Listing.

(56) References Cited

OTHER PUBLICATIONS

Lykkegaard et al., Regulatory Role of Glucose and Melanocortin 4 Receptor in AMP-Activated Protein Kinase Activity in the Hypothalamus: Association with Feeding Behavior, ADA Scientific Sessions, Abstract No. 1506 P, 2003, Abstract No. 1506P, Abstract No. 1506P.

Pocai et al., Glucagon-Like Peptide 1/Glucagon Receptor Dual Agonism Reverses Obesity in Mice, Diabetes, 2009, pp. 2258-2266, 58.

Salter, Metabolic Effects of Glucagon in the Wistar Rat, Am. J. Clin. Nutr., 1960, pp. 535-539, 8.

Schjoldager et al., Oxyntomodulin: a potential hormone from the distal gut. Pharmacokinetics and effects on gastric acid and insulin secretion in man, Eur. J Clin. Invest., 1988, pp. 499-503, 18.

Sowden et al., Oxyntomodulin increases intrinsic heart rate in mice independent of the glucagon-like peptide-1 receptor, Am. J. Physiol. Regul. Integr. Comp. Physiol., 2007, pp. R962-R970, 292.

Wynne et al., Subcutaneous Oxyntomodulin Reduces Body Weight in Overweight and Obese Subjects, Diabetes, 2005, pp. 2390-2395, 54.

Zhu et al., The Role of Dipeptidyl Peptidase IV in the Cleavage of Glucagon Family Peptides, J. Biol. Chem., 2002, pp. 22418-22423, 278.

Database Geneseq [Online] Jun. 1, 2017 (Jun. 1, 2017), "Human GCGR/ GLP1 R co-agonist peptide TP370, SEQ ID:5 ", XP055841193, retrieved from EBI accession No. GSP:BDV10636, Database accession No. BDV10636, 1 page.

Database Geneseq [Online] Jun. 1, 2017 (Jun. 1, 2017), "Human GCGR/ GLP1 R co-agonist peptide TP575, Seq ID:68 ", XP055841202, retrieved from EBI accession No. GSP:BDV10699, Database accession No. BDV10699, 1 page.

\* cited by examiner

LONG-ACTING CO-AGONISTS OF THE GLUCAGON AND GLP-1 RECEPTORS

CROSS-REFERENCE TO RELATED APPLICATIONS

This application is a U.S. National Phase application under 35 U.S.C. § 371 of PCT Application No. PCT/US2018/052124, filed on Sep. 21, 2018, which claims priority from and the benefit of U.S. Provisional Application No. 62/562,674, filed Sep. 25, 2017.

BACKGROUND OF THE INVENTION

Field of the Invention

The present invention is related to long-acting co-agonist peptides of the glucagon and GLP-1 receptors.

Description of Related Art

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Glucagon is a peptide hormone structurally related to GLP-1 that is well recognized for its acute ability to increase blood glucose through stimulation of glycogenolysis and gluconeogenesis (Jiang & Zhang, Am. J. Physio.l Endocrinol. Metab. 284: E671-E678 (2003)). Of lesser appreciation are the chronic effects of glucagon pharmacology characterized by increases in thermogenesis, satiety, lipolysis, fatty acid oxidation, and ketogenesis (Habegger et al., Nat. Rev. Endocrinol. 6: 689-697 (2010)). Repeated administration of glucagon was first reported decades ago to yield improvements in rodent metabolism, accompanied with lower body weight (Salter, Am. J. Clin. Nutr. 8: 535-539 (1960)). Nonetheless, the inherent risk of hyperglycemia, especially in insulin resistant states such T2DM, has complicated the translation of these observations to human study.

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)). Studies of OXM action in mice have demonstrated that although OXM can activate both the glucagon (GCG) and the GLP-1 receptors, the anorectic actions of OXM require only the GLP-1 receptor, as icv OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through G-alpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma t1/2<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans have been the object of Published International Application Nos. WO03/022304, WO2004/062685, WO2006/134340, and WO2010/096052.

Two independent and simultaneous papers reported the use of relatively balanced GLP-1 receptor/GCG receptor co-agonists as being of enhanced efficacy and safety relative to pure GLP1R agonists in the treatment of rodent obesity, with simultaneous improvement in glycemic control (Day et al., Nat. Chem. Biol. 5: 749-757 (2009); Pocai et a al., Diabetes 58: 2258-2266 (2009)). Of related significance is work with oxyntomodulin (OXM), an endogenous precursor to glucagon, which is secreted postprandially by L-cells of the jejuno-ileum together with GLP-1 (Hoist, Regul. Pept. 93: 45-51 (2000); Drucker, Nat. Clin. Pract. Endocrinol. Metab. 1: 22-31 (2005).

Glucagon peptide analogs and derivatives modified to have various degrees of activity at the GLP-1 receptor and GCG receptor have been disclosed in Published International Application Nos. WO2008/1010017, WO2009/155258, WO2011/075393, WO2012/177444, and WO2012/177443. While some of the disclosed glucagon peptide analogs were reported therein to have activity at both the GLP-1 receptor and GCG receptor; however, there remains a need for co-agonist peptides that have activity or potency at the GLP-1 receptor and GCG receptor and which can be administered less than once daily, e.g. once every second or third day preferably once weekly, while retaining an acceptable clinical profile.

BRIEF SUMMARY OF THE INVENTION

The present invention provides glucagon analogs that display activity at the GLP-1 receptor (GLP-1) and the glucagon (GCG) receptor and that have a long-acting profile comprising a prolonged blood serum half-life. These GCG/GLP-1 receptor co-agonist peptides may have a blood serum half-life of at least one day, two days, three days, four days, five days, six days, or seven days.

The GCG/GLP-1 receptor co-agonist peptides disclosed herein are useful for the treatment of metabolic diseases or disorders. Such metabolic diseases or disorders, include but are not limited to, diabetes (e.g., Type 1 diabetes, Type 2 diabetes, or gestational diabetes), non-alcoholic fatty liver disease (NAFLD), non-alcoholic steatohepatitis (NASH), and obesity. In particular embodiments, the GCG/GLP-1 receptor co-agonist peptides may be useful for the simultaneous treatment of one or more of the aforementioned metabolic disorders.

In one embodiment, the present invention provides a GCG/GLP-1 receptor co-agonist peptide comprising the formula (SEQ ID NO: 105)
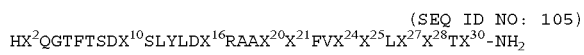
$HX^2QGTFTSDX^{10}SLYLDX^{16}RAAX^{20}X^{21}FVX^{24}X^{25}LX^{27}X^{28}TX^{30}-NH_2$ wherein $X^2$ is alpha-aminoisobutyric acid (aib), D-Ser, or alpha-Methyl-L-Serine (alpha-MS); $X^9$ is Asp or alpha-Methyl-L-Aspartic acid (alpha-MD); $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid.

In another embodiment, the present invention provides a GCG/GLP-1 receptor co-agonist peptide comprising the formula (SEQ ID NO: 123)
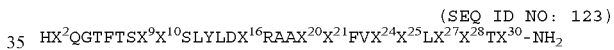
$HX^2QGTFTSX^9X^{10}SLYLDX^{16}RAAX^{20}X^{21}FVX^{24}X^{25}LX^{27}X^{28}TX^{30}-NH_2$ or a pharmaceutically acceptable salt or counterion thereof, wherein $X^2$ is alpha-aminoisobutyric acid (aib), D-Ser, or alpha-Methyl-L-Serine (alpha-MS); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid. In a class of this embodiment, $X^9$ is Asp, or Glu. In another class of this embodiment, $X^9$ is Asp.

In another embodiment, the present invention provides a GCG/GLP-1 receptor co-agonist peptide comprising the formula (SEQ ID NO: 106)
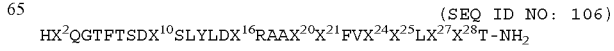
$HX^2QGTFTSDX^{10}SLYLDX^{16}RAAX^{20}X^{21}FVX^{24}X^{25}LX^{27}X^{28}T-NH_2$ wherein $X^2$ is alpha-aminoisobutyric acid (aib), D-Ser, or alpha-Methyl-L-Serine (alpha-MS); $X^9$ is Asp or alpha-Methyl-L-Aspartic acid (alpha-MD); $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; with the proviso that for each co-agonist peptide, only one of $X^{10}$, $X^{20}$, $X^{21}$, $X^{24}$, or $X^{28}$ is conjugated to a fatty diacid.

In another embodiment, the present invention provides a GCG/GLP-1 receptor co-agonist peptide comprising the formula

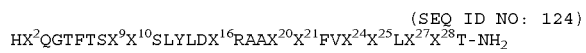
(SEQ ID NO: 124)
$HX^2QGTFTSX^9X^{10}SLYLDX^{16}RAAX^{20}X^{21}FVX^{24}X^{25}LX^{27}X^{28}T-NH_2$ or a pharmaceutically acceptable salt or counterion thereof, wherein
$X^2$ is alpha-aminoisobutyric acid (aib), D-Ser, or alpha-Methyl-L-Serine (alpha-MS); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; with the proviso that for each co-agonist peptide, only one of $X^{10}$, $X^{20}$, $X^{21}$, $X^{24}$, or $X^{28}$ is conjugated to a fatty diacid. In a class of this embodiment, $X^9$ is Asp, or Glu. In another class of this embodiment, $X^9$ is Asp.

In another embodiment, the present invention provides a GCG/GLP-1 receptor co-agonist peptide comprising the formula

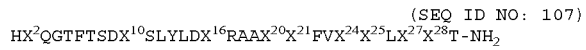
(SEQ ID NO: 107)
$HX^2QGTFTSDX^{10}SLYLDX^{16}RAAX^{20}X^{21}FVX^{24}X^{25}LX^{27}X^{28}T-NH_2$ wherein $X^2$ is alpha-aminoisobutyric acid (aib); $X^9$ is Asp or alpha-Methyl-L-Aspartic acid (alpha-MD); $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid.

In another embodiment, the present invention provides a GCG/GLP-1 receptor co-agonist peptide comprising the formula

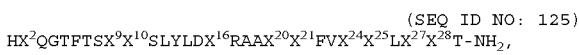
(SEQ ID NO: 125)
$HX^2QGTFTSX^9X^{10}SLYLDX^{16}RAAX^{20}X^{21}FVX^{24}X^{25}LX^{27}X^{28}T-NH_2$, or a pharmaceutically acceptable salt or counterion thereof, wherein
$X^2$ is alpha-aminoisobutyric acid (aib); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid. In a class of this embodiment, $X^9$ is Asp, or Glu. In another class of this embodiment, $X^9$ is Asp.

In particular aspects, the fatty diacid comprises a C14, C15, C16, C17, C18, C19, or C20 fatty diacid. In a further aspect, the fatty diacid comprises a C16 or C18 fatty diacid.

In particular aspects, the GCG/GLP-1 receptor co-agonist peptide comprises the fatty diacid conjugated to the Lys or pAF via a gamma-Glu, gamma-Glu linker.

In particular aspects, the GCG/GLP-1 receptor co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In particular aspects, the GCG/GLP-1 receptor co-agonist peptide comprises at $X^{10}$ a pAF conjugated to a fatty diacid.

In particular aspects, the GCG/GLP-1 receptor co-agonist peptide comprises at $X^{10}$ a Lys conjugated to a C16 fatty acid and a Lys at position 20 or 24 conjugated to a fatty diacid.

In particular aspects, the GCG/GLP-1 receptor co-agonist peptide comprises at $X^{20}$ a pAF conjugated to a fatty diacid or a Lys conjugated to a fatty diacid.

In particular aspects, the GCG/GLP-1 receptor co-agonist peptide comprises at $X^{21}$ a pAF conjugated to a fatty diacid or a Lys conjugated to a fatty diacid.

In particular aspects, the GCG/GLP-1 receptor co-agonist peptide comprises at $X^{24}$ a pAF conjugated to a fatty diacid or a Lys conjugated to a fatty diacid.

In particular aspects, the GCG/GLP-1 receptor co-agonist peptide comprises at $X^{28}$ ta pAF conjugated to a fatty diacid or a Lys conjugated to a fatty diacid.

In a further embodiment, the present invention provides a GCG/GLP-1 receptor co-agonist peptide selected from the group consisting of TP565, TP579, TP583, TP584, TP578, TP580, TP581, TP582, TP588, TP589, TP590, TP592, TP594, TP576, TP577, TP586, TP587, TP591, TP593, TP595, TP596, TP599, TP600, TP601, TP602, TP603, TP605, TP606, TP607, TP610, TP611, TP612, TP613, TP614, TP615, TP616, TP617, TP618, TP619, TP620, TP621, TP622, TP623, TP624, TP625, TP626, TP627, TP629, TP631, TP632, TP633, TP634, TP635, TP636, TP637, TP638, TP639, TP657, TP658, TP659, TP660, TP661, TP662, TP663, TP664, TP665, TP666, TP667, TP672, TP673, TP674, TP675, TP676, TP677, TP678, TP679, TP680, TP681, TP682, TP683, TP685, TP693, TP699, TP700, TP701, TP702, TP703, TP704, TP705, TP712, TP713, TP735, TP736, TP737, TP811, TP812, TP813, TP814, TP815, TP825, TP826, TP827, and TP828. The aforementioned GCG/CLP-1 receptor co-agonist peptides have the structure as shown in Table 1.

The GCG/GLP-1 receptor co-agonist peptide preferably has measurable activity at the glucagon receptor and/or the GLP-1 receptor.

In particular embodiments, the GCG/GLP-1 receptor co-agonist peptide has an EC50 at each of the glucagon and GLP-1 receptors that is less than 5 nM. Examples of such peptides include GCG/GLP-1 receptor co-agonist peptide selected from the group consisting of TP584, TP578, TP580, TP581, TP582, TP588, TP590, TP592, TP594, TP576, TP577, TP586, TP587, TP591, TP593, TP595, TP596, TP599, TP600, TP601, TP602, TP603, TP605, TP606, TP607, TP612, TP614, TP615, TP616, TP617, TP618, TP619, TP620, TP621, TP622, TP623, TP624, TP625, TP626, TP627, TP629, TP631, TP633, TP634, TP635, TP636, TP637, TP638, TP657, TP658, TP659, TP660, TP661, TP662, TP663, TP664, TP665, TP672, TP673, TP674, TP675, TP676, TP677, TP678, TP679, TP680, TP681, TP682, TP683, TP685, TP702, TP704, TP705, TP712, TP713, TP735, TP736, TP737, TP811, TP812, TP813, TP814, TP815, TP825, TP826, TP827, and TP828. In a class of this embodiment, the GCG/GLP-1 receptor co-agonist peptide is selected from a pharmaceutically acceptable salt or counterion of the GCG/GLP-1 receptor co-agonist peptide.

In another embodiment, the present invention provides a GCG/GLP-1 receptor co-agonist peptide comprising the formula (SEQ ID NO: 108)
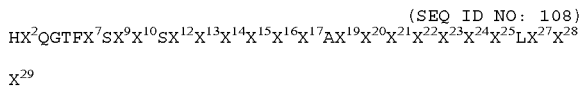

or a pharmaceutically acceptable salt or counterion thereof, wherein $X^2$ is alpha-aminoisobutyric acid (aib), D-Ser, or alpha-Methyl-L-Serine (αMS); $X^7$ is Thr, Phe or Leu; $X^9$ is Asp or Glu; $X^{10}$ is Tyr, norleucine (Nle) conjugated to a fatty acid, p-aminomethyl-L-phenylalanine (pAF) conjugated to a fatty diacid, Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid; $X^{12}$ is Lys, or Glu; $X^{13}$ is Tyr, Leu, or Lys; $X^{14}$ is Leu, or Asp; $X^{15}$ is Asp, Glu, alpha-Methyl-L-Aspartic acid (αMD), or alpha-aminoisobutyric acid (aib); $X^{16}$ is alpha-aminoisobutyric acid (aib), Ala, Glu, Ser, Arg, or Lys; $X^{17}$ is Arg, Lys, Leu, or Ala; $X^{19}$ is Ala, or Gln; $X^{20}$ is Gln, Lys, Lys conjugated to a fatty diacid, p-aminomethyl-L-phenylalanine (pAF) conjugated to a fatty diacid, or norleucine (Nle) conjugated to a fatty diacid; $X^{21}$ is Asp, Phe, Glu, alpha-Methyl-L-Aspartic acid (αMD), Lys conjugated to a fatty diacid, or pAF conjugated to a fatty diacid; $X^{22}$ is Phe, Val, or alpha-methyl-L-phenylalanine (αMF); $X^{23}$ is Val, or Gln; $X^{24}$ is Gln, Glu, Lys conjugated to a fatty diacid, or pAF conjugated to a fatty diacid; $X^{25}$ is Trp, or alpha-methyl-L-tryptophan (αMW); $X^{27}$ is L-methionine sulphone (2), or Leu; $X^{28}$ is Asp, alpha-Methyl-L-Aspartic acid (αMD), alpha-aminoisobutyric acid (aib), Ala, Lys, Gln, Glu, γ-glutamic acid (γE), Lys conjugated to a fatty diacid, or pAF conjugated to a fatty diacid; and $X^{29}$ is Thr-OH, Thr-NH$_2$, or Thr(Lys-γ-glutamic acid)NH$_2$; with the proviso that for each co-agonist peptide, only one or two of $X^{10}$, $X^{20}$, $X^{21}$, $X^{24}$, or $X^{28}$ is conjugated to a fatty diacid.

In a class of this embodiment, with the proviso that for each co-agonist peptide, one of $X^{10}$, $X^{20}$, $X^{21}$, $X^{24}$, or $X^{28}$ is conjugated to a fatty diacid. In another class of this embodiment, with the proviso that for each co-agonist peptide, two of $X^{10}$, $X^{20}$, $X^{21}$, $X^{24}$, or $X^{28}$ are conjugated to a fatty diacid.

In another embodiment, the GCG/GLP-1 receptor co-agonist peptides are selected from the group consisting of TP564, TP565, TP579, TP583, TP584, TP575, TP578, TP580, TP581, TP582, TP585, TP588, TP589, TP590, TP592, TP594, TP576, TP577, TP586, TP587, TP591, TP593, TP595, TP596, TP597, TP598, TP599, TP600, TP601, TP602, TP603, TP604, TP605, TP443, TP606, TP607, TP608, TP609, TP610, TP611, TP612, TP613, TP614, TP615, TP616, TP617, TP618, TP619, TP620, TP621, TP622, TP623, TP624, TP625, TP626, TP627, TP628, TP629, TP630, TP631, TP632, TP633, TP635, TP636, TP637, TP638, TP639, TP640, TP657, TP658, TP659, TP660, TP661, TP662, TP663, TP664, TP665, TP666, TP667, TP672, TP673, TP674, TP675, TP676, TP677, TP678, TP679, TP680, TP681, TP682, TP683, TP685, TP693, TP699, TP700, TP701, TP702, TP703, TP704, TP705, TP712, TP713, TP735, TP736, TP737, TP811, TP812, TP813, TP814, TP815, TP825, TP826, TP827, TP828, TP829, TP830, and TP831, or a pharmaceutically acceptable salt or counterion thereof.

The aforementioned GCG/GLP-1 receptor co-agonist peptide represented by SEQ ID NO: 105, 106, 107, 108, 123, 124, and 125 excludes peptides disclosed in Table 1 of WO2017074798.

The present invention further provides a composition comprising one or more of any one of the aforementioned GCG/GLP-1 receptor co-agonist peptides and a pharmaceutically acceptable carrier and/or pharmaceutically acceptable salt.

The present invention further provides a method for treating a patient for a metabolic disease or disorder comprising administering the patient an effective amount of any one or more of the aforementioned GCG/GLP-1 receptor co-agonist peptides to treat the metabolic disease or disorder in the patient.

The present invention further provides method for treating a patient for a metabolic disease or disorder comprising administering the patient an effective amount of a composition comprising any one or more of the GCG/GLP-1 receptor co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned GCG/GLP-1 receptor co-agonist peptides for the treatment of a metabolic disease or disorder.

The present invention further provides for the use of any one of the aforementioned GCG/GLP-1 receptor co-agonist peptides or compositions for manufacture of a medicament for the treatment of a metabolic disease or disorder.

In particular aspects of the use, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a GCG/GLP-1 receptor co-agonist peptide and administering to the patient or individual an effective amount of a composition comprising an insulin or insulin analog to treat the metabolic disease or disorder in the patient or individual.

In particular aspects, the composition comprising the GCG/GLP-1 receptor co-agonist peptide is administered at a time prior to the time the composition comprising the insulin or insulin analog is administered. In another aspect, the composition comprising the insulin or insulin analog is administered at a time prior to the time the composition comprising the GCG/GLP-1 receptor co-agonist peptide is administered. In a further still aspect, the composition comprising the GCG/GLP-1 receptor co-agonist peptide is administered at the same time as the composition comprising the insulin or insulin analog is administered.

In particular aspects, the insulin analog is insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned GCG/GLP-1 receptor co-agonist peptides; an insulin or insulin analog; and, a pharmaceutically acceptable carrier. In particular aspects, the insulin is human insulin or a human insulin analog such as insulin detemir, insulin glargine (U100 or U300), insulin levemir, insulin glulisine, insulin degludec, or insulin lispro.

The present invention further provides for the use of a composition comprising any one of the aforementioned GCG/GLP-1 receptor co-agonist peptides; an insulin or insulin analog; and, a pharmaceutically acceptable carrier for the treatment of a metabolic disease or disorder.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes. The present invention further provides for the use of a composition comprising any one of the aforementioned co-agonist peptides; an insulin or insulin analog; and, a pharmaceutically acceptable carrier for the manufacture of a medicament for the treatment of a metabolic disease or disorder. In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

In particular aspects, the insulin analog is insulin detemir, insulin glargine (U100 or U300), insulin levemir, insulin glulisine, insulin degludec, or insulin lispro.

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

As used herein, the term "peptide" encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length. The term further includes peptides wherein one or more amino acids is conjugated to a second molecule via a linker.

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:
I. Small aliphatic, nonpolar or slightly polar residues:
Ala, Ser, Thr, Pro, Gly;
II. Polar, negative-charged residues and their amides and esters:
Asp, Asn, Glu, Gln, cysteic acid and homocysteic acid;
III. Polar, positive-charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein, "glucagon potency" or "potency compared to native glucagon" of a molecule refers to the inverse ratio of the $EC_{50}$ of the molecule at the glucagon receptor divided by the $EC_{50}$ of native glucagon at glucagon receptor.

As used herein, "GLP-1 potency" or "potency compared to native GLP-1" of a molecule refers to the inverse ratio of the $EC_{50}$ of the molecule at GLP-1 receptor divided by the $EC_{50}$ of native GLP-1 at GLP-1 receptor.

DETAILED DESCRIPTION OF THE INVENTION

The present invention provides glucagon analogs that display activity at the GLP-1 receptor (GLP-1) and the glucagon (GCG) receptor and that have a long-acting profile comprising a prolonged blood serum half-life. These GCG/GLP-1 receptor co-agonist peptides may have a blood serum half-life of at least one day, two days, three days, four days, five days, six days, or seven days.

The GCG/GLP-1 receptor co-agonist peptides comprise (i) an amino acid substitution at position 2 of the peptide that confers resistance to dipeptidyl peptidase IV (DPPIV) degradation of the peptide, (ii) a lysine (Lys) at position 20, 21, 24, or 28 conjugated to a fatty diacid; or, p-aminomethyl-L-phenylalanine (pAF) at position 10, 20, 21, 24, or 28 conjugated to a fatty diacid; or, Norleucine (Nle) at position 20 conjugated to a fatty diacid, and (iii) one, two, three, four, five, or more amino acid substitutions and/or additions, which may control the relative activity of the GCG/GLP-1 receptor co-agonist peptide at the GLP-1 receptor verses the glucagon receptor or may confer enhanced biophysical stability and/or aqueous solubility to the GCG/GLP-1 co-agonist peptides.

In particular aspects of the invention, (i) GCG/GLP-1 receptor co-agonist peptides are provided that have higher activity at the GCG receptor versus the GLP-1 receptor, (ii) GCG/GLP-1 receptor co-agonist peptides that have approximately equivalent activity at both receptors, and (iii) GCG/GLP-1 receptor co-agonist peptides that have higher activity at the GLP-1 receptor versus the glucagon receptor.

The GCG/GLP-1 receptor co-agonist peptides disclosed herein are useful for the treatment of metabolic diseases or disorders. Such metabolic diseases or disorders, include but are not limited to, diabetes (e.g., Type 1 diabetes, Type 2 diabetes, or gestational diabetes), non-alcoholic fatty liver disease (NAFLD), non-alcoholic steatohepatitis (NASH), and obesity. In particular embodiments, the GCG/GLP-1 receptor co-agonist peptides may be useful for the simultaneous treatment of one or more of the aforementioned metabolic disorders.

In one embodiment, the present invention provides a GCG/GLP-1 receptor co-agonist peptide comprising the formula

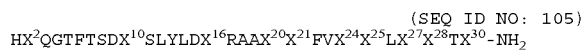
(SEQ ID NO: 105)
$HX^2QGTFTSDX^{10}SLYLDX^{16}RAAX^{20}X^{21}FVX^{24}X^{25}LX^{27}X^{28}TX^{30}\text{-}NH_2$ wherein $X^2$ is alpha-aminoisobutyric acid (aib), D-Ser, or alpha-Methyl-L-Serine (alpha-MS); $X^9$ is Asp or alpha-Methyl-L-Aspartic acid (alpha-MD); $X^{19}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{39}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}, X^{20}, X^{21}, X^{24}$, or $X^{28}$ is conjugated to a fatty diacid.

In another embodiment, the present invention provides a GCG/GLP-1 receptor co-agonist peptide comprising the formula

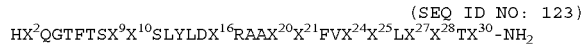
(SEQ ID NO: 123)
$HX^2QGTFTSX^9X^{10}SLYLDX^{16}RAAX^{20}X^{21}FVX^{24}X^{25}LX^{27}X^{28}TX^{30}\text{-}NH_2$ or a pharmaceutically acceptable salt or counterion thereof, wherein
$X^2$ is alpha-aminoisobutyric acid (aib), D-Ser, or alpha-Methyl-L-Serine (alpha-MS); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}, X^{20}, X^{21}, X^{24}$, or $X^{28}$ is conjugated to a fatty diacid. In a class of this embodiment, $X^9$ is Asp, or Glu. In another class of this embodiment, $X^9$ is Asp.

In another embodiment, the present invention provides a GCG/GLP-1 receptor co-agonist peptide comprising the formula

(SEQ ID NO: 106)
$HX^2QGTFTSDX^{10}SLYLDX^{16}RAAX^{20}X^{21}FVX^{24}X^{25}LX^{27}X^{28}T\text{-}NH_2$ wherein $X^2$ is alpha-aminoisobutyric acid (aib), D-Ser, or alpha-Methyl-L-Serine (alpha-MS); $X^9$ is Asp or alpha-Methyl-L-Aspartic acid (alpha-MD); $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; with the proviso that for each co-agonist peptide, only one of $X^{10}, X^{20}, X^{21}, X^{24}$, or $X^{28}$ is conjugated to a fatty diacid.

In another embodiment, the present invention provides a GCG/GLP-1 receptor co-agonist peptide comprising the formula

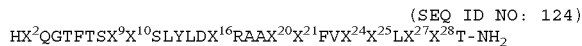
(SEQ ID NO: 124)
$HX^2QGTFTSX^9X^{10}SLYLDX^{16}RAAX^{20}X^{21}FVX^{24}X^{25}LX^{27}X^{28}T\text{-}NH_2$ or a pharmaceutically acceptable salt or counterion thereof, wherein
$X^2$ is alpha-aminoisobutyric acid (aib), D-Ser, or alpha-Methyl-L-Serine (alpha-MS); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; with the proviso that for each co-agonist peptide, only one of $X^{10}, X^{20}, X^{21}, X^{24}$, or $X^{28}$ is conjugated to a fatty diacid. In a class of this embodiment, $X^9$ is Asp, or Glu. In another class of this embodiment, $X^9$ is Asp.

In another embodiment, the present invention provides a GCG/GLP-1 receptor co-agonist peptide comprising the formula

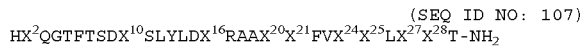
(SEQ ID NO: 107)
$HX^2QGTFTSDX^{10}SLYLDX^{16}RAAX^{20}X^{21}FVX^{24}X^{25}LX^{27}X^{28}T\text{-}NH_2$ wherein $X^2$ is alpha-aminoisobutyric acid (aib); $X^9$ is Asp or alpha-Methyl-L-Aspartic acid (alpha-MD); $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid.

In another embodiment, the present invention provides a GCG/GLP-1 receptor co-agonist peptide comprising the formula

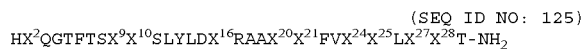
(SEQ ID NO: 125)
$HX^2QGTFTSX^9X^{10}SLYLDX^{16}RAAX^{20}X^{21}FVX^{24}X^{25}LX^{27}X^{28}T-NH_2$ or a pharmaceutically acceptable salt or counterion thereof, wherein
$X^2$ is alpha-aminoisobutyric acid (aib); $X^9$ is Asp, or Glu; $X^{10}$ is Lys or p-aminomethyl-L-phenylalanine (pAF) conjugated to a fatty acid provided that the amino acid at position 20 or 24 is a Lys conjugated to a fatty diacid or Tyr; $X^{16}$ is aib, Ala, Ser, or Glu; $X^{20}$ is Lys is conjugated to a fatty diacid, pAF conjugated to a fatty diacid, norleucine (Nle) conjugated to a fatty diacid, or Gln; $X^{21}$ is Lys conjugated to a fatty diacid or pAF conjugated to a fatty diacid, Asp, alpha-methyl-L-phenylalanine (alpha-MF), or alpha-MD; $X^{24}$ is Gln, Lys conjugated to a fatty diacid, or pAF conjugated to a fatty diacid; $X^{25}$ is Trp or alpha-methyl-L-tryptophan (alpha-MW); $X^{27}$ is L-Met sulphone or Leucine; $X^{28}$ is Glu, Asp or alpha-MD, Lys, aib, or Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone and $X^{28}$ is Ala, aib, alpha-MD, or Lys conjugated to a fatty diacid; with the proviso that for each co-agonist peptide, only one of $X^{10}$, $X^{20}$, $X^{21}$, $X^{24}$, or $X^{28}$ is conjugated to a fatty diacid. In a class of this embodiment, $X^9$ is Asp, or Glu. In another class of this embodiment, $X^9$ is Asp.

In another embodiment, the GCG/GLP-1 receptor co-agonist peptide selected from the group consisting of TP565, TP579, TP583, TP584, TP578, TP580, TP581, TP582, TP588, TP589, TP590, TP592, TP594, TP576, TP577, TP586, TP587, TP591, TP593, TP595, TP596, TP599, TP600, TP601, TP602, TP603, TP605, TP606, TP607, TP610, TP611, TP612, TP613, TP614, TP615, TP616, TP617, TP618, TP619, TP620, TP621, TP622, TP623, TP624, TP625, TP626, TP627, TP629, TP631, TP632, TP633, TP634, TP635, TP636, TP637, TP638, TP639, TP657, TP658, TP659, TP660, TP661, TP662, TP663, TP664, TP665, TP666, TP667, TP672, TP673, TP674, TP675, TP676, TP677, TP678, TP679, TP680, TP681, TP682, TP683, TP685, TP693, TP699, TP700, TP701, TP702, TP703, TP704, TP705, TP712, TP713, TP735, TP736, TP737, TP811, TP812, TP813, TP814, TP815, TP825, TP826, TP827, and TP828, or a pharmaceutically acceptable salt or counterion thereof.

In another embodiment, the GCG/GLP-1 receptor co-agonist peptide selected from the group consisting of TP565, TP579, TP583, TP584, TP578, TP580, TP581, TP582, TP588, TP589, TP590, TP592, TP594, TP576, TP577, TP586, TP587, TP591, TP593, TP595, TP596, TP599, TP600, TP601, TP602, TP603, TP605, TP606, TP607, TP610, TP611, TP612, TP613, TP614, TP615, TP616, TP617, TP618, TP619, TP620, TP621, TP622, TP623, TP624, TP625, TP626, TP627, TP629, TP631, TP632, TP633, TP634, TP635, TP636, TP637, TP638, TP639, TP657, TP658, TP659, TP660, TP661, TP662, TP663, TP664, TP665, TP666, TP667, TP672, TP673, TP674, TP675, TP676, TP677, TP678, TP679, TP680, TP681, TP682, TP683, TP685, TP693, TP700, TP701, TP702, TP704, TP705, TP712, TP713, TP735, TP736, TP737, TP811, TP812, TP813, TP814, TP815, TP825, TP826, TP827, and TP828, or a pharmaceutically acceptable salt or counterion thereof.

In another embodiment, the GCG/GLP-1 receptor co-agonist peptide selected from the group consisting of TP699, and TP703, or a pharmaceutically acceptable salt or counterion thereof.

In another embodiment, the present invention provides a GCG/GLP-1 receptor co-agonist peptide comprising the formula

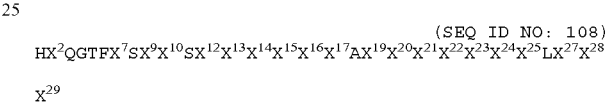
(SEQ ID NO: 108)
$HX^2QGTFX^7SX^9X^{10}SX^{12}X^{13}X^{14}X^{15}X^{16}X^{17}AX^{19}X^{20}X^{21}X^{22}X^{23}X^{24}X^{25}LX^{27}X^{28}X^{29}$ or a pharmaceutically acceptable salt or counterion thereof, wherein $X^2$ is alpha-aminoisobutyric acid (aib), D-Ser, or alpha-Methyl-L-Serine (αMS); $X^7$ is Thr, Phe or Leu; $X^9$ is Asp or Glu; $X^{10}$ is Tyr, norleucine (Nle) conjugated to a fatty acid, p-aminomethyl-L-phenylalanine (pAF) conjugated to a fatty acid, Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid; $X^{12}$ is Lys, or Glu; $X^{13}$ is Tyr, Leu, or Lys; $X^{14}$ is Leu, or Asp; $X^{15}$ is Asp, Glu, alpha-Methyl-L-Aspartic acid (αMD), or alpha-aminoisobutyric acid (aib); $X^{16}$ is alpha-aminoisobutyric acid (aib), Ala, Glu, Ser, Arg, or Lys; $X^{17}$ is Arg, Lys, Leu, or Ala; $X^{19}$ is Ala, or Gln; $X^{20}$ is Gln, Lys, Lys conjugated to a fatty diacid, p-aminomethyl-L-phenylalanine (pAF) conjugated to a fatty diacid, or norleucine (Nle) conjugated to a fatty diacid; $X^{21}$ is Asp, Phe, Glu, alpha-Methyl-L-Aspartic acid (αMD), Lys conjugated to a fatty diacid, or pAF conjugated to a fatty diacid; $X^{22}$ is Phe, Val, or alpha-methyl-L-phenylalanine (αMF); $X^{23}$ is Val, or Gln; $X^{24}$ is Gln, Glu, Lys conjugated to a fatty diacid, or pAF conjugated to a fatty diacid; $X^{25}$ is Trp, or alpha-methyl-L-tryptophan (αMW); $X^{27}$ is L-methionine sulphone (2), or Leu; $X^{28}$ is Asp, alpha-Methyl-L-Aspartic acid (αMD), alpha-aminoisobutyric acid (aib), Ala, Lys, Gln, Glu, γ-glutamic acid (γE), Lys conjugated to a fatty diacid, or pAF conjugated to a fatty diacid; and $X^{29}$ is Thr-OH, Thr-NH$_2$, or Thr(Lys-γ-glutamic acid)NH$_2$; with the proviso that for each co-agonist peptide, only one or two of $X^{10}$, $X^{20}$, $X^{21}$, $X^{24}$, or $X^{28}$ are conjugated to a fatty diacid.

In one embodiment, with the proviso that for each co-agonist peptide, one of $X^{10}$, $X^{20}$, $X^{21}$, $X^{24}$, or $X^{28}$ is conjugated to a fatty diacid. In another embodiment, with the proviso that for each co-agonist peptide, two of $X^{10}$, $X^{20}$, $X^{21}$, $X^{24}$, or $X^{28}$ are conjugated to a fatty diacid.

In another embodiment, $X^2$ is alpha-aminoisobutyric acid (aib), or alpha-Methyl-L-Serine (αMS). In another embodiment, $X^2$ is alpha-aminoisobutyric acid (aib). In another embodiment, $X^2$ is alpha-Methyl-L-Serine (αMS). In another embodiment, $X^2$ is D-Ser.

In another embodiment, $X^7$ is Thr. In another embodiment, $X^7$ is Phe. In another embodiment, $X^7$ is Leu.

In another embodiment, $X^9$ is Asp. In another embodiment, $X^9$ is Glu.

In another embodiment, $X^{10}$ is norleucine (Nle) conjugated to a fatty acid, p-aminomethyl-L-phenylalanine (pAF) conjugated to a fatty diacid, Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid. In another embodiment, $X^{10}$ is norleucine (Nle) conjugated to a fatty acid, p-aminomethyl-L-phenylalanine (pAF) conjugated to a fatty diacid, Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid. In another embodiment, $X^{10}$ is p-aminomethyl-L-phenylalanine (pAF) conjugated to a fatty diacid, Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid. In another embodiment, $X^{10}$ is p-aminomethyl-L-phenylalanine (pAF) conjugated to a fatty diacid. In another embodiment, $X^{10}$ is p-aminomethyl-L-phenylalanine (pAF) conjugated to a fatty acid provided that the amino acid at position 24 is a Lys conjugated to a fatty diacid. In another embodiment, $X^{10}$ is Lys conjugated to a fatty acid provided that the amino acid at position 20 or 24 is a Lys conjugated to a fatty diacid, or p-aminomethyl-L-phenylalanine (pAF) conjugated to a fatty acid provided that the amino acid at position 24 is a Lys conjugated to a fatty diacid. In another embodiment, $X^{10}$ is Tyr.

In another embodiment, $X^{12}$ is Lys. In another embodiment, $X^{12}$ is Glu.

In another embodiment, $X^{13}$ is Tyr, or Leu. In another embodiment, $X^{13}$ is Tyr. In another embodiment, $X^{13}$ is Leu. In another embodiment, $X^{13}$ is Lys.

In another embodiment, $X^{14}$ is Leu. In another embodiment, $X^{14}$ is Asp.

In another embodiment, $X^{15}$ is Asp. In another embodiment, $X^{15}$ is Glu. In another embodiment, $X^{15}$ is □MD. In another embodiment, $X^{15}$ is alpha-aminoisobutyric acid (aib).

In another embodiment, $X^{16}$ is alpha-aminoisobutyric acid (aib), or Ala. In another embodiment, $X^{16}$ is alpha-aminoisobutyric acid (aib). In another embodiment, $X^{16}$ is Ala. In another embodiment, $X^{16}$ is Glu. In another embodiment, $X^{16}$ is Ser. In another embodiment, $X^{16}$ is Arg. In another embodiment, $X^{16}$ is Lys.

In another embodiment, $X^{17}$ is Arg. In another embodiment, $X^{17}$ is Lys. In another embodiment, $X^{17}$ is Leu. In another embodiment, $X^{17}$ is Ala.

In another embodiment, $X^{19}$ is Ala. In another embodiment, $X^{19}$ is Gln.

In another embodiment, $X^{20}$ is Gln, Lys conjugated to a fatty diacid, or norleucine (Nle) conjugated to a fatty diacid. In another embodiment, $X^{20}$ is Gln. In another embodiment, $X^{20}$ is Lys. In another embodiment, $X^{20}$ is pAF conjugated to a fatty diacid. In another embodiment, $X^{20}$ is Lys conjugated to a fatty diacid. In another embodiment, $X^{20}$ is norleucine (Nle) conjugated to a fatty diacid.

In another embodiment, $X^{21}$ is Asp, Glu, Lys conjugated to a fatty diacid, or pAF conjugated to a fatty diacid. In another embodiment, $X^{21}$ is Asp. In another embodiment, $X^{21}$ is Glu. In another embodiment, $X^{21}$ is Phe. In another embodiment, $X^{21}$ is □MD. In another embodiment, $X^{21}$ is Lys conjugated to a fatty diacid. In another embodiment, $X^{21}$ is pAF conjugated to a fatty diacid.

In another embodiment, $X^{22}$ is Phe. In another embodiment, $X^{22}$ is □MF. In another embodiment, $X^{22}$ is Val.

In another embodiment, $X^{23}$ is Val. In another embodiment, $X^{23}$ is Gln.

In another embodiment, $X^{24}$ is Gln. In another embodiment, $X^{24}$ is Lys conjugated to a fatty diacid. In another embodiment, $X^{24}$ is K(PEG$_2$PEG$_2$γEC$_{18}$—OH). In another embodiment, $X^{24}$ is pAF conjugated to a fatty diacid. In another embodiment, $X^{24}$ is Glu.

In another embodiment, $X^{25}$ is Trp. In another embodiment, $X^{25}$ is alpha-methyl-L-tryptophan (αMW).

In another embodiment, $X^{27}$ is L-methionine sulphone (2). In another embodiment, $X^{27}$ is Leu.

In another embodiment, $X^{28}$ is Asp, alpha-Methyl-L-Aspartic acid (αMD), Glu, or pAF conjugated to a fatty diacid. In another embodiment, $X^{28}$ is Asp. In another embodiment, $X^{28}$ is alpha-Methyl-L-Aspartic acid (αMD). In another embodiment, $X^{28}$ is Glu. In another embodiment, $X^{28}$ is pAF conjugated to a fatty diacid.

In another embodiment, $X^{28}$ is alpha-aminoisobutyric acid (aib), Ala, Lys, □-Glu, or Lys conjugated to a fatty diacid. In another embodiment, $X^{28}$ is alpha-aminoisobutyric acid (aib). In another embodiment, $X^{28}$ is Ala. In another embodiment, $X^{28}$ is Lys. In another embodiment, $X^{28}$ is □-Glu. In another embodiment, $X^{28}$ is Lys conjugated to a fatty diacid.

In another embodiment, $X^{29}$ is Thr-OH. In another embodiment, $X^{29}$ is Thr-NH$_2$. In another embodiment, $X^{29}$ is Thr(Lys-γ-glutamic acid)NH$_2$. In another embodiment, $X^{29}$ is Thr-OH, or Thr-NH$_2$. In another embodiment, $X^{29}$ is Thr-OH, or Thr(Lys-γ-glutamic acid)NH$_2$.

In another embodiment, $X^{29}$ is Thr-NH$_2$, or Thr(Lys-γ-glutamic acid)NH$_2$.

In another embodiment, the fatty diacid comprises a C$_{16}$, C$_{18}$, or C$_{20}$ fatty diacid.

In another embodiment, the fatty diacid conjugated to the Lys or pAF via a gamma-Glu linker.

In another embodiment, the fatty diacid conjugated to the Lys or pAF via a gamma-Glu linker, a PEG$_2$ gamma-Glu linker, a PEG$_5$ gamma-Glu linker, a PEG$_2$PEG$_2$-gamma-Glu linker, a PEG$_2$ PEG$_2$PEG$_2$ gamma-Glu linker, wherein PEG$_2$ is 8-amino-3,6-dioxaoctanoic acid, and PEG$_5$ is 1-hydroxy-3,6,9,12,15-pentaoxaoctadecan-18-oic acid.

In another embodiment, the fatty diacid conjugated to the Lys via a PEG$_2$ gamma-Glu linker, a PEG$_5$ gamma-Glu linker, a PEG$_2$PEG$_2$-gamma-Glu linker, a PEG$_2$ PEG$_2$PEG$_2$ gamma-Glu linker, wherein PEG$_2$ is 8-amino-3,6-dioxaoctanoic acid, and PEG$_5$ is 1-hydroxy-3,6,9,12,15-pentaoxaoctadecan-18-oic acid.

In another embodiment, the fatty diacid conjugated to the pAF via a gamma-Glu linker, a PEG$_2$ gamma-Glu linker, a PEG$_2$PEG$_2$-gamma-Glu linker, a PEG$_2$ PEG$_2$PEG$_2$ gamma-Glu linker, wherein PEG$_2$ is 8-amino-3,6-dioxaoctanoic acid, and PEG$_5$ is 1-hydroxy-3,6,9,12,15-pentaoxaoctadecan-18-oic acid.

In another embodiment, the fatty diacid conjugated to the Lys or pAF via a PEG$_5$ gamma-Glu linker, a PEG$_2$PEG$_2$-gamma-Glu linker, or a PEG$_2$ PEG$_2$PEG$_2$ gamma-Glu linker, wherein PEG$_2$ is 8-amino-3,6-dioxaoctanoic acid, and PEG$_5$ is 1-hydroxy-3,6,9,12,15-pentaoxaoctadecan-18-oic acid.

In another embodiment, the fatty diacid conjugated to the Lys via a PEG$_5$ gamma-Glu linker, a PEG$_2$PEG$_2$-gamma-Glu linker, or a PEG$_2$ PEG$_2$PEG$_2$ gamma-Glu linker, wherein PEG$_2$ is 8-amino-3,6-dioxaoctanoic acid, and PEG$_5$ is 1-hydroxy-3,6,9,12,15-pentaoxaoctadecan-18-oic acid.

In another embodiment, the fatty diacid conjugated to the pAF via a PEG$_2$PEG$_2$-gamma-Glu linker, wherein PEG$_2$ is 8-amino-3,6-dioxaoctanoic In another embodiment, the fatty acid comprises a C$_{16}$ fatty acid.

In another embodiment, the fatty acid conjugated to the Lys or pAF via a gamma-Glu-gamma-Glu linker.

In another embodiment, the fatty acid conjugated to the Lys or pAF via a gamma-Glu linker.

In another embodiment, the fatty acid comprises a C$_{18}$ fatty diacid.

In another embodiment, the fatty diacid conjugated to the norleucine (Nle) via a triazole Peg$_2$Peg$_2$-gamma-Glu linker.

In another embodiment, the fatty acid comprises a C$_{15}$, or C$_{16}$ fatty acid.

In another embodiment, the fatty acid conjugated to the norleucine (Nle) via a triazole linker, via a triazole gamma-Glu linker, or via a triazole-C$_4$alkyl-Lys linker.

In another embodiment, with the proviso that for each co-agonist peptide, one or two of X$^{10}$, X$^{20}$, X$^{21}$, X$^{24}$, or X$^{28}$ is conjugated to a fatty diacid and excludes peptides disclosed in Table 1 of WO2017074798.

In another embodiment, with the proviso that for each co-agonist peptide, two of X$^{10}$, X$^{20}$, X$^{21}$, X$^{24}$, or X$^{28}$ is conjugated to a fatty diacid and excludes peptides disclosed in Table 1 of WO2017074798.

In another embodiment, with the proviso that for each co-agonist peptide, only one of X$^{10}$, X$^{20}$, X$^{21}$, X$^{24}$, or X$^{28}$ is conjugated to a fatty diacid and excludes peptides disclosed in Table 1 of WO2017074798.

In another embodiment, the GCG/GLP-1 receptor co-agonist peptide of claim 1, wherein the GCG/GLP-1 receptor co-agonist peptide is selected from the group consisting of TP564, TP565, TP579, TP583, TP584, TP575, TP578, TP580, TP581, TP582, TP585, TP588, TP589, TP590, TP592, TP594, TP576, TP577, TP586, TP587, TP591, TP593, TP595, TP596, TP597, TP598, TP599, TP600, TP601, TP602, TP603, TP604, TP605, TP443, TP606, TP607, TP608, TP609, TP610, TP611, TP612, TP613, TP614, TP615, TP616, TP617, TP618, TP619, TP620, TP621, TP622, TP623, TP624, TP625, TP626, TP627, TP628, TP629, TP630, TP631, TP632, TP633, TP635, TP636, TP637, TP638, TP639, TP640, TP657, TP658, TP659, TP660, TP661, TP662, TP663, TP664, TP665, TP666, TP667, TP672, TP673, TP674, TP675, TP676, TP677, TP678, TP679, TP680, TP681, TP682, TP683, TP685, TP693, TP699, TP700, TP701, TP702, TP703, TP704, TP705, TP712, TP713, TP735, TP736, TP737, TP811, TP812, TP813, TP814, TP815, TP825, TP826, TP827, TP828, TP829, TP830, and TP831, or a pharmaceutically acceptable salt or counterion thereof.

In another embodiment, the GCG/GLP-1 receptor co-agonist peptide selected from the group consisting of TP699, and TP703, or a pharmaceutically acceptable salt or counterion thereof.

In another embodiment, the GCG/GLP-1 receptor co-agonist peptide of claim 1, wherein the GCG/GLP-1 receptor co-agonist peptide is selected from the group consisting of TP575, TP597, TP604, TP608, TP609, TP615, TP617, TP630, TP640, TP672, TP676, TP680, TP704, TP712, and TP813, or a pharmaceutically acceptable salt or counterion thereof.

In another embodiment, the GCG/GLP-1 receptor co-agonist peptide of claim 1, wherein the GCG/GLP-1 receptor co-agonist peptide is TP575, or a pharmaceutically acceptable salt or counterion thereof. In another embodiment, the GCG/GLP-1 receptor co-agonist peptide of claim 1, wherein the GCG/GLP-1 receptor co-agonist peptide is TP597, or a pharmaceutically acceptable salt or counterion thereof. In another embodiment, the GCG/GLP-1 receptor co-agonist peptide of claim 1, wherein the GCG/GLP-1 receptor co-agonist peptide is TP604, or a pharmaceutically acceptable salt or counterion thereof. In another embodiment, the GCG/GLP-1 receptor co-agonist peptide of claim 1, wherein the GCG/GLP-1 receptor co-agonist peptide is TP608, or a pharmaceutically acceptable salt or counterion thereof. In another embodiment, the GCG/GLP-1 receptor co-agonist peptide of claim 1, wherein the GCG/GLP-1 receptor co-agonist peptide is TP609, or a pharmaceutically acceptable salt or counterion thereof. In another embodiment, the GCG/GLP-1 receptor co-agonist peptide of claim 1, wherein the GCG/GLP-1 receptor co-agonist peptide is TP615, or a pharmaceutically acceptable salt or counterion thereof. In another embodiment, the GCG/GLP-1 receptor co-agonist peptide of claim 1, wherein the GCG/GLP-1 receptor co-agonist peptide is TP617, or a pharmaceutically acceptable salt or counterion thereof. In another embodiment, the GCG/GLP-1 receptor co-agonist peptide of claim 1, wherein the GCG/GLP-1 receptor co-agonist peptide is TP630, or a pharmaceutically acceptable salt or counterion thereof. In another embodiment, the GCG/GLP-1 receptor co-agonist peptide of claim 1, wherein the GCG/GLP-1 receptor co-agonist peptide is TP640, or a pharmaceutically acceptable salt or counterion thereof. In another embodiment, the GCG/GLP-1 receptor co-agonist peptide of claim 1, wherein the GCG/GLP-1 receptor co-agonist peptide is TP672, or a pharmaceutically acceptable salt or counterion thereof. In another embodiment, the GCG/GLP-1 receptor co-agonist peptide of claim 1, wherein the GCG/GLP-1 receptor co-agonist peptide is TP676, or a pharmaceutically acceptable salt or counterion thereof. In another embodiment, the GCG/GLP-1 receptor co-agonist peptide of claim 1, wherein the GCG/GLP-1 receptor co-agonist peptide is TP680, or a pharmaceutically acceptable salt or counterion thereof. In another embodiment, the GCG/GLP-1 receptor co-agonist peptide of claim 1, wherein the GCG/GLP-1 receptor co-agonist peptide is TP704, or a pharmaceutically acceptable salt or counterion thereof. In another embodiment, the GCG/GLP-1 receptor co-agonist peptide of claim 1, wherein the GCG/GLP-1 receptor co-agonist peptide is TP712, or a pharmaceutically acceptable salt or counterion thereof. In another embodiment, the GCG/GLP-1 receptor co-agonist peptide of claim 1, wherein the GCG/GLP-1 receptor co-agonist peptide is TP813, or a pharmaceutically acceptable salt or counterion thereof.

The aforementioned GCG/GLP-1 receptor co-agonist peptide represented by SEQ ID NO: 105, 106, 107, 108, 123, 124 and 125 excludes peptides disclosed in Table 1 of WO2017074798.

In particular aspects, the fatty diacid comprises a C14, C15, C16, C17, C18, C19, or C20 fatty diacid. In a further aspect, the fatty diacid comprises a C16 or C18 fatty diacid.

In particular aspects, the GCG/GLP-1 receptor co-agonist peptide comprises the fatty diacid conjugated to the Lys or pAF via a gamma-Glu, gamma-Glu linker.

In particular aspects, the GCG/GLP-1 receptor co-agonist peptide comprises the fatty diacid conjugated to the Lys or pAF via a PEG$_2$PEG$_2$-gamma-Glu linker wherein PEG$_2$ is 8-amino-3,6-dioxaoctanoic acid.

In particular aspects, the GCG/GLP-1 receptor co-agonist peptide comprises at X$^{10}$ a pAF conjugated to a fatty diacid.

In particular aspects, the GCG/GLP-1 receptor co-agonist peptide comprises at $X^{10}$ a Lys conjugated to a C16 fatty acid and a Lys at position 20 or 24 conjugated to a fatty diacid.

In particular aspects, the GCG/GLP-1 receptor co-agonist peptide comprises at $X^{20}$ a pAF conjugated to a fatty diacid or a Lys conjugated to a fatty diacid.

In particular aspects, the GCG/GLP-1 receptor co-agonist peptide comprises at $X^{21}$ a pAF conjugated to a fatty diacid or a Lys conjugated to a fatty diacid.

In particular aspects, the GCG/GLP-1 receptor co-agonist peptide comprises at $X^{24}$ a pAF conjugated to a fatty diacid or a Lys conjugated to a fatty diacid.

In particular aspects, the GCG/GLP-1 receptor co-agonist peptide comprises at $X^{28}$ a pAF conjugated to a fatty diacid or a Lys conjugated to a fatty diacid.

Exemplary GCG/GLP-1 receptor co-agonist peptides within the scope of the invention are disclosed in Table 1.

TABLE 1

| SEQ ID NO: | ID | SEQUENCE |
|---|---|---|
| 1 | TP565 | HUQGTFTSDYSKYLDARAAK(PEG$_2$PEG$_2$γEC$_{20}$-OH)DFVQWL$_2$αMDT-NH$_2$ |
| 2 | TP579 | HsQGTFTSDYSKYLEURAAK(PEG$_2$PEG$_2$γEC$_{20}$-OH)DFVQWLLUTKγE-NH$_2$ |
| 3 | TP583 | HUQGTFTSDYSKYLDARAAQDFVpAF(PEG$_2$PEG$_2$γEC$_{18}$-OH)WLLDT-NH$_2$ |
| 4 | TP584 | HUQGTFTSDYSKYLDARAAQDFVpAF(PEG$_2$PEG$_2$γEC$_{20}$-OH)WLLDT-NH$_2$ |
| 5 | TP578 | HsQGTFTSDYSKYLDURAAK(PEG$_2$PEG$_2$γEC$_{20}$-OH)DFVQWL2DT-NH$_2$ |
| 6 | TP580 | HUQGTFTSDpAF(PEG$_2$PEG$_2$γEC$_{20}$-OH)SKYLDARAAQDFVQWL2DT-NH$_2$ |
| 7 | TP581 | HUQGTFTSDpAF(PEG$_2$PEG$_2$γEC$_{20}$-OH)SKYLDURAAQDFVQWLLATKγE-NH$_2$ |
| 8 | TP582 | HUQGTFTSDpAF(PEG$_2$PEG$_2$γEC$_{20}$-OH)SKYLDURAAQDFVQWLLATKγE-NH$_2$ |
| 9 | TP585 | HUQGTFTSDYSKYLDARAAQpAF(PEG$_2$PEG$_2$γEC$_{20}$-OH)FVQWLLDT-NH$_2$ |
| 10 | TP588 | HUQGTFTSDYSKYLDURAAK(PEG$_2$PEG$_2$γEC$_{20}$-OH)DFVQWL2αMDT-NH$_2$ |
| 11 | TP589 | HUQGTFTSDYSKYLDERAAK(PEG$_2$PEG$_2$γEC$_{20}$-OH)DFVQWL2αMDT-NH$_2$ |
| 12 | TP590 | HUQGTFTSDYSKYLDARAAK(PEG$_2$PEG$_2$γEC$_{20}$-OH)DαMFVQWL2DT-NH$_2$ |
| 13 | TP592 | HαMSQGTFTSDYSKYLDURAAK(PEG$_2$PEG$_2$γEC$_{20}$-OH)DFVQWL2DT-NH$_2$ |
| 14 | TP594 | HUQGTFTSDYSKYLDARAAK(PEG$_2$PEG$_2$γEC$_{20}$-OH)αMDFVQWL2DT-NH$_2$ |
| 15 | TP576 | HUQGTFTSDYSKYLDURAAQDFVK(PEG$_2$PEG$_2$γEC$_{20}$-OH)WL2DT-NH$_2$ |
| 16 | TP577 | HUQGTFTSDYSKYLDSRAAK(PEG$_2$PEG$_2$γEC$_{20}$-OH)DFVQWL2DT-NH$_2$ |
| 17 | TP586 | HUQGTFTSDYSKYLDERAApAF(PEG$_2$PEG$_2$γEC$_{20}$-OH)DFVQWLLKT-NH$_2$ |
| 18 | TP587 | HUQGTFTSDYSKYLDERAApAF(PEG$_2$PEG$_2$γEC$_{18}$-OH)DFVQWLLKT-NH$_2$ |
| 19 | TP591 | HUQGTFTSDYSKYLDARAAK(PEG$_2$PEG$_2$γEC$_{18}$-OH)DαMFVQWL2DT-NH$_2$ |
| 20 | TP593 | HαMSQGTFTSDYSKYLDURAAK(PEG$_2$PEG$_2$γEC$_{20}$-OH)DFVQWL2DT-NH$_2$ |
| 21 | TP595 | HUQGTFFSDYSKYLDARAAK(PEG$_2$PEG$_2$γEC$_{18}$-OH)DFVQWL2DT-NH$_2$ |
| 22 | TP596 | HUQGTFLSDYSKYLDARAAK(PEG$_2$PEG$_2$γEC$_{18}$-OH)DFVQWL2DT-NH$_2$ |
| 23 | TP599 | HUQGTFTSDYSKYLDALAAK(PEG$_2$PEG$_2$γEC$_{18}$-OH)DFVQWL2DT-NH$_2$ |
| 24 | TP600 | HUQGTFTSDYSKYLDARAAK(PEG$_2$PEG$_2$γEC$_{18}$-OH)DFVQWL2QT-NH$_2$ |
| 25 | TP601 | HUQGTFTSDK(γEγEC16)SKYLDARAAK(PEG$_2$PEG$_2$γEC$_{18}$-OH)DFVQWL2DT-NH$_2$ |
| 26 | TP602 | HUQGTFTSDYSKYLDARAAQDFVQWL2K(PEG$_2$PEG$_2$γEC$_{18}$-OH)T-NH$_2$ |
| 27 | TP603 | HUQGTFTSDYSKYLDARAAQDFVQWL2K(PEG$_2$PEG$_2$γEC$_{20}$-OH)T-NH$_2$ |
| 28 | TP605 | HUQGTFTSDYSKYLDARAAQDFVQWL2pAF(PEG$_2$PEG$_2$γEC$_{20}$-OH)T-NH$_2$ |
| 29 | TP606 | HUQGTFTSDK(γEγEC16)SKYLDARAAK(PEG$_2$PEG$_2$γEC$_{16}$-OH)DFVQWL2DT-NH$_2$ |
| 30 | TP607 | HUQGTFTSDK(γEγEC16)SKYLDARAAQDFVK(PEG$_2$PEG$_2$γEC$_{16}$-OH)WL2αMDT-NH$_2$ |
| 31 | TP610 | HUQGTFTSDYSKYLαMDARAAK(PEG$_2$PEG$_2$γEC$_{18}$-OH)DFVQWL2αMDT-NH$_2$ |
| 32 | TP611 | HUQGTFTSDYSKYLDARAAK(PEG$_2$PEG$_2$γEC$_{18}$-OH)αMDFVQWL2αMDT-NH$_2$ |

TABLE 1-continued

| SEQ ID NO: | ID | SEQUENCE |
|---|---|---|
| 33 | TP612 | HUQGTFTSDYSKYLαMDARAAK(PEG$_2$PEG$_2$γEC$_{18}$-OH)αMDFVQWL2αMDT-NH$_2$ |
| 34 | TP613 | HUQGTFTSDYSKYLDERAAK(PEG$_2$PEG$_2$γEC$_{18}$-OH)DFVQWL2αMDT-NH$_2$ |
| 35 | TP614 | HαMSQGTFTSDYSKYLDARAAK(PEG$_2$PEG$_2$γEC$_{16}$-OH)-OH)DFVQWL2αMDT-NH$_2$ |
| 36 | TP615 | HαMSQGTFTSDYSKYLDARAAQK(PEG$_2$PEG$_2$γEC$_{16}$-OH)FVQWL2αMDT-NH$_2$ |
| 37 | TP616 | HαMSQGTFTSDYSKYLDARAAK(PEG$_2$PEG$_2$γEC$_{18}$-OH)DFVQWL2αMDT-NH$_2$ |
| 38 | TP617 | HαMSQGTFTSDYSKYLDARAAQK(PEG$_2$PEG$_2$γEC$_{18}$-OH)FVQWL2αMDT-NH$_2$ |
| 39 | TP618 | HαMSQGTFTSDYSKYLDURAAK(PEG$_2$PEG$_2$γEC$_{16}$-OH)DFVQWL2αMDT-NH$_2$ |
| 40 | TP619 | HαMSQGTFTSDYSKYLDURAAQK(PEG$_2$PEG$_2$γEC$_{16}$-OH)FVQWL2αMDT-NH$_2$ |
| 41 | TP620 | HαMSQGTFTSDYSKYLDURAAK(PEG$_2$PEG$_2$γEC$_{18}$-OH)DFVQWL2αMDT-NH$_2$ |
| 42 | TP621 | HαMSQGTFTSDYSKYLDURAAQK(PEG$_2$PEG$_2$γEC$_{18}$-OH)FVQWL2αMDT-NH$_2$ |
| 43 | TP622 | HUQGTFTSDpAF(PEG$_2$γEC$_{16}$-OH)SKYLDARAAQDFVQWL2DT-NH$_2$ |
| 44 | TP623 | HUQGTFTSDpAF(PEG$_2$γEC$_{18}$-OH)SKYLDARAAQDFVQWL2DT-NH$_2$ |
| 45 | TP624 | HUQGTFTSDpAF(PEG$_2$PEG$_2$γEC$_{18}$-OH)SKYLDARAAQDFVQWL2αMDT-NH$_2$ |
| 46 | TP625 | HUQGTFTSDpAF(PEG$_2$PEG$_2$γEC$_{18}$-OH)SKYLDARAAQDFVQαMWL2DT-NH$_2$ |
| 47 | TP626 | HUQGTFTSDYSKYLDARAAK(PEG$_2$γEC$_{18}$-OH)DFVQWL2DT-NH$_2$ |
| 48 | TP627 | HUQGTFTSDYSKYLDARAAK(PEG$_2$γEC$_{16}$-OH)DFVQWL2αMDT-NH$_2$ |
| 49 | TP629 | HUQGTFTSDYSKYLDARAAK(PEG$_2$γEC$_{20}$-OH)DFVQWL2αMDT-NH$_2$ |
| 50 | TP631 | HUQGTFTSDYSKYLDARAAK(PEG$_2$PEG$_2$γEC$_{18}$-OH)DFVQαMWL2DT-NH$_2$ |
| 51 | TP632 | HUQGTFTSDYSKYLDARAAK(PEG$_2$PEG$_2$γEC$_{18}$-OH)DFVQαMWL2αMDT-NH$_2$ |
| 52 | TP633 | HUQGTFTSDYSKYLDARAAQpAF(PEG$_2$γEC$_{18}$-OH)FVQWLLDT-NH$_2$ |
| 53 | TP634 | HUQGTFTSDYSKYLDARAAQpAF(PEG$_2$PEG$_2$γEC$_{18}$-OH)FVQWL2αMDT-NH$_2$ |
| 54 | TP635 | HUQGTFTSDYSKYLDARAApAF(PEG$_2$γEC$_{18}$-OH)DFVQWLLDT-NH$_2$ |
| 55 | TP636 | HUQGTFTSDYSKYLDARAApAF(PEG$_2$PEG2γEC$_{18}$-OH)DFVQWL2αMDT-NH$_2$ |
| 56 | TP637 | HUQGTFTSDYSKYLDARAAQDFVK(PEG$_2$γEC$_{18}$-OH)WL2DT-NH$_2$ |
| 57 | TP638 | HUQGTFTSDYSKYLDARAAQDFVpAF(PEG$_2$γEC$_{18}$-OH)WLLDT-NH$_2$ |
| 58 | TP639 | HUQGTFTSDYSKYLDARAAQDFVpAF(γEC$_{18}$-OH)WLLDT-NH$_2$ |
| 59 | TP657 | HUQGTFTSDpAF(PEG$_2$PEG$_2$γEC$_{16}$-OH)SKYLDURAAQDFVQWLLαMDTKγE-NH$_2$ |
| 60 | TP658 | HUQGTFTSDpAF(PEG$_2$PEG$_2$γEC$_{16}$-OH)SKYLDURAAQDFVQWL2ATKγE-NH$_2$ |
| 61 | TP659 | HsQGTFTSDpAF(PEG2PEG$_2$γEC16OH)SKYLDURAAQDFVQWLLATKγE-NH$_2$ |
| 62 | TP660 | HαMSQGTFTSDpAF(PEG$_2$PEG$_2$γEC$_{16}$-OH)SKYLDURAAQDFVQWLLATKγE-NH$_2$ |
| 63 | TP661 | HαMsQGTFTSDpAF(PEG$_2$PEG$_2$γEC$_{16}$-OH)SKYLDURAAQDFVQWLLATKγE-NH$_2$ |
| 64 | TP662 | HUQGTFTSDYSKYLDURAAK(PEG$_2$PEG$_2$γEC$_{16}$-OH)DFVQWLLATKγE-NH$_2$ |
| 65 | TP663 | HUQGTFTSDYSKYLDURAApAF(PEG$_2$PEG$_2$γEC$_{16}$-OH)DFVQWLLATKγE-NH$_2$ |
| 66 | TP664 | HUQGTFTSDYSKYLDURAAQK(PEG$_2$PEG$_2$γEC$_{16}$-OH)FVQWLLATKγE-NH$_2$ |
| 67 | TP665 | HUQGTFTSDYSKYLDURAAQpAF(PEG$_2$PEG$_2$γEC$_{16}$-OH)FVQWLLATKγE-NH$_2$ |
| 68 | TP666 | HUQGTFTSDYSKYLDURAAQFVQK(PEG$_2$PEG$_2$γEC$_{16}$-OH)WLLATKγE-NH$_2$ |
| 69 | TP667 | HUQGTFTSDYSKYLDURAAQFVQpAF(PEG$_2$PEG$_2$γEC$_{16}$-OH)WLLATKγE-NH$_2$ |
| 70 | TP672 | HUQGTFTSDYSKYLDARAAK(PEG$_2$PEG$_2$γEC$_{18}$-OH)DFVQWL2ET-NH$_2$ |
| 71 | TP673 | HUQGTFTSDYSKYLDURAAK(PEG$_2$PEG$_2$γEC$_{18}$-OH)DFVQWL2ET-NH$_2$ |

TABLE 1-continued

| SEQ ID NO: | ID | SEQUENCE |
|---|---|---|
| 72 | TP674 | HUQGTFTSDYSKYLEARAAK(PEG$_2$PEG$_2$γEC$_{18}$-OH)DFVQWL2DT-NH$_2$ |
| 73 | TP675 | HUQGTFTSDYSKYLDURAAQDFVK(PEG$_2$PEG$_2$γEC$_{18}$-OH)WL2ET-NH$_2$ |
| 74 | TP676 | HUQGTFTSDYSKYLDARAAK(PEG$_2$PEG$_2$PEG$_2$γEC$_{18}$-OH)DFVQWL2DT-NH$_2$ |
| 75 | TP677 | HUQGTFTSDYSKYLDARAAK(PEG$_2$PEG$_2$PEG$_2$γEC$_{18}$-OH)DFVQWL2αMDT-NH$_2$ |
| 76 | TP678 | HUQGTFTSDYSKYLDARAApAF(PEG$_2$PEG$_2$PEG$_2$γEC$_{18}$-OH)DFVQWLLDT-NH$_2$ |
| 77 | TP679 | HUQGTFTSDYSKYLDARAAQpAF(PEG$_2$PEG$_2$PEG$_2$γEC$_{18}$-OH)FVQWLLDT-NH$_2$ |
| 78 | TP680 | HUQGTFTSDYSKYLDARAAQDFVK(PEG$_2$PEG$_2$PEG$_2$γEC$_{18}$-OH)WL2DT-NH$_2$ |
| 79 | TP681 | HUQGTFTSDYSKYLDARAAQK(PEG$_2$PEG$_2$γEC$_{18}$-OH)FVQWL2αMDT-NH$_2$ |
| 80 | TP682 | HUQGTFTSDYSKYLDURAAQDFVQWLLpAF(PEG$_2$PEG$_2$γEC$_{18}$-OH)TKγE-NH$_2$ |
| 81 | TP683 | HUQGTFTSDYSKYLDURAAQDFVQWLLK(PEG$_2$PEG$_2$γEC$_{18}$-OH)TKγE-NH$_2$ |
| 82 | TP685 | HsQGTFTSDYSKYLDURAAQDFVQWLLK(PEG$_2$PEG$_2$γEC$_{18}$-OH)TKγE-NH$_2$ |
| 83 | TP693 | HsQGTFTSDpAF(γEγEC16)SKYLDARAAQDFVK(PEG2PEG2γEC16-OH)WL2DT-NH$_2$ |
| 84 | TP699 | HUQGTFTSEYSKKLDARAAQDFVK(PEG$_2$PEG$_2$γEC$_{18}$-OH)WL2DT-NH$_2$ |
| 85 | TP700 | HUQGTFTSDYSEYLDKRAAQDFVK(PEG$_2$PEG$_2$γEC$_{18}$-OH)WL2DT-NH$_2$ |
| 86 | TP701 | HUQGTFTSDYSKYLDERAAKDFVK(PEG$_2$PEG$_2$γEC$_{18}$-OH)WL2DT-NH$_2$ |
| 87 | TP702 | HUQGTFTSDYSKYLDARAAQEFVK(PEG$_2$PEG$_2$γEC$_{18}$-OH)WL2DT-NH$_2$ |
| 88 | TP703 | HUQGTFTSEYSKKLDARAAK(PEG$_2$PEG$_2$γEC$_{18}$-OH)DFVQWL2DT-NH$_2$ |
| 89 | TP704 | HUQGTFTSDYSKYLDARAAK(PEG$_2$PEG$_2$γEC$_{18}$-OH)EFVQWL2DT-NH$_2$ |
| 90 | TP705 | HUQGTFTSDYSKYLDARAAK(PEG$_2$PEG$_2$γEC$_{18}$-OH)DFVEWL2KT-NH$_2$ |
| 91 | TP712 | HUQGTFTSDYSKYLDARAANle(1,2,3-triazole-5-PEG$_2$PEG$_2$γEC$_{18}$-OH)-DFVQWL2DT-NH$_2$ |
| 92 | TP713 | HUQGTFTSDYSKYLDARAAK(PEG$_2$PEG$_2$γEC$_{18}$-OH)EFVQWL2αMDT-NH$_2$ |
| 93 | TP735 | HUQGTFTSDYSKYLDARAAK(PEG$_2$PEG$_2$γEC$_{18}$-OH)DFVQWL2αMDT-OH |
| 94 | TP736 | HUQGTFTSDYSKYLDARAAK(PEG$_2$PEG$_2$γEC$_{18}$-OH)DFVQWL2DT-OH |
| 95 | TP737 | HUQGTFTSDYSKYLDURAAQDFVK(PEG$_2$PEG$_2$γEC$_{18}$-OH)WL2DT-OH |
| 96 | TP811 | HUQGTFTSDYSKYLDURAAQDFVK(PEG$_2$PEG$_2$γEC$_{16}$-OH)WL2DT-NH$_2$ |
| 97 | TP812 | HUQGTFTSDYSKYLDARAAK(PEG$_2$PEG$_2$γEC$_{16}$-OH)EFVQWL2DT-NH$_2$ |
| 98 | TP813 | HUQGTFTSDYSKYLDARAAQEFVK(PEG$_2$PEG$_2$γEC$_{16}$-OH)WL2DT-NH$_2$ |
| 99 | TP814 | HUQGTFTSDYSKYLDARAAK(PEG$_2$PEG$_2$γEC$_{16}$-OH)DFVQWL2ET-NH$_2$ |
| 100 | TP815 | HUQGTFTSDYSKYLDURAAQDFVK(PEG$_2$PEG$_2$γEC$_{16}$-OH WL2ET-NH$_2$ |
| 101 | TP825 | HUQGTFTSDYSKYLDARAAQK(PEG$_2$PEG$_2$γEC$_{16}$-OH)FVQWL2ET-NH$_2$ |
| 102 | TP826 | HUQGTFTSDYSKYLDARAAK(PEG$_2$PEG$_2$γEC$_{16}$-OH)DFVQWL2γET-NH$_2$ |
| 103 | TP827 | HUQGTFTSDYSKYLDARAAQK(PEG$_2$PEG$_2$γEC$_{16}$-OH)FVQWL2γET-NH$_2$ |
| 104 | TP828 | HUQGTFTSDYSKYLDURAAQDFVK(PEG$_2$PEG$_2$γEC$_{16}$-OH)WL2γET-NH$_2$ |
| 109 | TP564 | HUQGTFTSDYSKYLDURAAK(PEG$_2$PEG$_2$γEC20-OH)DFVQWL2DT-NH$_2$ |
| 110 | TP575 | HUQGTFTSDYSKYLDURAAQDFVK(PEG$_2$PEG$_2$γEC18-OH)WL2DT-NH$_2$ |
| 111 | TP597 | HUQGTFTSDYSKLLDARAAK(PEG$_2$PEG$_2$γEC18-OH)DFVQWL2DT-NH$_2$ |
| 112 | TP598 | HUQGTFTSDYSKYLDAKAAK(PEG$_2$PEG$_2$γEC18-OH)DFVQWL2DT-NH$_2$ |
| 113 | TP604 | HUQGTFTSDYSKYLDARAAQDFVQWL2pAF(PEG$_2$PEG2γEC18-OH)T-NH$_2$ |

TABLE 1-continued

| SEQ ID NO: | ID | SEQUENCE |
|---|---|---|
| 114 | TP443 | HUQGTFTSDYSKYLDARAAQpAF(PEG$_2$PEG$_2$γEC18-OH)FVQWLLDT-NH$_2$ |
| 115 | TP608 | HUQGTFTSDYSKYLDARAAQK(PEG$_5$-γEC18-OH)FVQWL2aMDT-NH$_2$ |
| 116 | TP609 | HUQGTFTSDYSKYLDARAAQpAF(PEG$_2$PEG$_2$γEC18-OH)FVQWLLaMD-T-NH$_2$ |
| 117 | TP628 | HUQGTFTSDYSKYLDARAAK(PEG$_2$γEC18-OH)DFVQWL2αMDT-NH$_2$ |
| 118 | TP630 | HUQGTFTSDYSKYLDARAAK(PEG$_2$PEG$_2$γEC16-OH)DFVQαMWL2DT-NH$_2$ |
| 119 | TP640 | HUQGTFTSDYSKLLDARAAK(PEG$_2$PEG$_2$γEC18-OH)DFVQWL2αMDT-NH$_2$ |
| 120 | TP829 | HsQGTFTSDNle(1,2,3-triazole-4-C$_{15}$)SKYLDARAAQDFVQWLLDT-NH$_2$ |
| 121 | TP830 | HsQGTFTSDNle(1,2,3-triazole-4-γE-C$_{16}$)SKYLDARAAQDFVQWLLDT-NH$_2$ |
| 122 | TP831 | HsQGTFTSDNle(1,2,3-triazole-4-C$_4$-Lys-C$_{16}$)SKYLDARAAQDFVQWLLDT-NH$_2$ |

Table legend: U = alpha-aminoisobutyric acid; γE = γ-glutamic acid; 2 = L-methionine sulphone; αMD = alpha-Methyl-L-Aspartic acid; Nle = norleucine; αMF = alpha-Methyl-L-phenylalanine; αMS = alpha-Methyl-L-serine; αMW = alpha-methyl-L-tryptophan; s = D-serine; pAF = p-aminomethyl-L- phenylalanine; PEG$_2$ = 8-amino-3,6-dioxaoctanoic acid; PEG$_5$ = 1-hydroxy-3,6,9,12,15-pentaoxaoctadecan-18-oic acid; C$_4$ is C$_4$ alkyl; C$_{15}$ = C$_{15}$ alkyl; C$_{16}$ = C$_{16}$ alkyl; C$_x$ = C$_x$ alkyl; C$_{16}$–OH or C16–OH = —CO—(CH$_2$)$_{14}$—COOH; C$_{18}$–OH or C18–OH = —CO—(CH$_2$)$_{16}$—COOH; C$_{20}$–OH or C20–OH = —CO—(CH$_2$)$_{18}$—COOH; NH$_2$ = C-terminal amide..

The structure of Nle(1,2,3-triazole-5-PEG$_2$PEG$_2$γEC$_{18}$—OH) wherein the linker is PEG$_2$PEG$_2$γE and the fatty acid component comprises C18-OH is represented by (peptide SEQ ID NO:91):

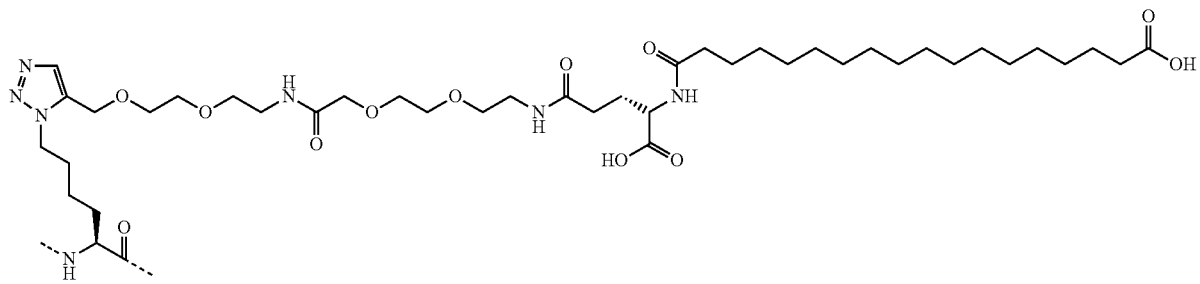

The GCG/GLP-1 receptor co-agonist peptides of the present invention are conjugated to an α,ω-dicarboxylic acid comprising an aliphatic chain of 14 to 20 methylene groups (fatty diacid) wherein one end of the molecule is the proximal end and the other end is the distal end and wherein the proximal end and the distal end both have a carboxyl (COOH) group. The fatty diacid may be represented by the structure HO$_2$C(CH$_2$)$_n$CO$_2$H, wherein n is 11, 12, 13, 14, 15, 16, 17 or 18. The fatty diacids include but are not limited to, the fatty diacids Tetradecanedioic acid, Hexadecanedioic acid, Heptadecanedioic acid, Octadecanedioic acid, Nonadecanedioic acid, and Eicosanedioic acid, respectively. The aforementioned fatty diacids have the following structures

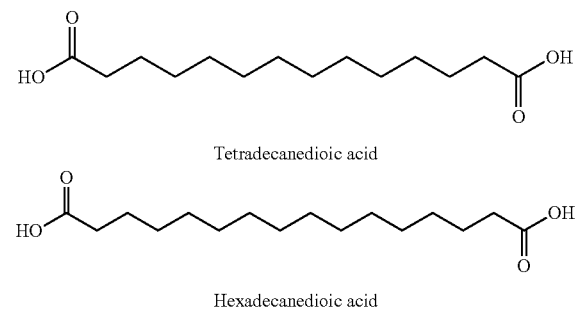

Tetradecanedioic acid

Hexadecanedioic acid

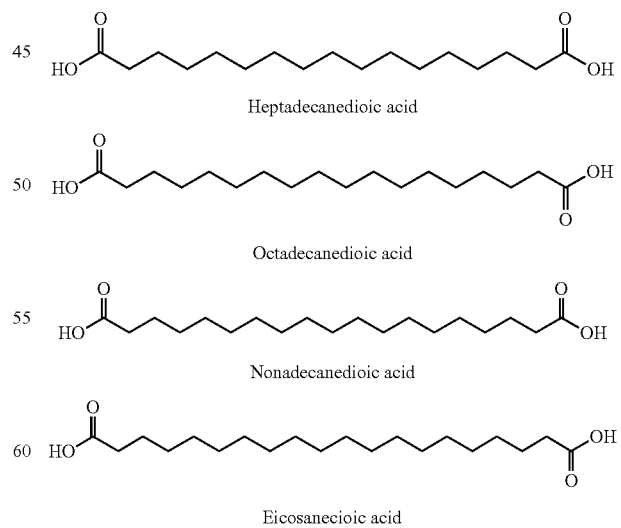

Heptadecanedioic acid

Octadecanedioic acid

Nonadecanedioic acid

Eicosanecioic acid

In particular aspects, the GCG/GLP-1 receptor co-agonist peptide is further conjugated to a fatty acid at position 10 of the peptide. The fatty acid may be represented by the structure $HO_2C(CH_2)_n$ wherein n is 11, 12, 13, 14, 15, 16, 17, 18, 19 or 20. The fatty acid may have one of the following structures

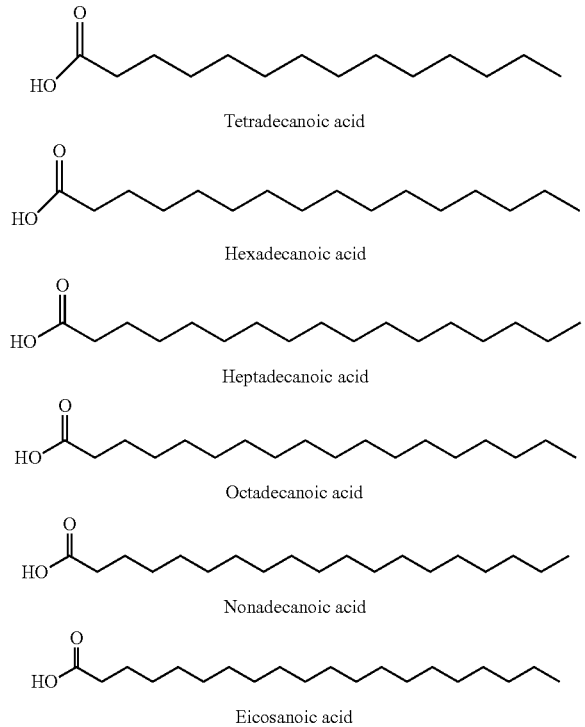

As a component of the GCG/GLP-1 receptor co-agonist peptide, the acid functionality at the proximal end of the fatty diacid is conjugated to the amino group of a linker in a C(O)—NH linkage and the acid functionality at the distal end of the fatty diacid is a free carboxyl group (COOH). The COOH group at the distal end helps confer a longer half-life to the co-agonist peptide by its ability to non-covalently bind to serum albumin, a known carrier for fatty acids in serum. The COOH group enhances duration of action as it provides a better non-covalent interaction with serum albumin than GCG/GLP-1 receptor co-agonist peptides that have been acylated using a fatty acid, which bind serum albumin less efficiently and form a less stable non-covalent interaction with the serum albumin. When the fatty diacid is conjugated to a linking moiety, it is subsequently referred to as a fatty acid component.

The linker may be $PEG_2$ (8-amino-3,6-dioxaoctanoic acid) linked to Gamma-Glutamic acid (gamma-Glu, γGlu, or γE), which has the structure

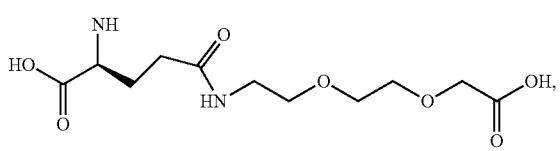 [SMILES: N[C@@H](CCC(=O)NCCOCCOCC(=O)O)C(=O)O]

or the linker may be Gamma-Glutamic acid-gamma glutamic acid (gamma-Glu-gamma-Glu, or γGlu-γGlu, or γEγE), which has the structure

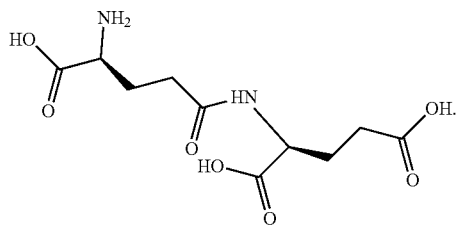 [SMILES: N[C@@H](CCC(=O)N[C@@H](CCC(=O)O)C(=O)O)C(=O)O]

The linker may also be $Peg_5$(1-hydroxy-3,6,9,12,15-pentaoxaoctadecan-18-oic acid) linked to Gamma-Glutamic acid (gamma-Glu, γGlu, or γE), which has the structure

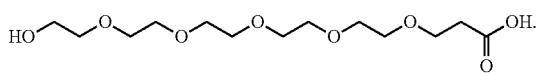 [SMILES: O=C(O)CCOCCOCCOCCOCCOCCO]

The structure of $K(PEG_2PEG_2γE$-fatty acid) wherein the linker is $PEG_2PEG_2γE$ and the fatty acid component comprises C14, C16, C17, C18, C19, or C20 is represented by

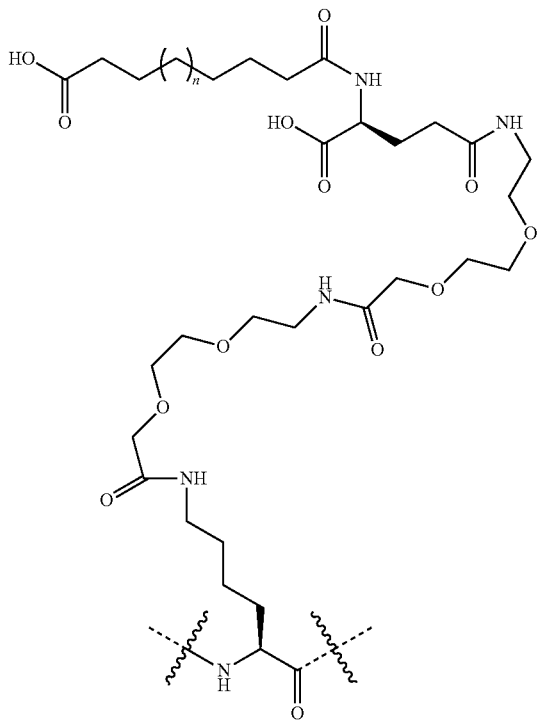

wherein n is 7, 9, 10, 11, 12, 13, or 14 respectively, and the wavy lines represent the bonds between adjacent amino acids in the co-agonist peptide sequence.

The structure of $pAF(PEG_2PEG_2γE$-fatty acid) wherein the linker is $PEG_2PEG_2γE$ and the fatty acid component comprises C14, C16, C17, C18, C19, or C20 is represented by

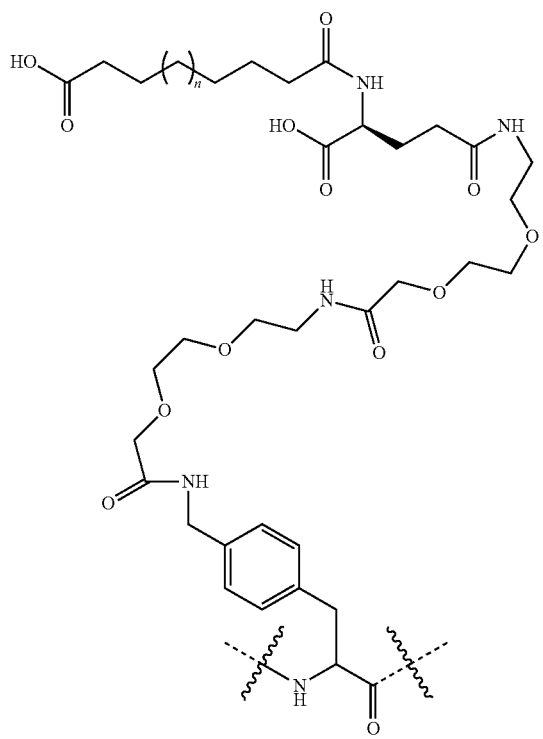

wherein n is 7, 9, 10, 11, 12, 13, or 14, respectively, and the wavy lines represent the bonds between adjacent amino acids in the co-agonist peptide sequence.

The structure of K(γEγE-fatty acid) wherein the linker is γEγE and the fatty acid component comprises C14, C16, C17, C18, C19, or C20 is represented by

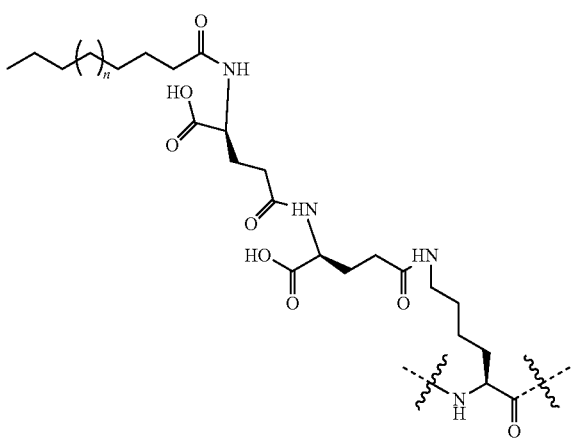

wherein n is 7, 9, 10, 11, 12, 13, or 14, respectively, and the wavy lines represent the bonds between adjacent amino acids in the co-agonist peptide sequence.

The structure of KγE at position 30 in the co-agonist peptide is represented by

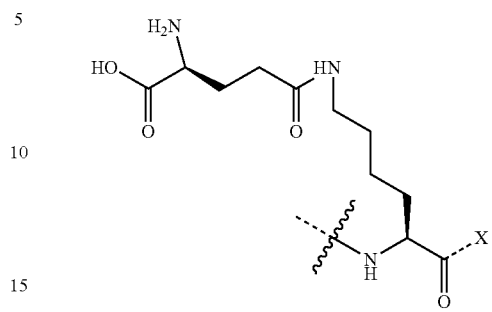

wherein the wavy line represents the bond between adjacent amino acids in the co-agonist peptide sequence, and wherein X is OH or $NH_2$.

The GCG/GLP-1 receptor co-agonist peptides disclosed herein may have anywhere from at least about 1% (including at least about 1.5%, 2%, 5%, 7%, 10%, 20%, 30%, 40%, 50%, 60%, 75%, 100%, 125%, 150%, 175%) to about 200% or higher activity at the GLP-1 receptor relative to native GLP-1 and anywhere from at least about 1% (including about 1.5%, 2%, 5%, 7%, 10%, 20%, 30%, 40%, 50%, 60%, 75%, 100%, 125%, 150%, 175%, 200%, 250%, 300%, 350%, 400%, 450%) to about 500% or higher activity at the glucagon receptor relative to native glucagon.

In some embodiments, the GCG/GLP-1 receptor co-agonist peptides described herein exhibit no more than about 100%, 1000%, 10,000%, 100,000%, or 1,000,000% of the activity of native glucagon at the glucagon receptor.

In some embodiments, the GCG/GLP-1 receptor co-agonist peptides described herein exhibit no more than about 100%, 1000%, 10,000%, 100,000%, or 1,000,000% of the activity of native GLP-1 at the GLP-1 receptor.

In exemplary embodiments, a GCG/GLP-1 receptor co-agonist peptide may exhibit at least 10% of the activity of native glucagon at the glucagon receptor and at least 50% of the activity of native GLP-1 at the GLP-1 receptor, or at least 40% of the activity of native glucagon at the glucagon receptor and at least 40% of the activity of native GLP-1 at the GLP-1 receptor, or at least 60% of the activity of native glucagon at the glucagon receptor and at least 60% of the activity of native GLP-1 at the GLP-1 receptor.

Selectivity of a GCG/GLP-1 receptor peptide for the glucagon receptor versus the GLP-1 receptor can be described as the relative ratio of glucagon/GLP-1 activity (the peptide analog's activity at the glucagon receptor relative to native glucagon, divided by the peptide's activity at the GLP-1 receptor relative to native GLP-1). For example, a GCG/GLP-1 receptor co-agonist peptide that exhibits 60% of the activity of native glucagon at the glucagon receptor and 60% of the activity of native GLP-1 at the GLP-1 receptor has a 1:1 ratio of glucagon/GLP-1 activity. Exemplary ratios of glucagon/GLP-1 activity include about 1:1, 1.5:1, 2:1, 3:1, 4:1, 5:1, 6:1, 7:1, 8:1, 9:1 or 10:1, or about 1:10, 1:9, 1:8, 1:7, 1:6, 1:5, 1:4, 1:3, 1:2, or 1:1.5. As an example, a glucagon/GLP-1 activity ratio of 10:1 indicates a 10-fold selectivity for the glucagon receptor versus the GLP-1 receptor. Similarly, a GLP-1/glucagon activity ratio of 10:1 indicates a 10-fold selectivity for the GLP-1 receptor versus the glucagon receptor.

Pharmaceutical Compositions

Further provided are pharmaceutical compositions comprising a therapeutically effective amount of one or more of the GCG/GLP-1 receptor co-agonist peptides disclosed herein for the treatment of a metabolic disorder in an individual. Such disorders include, but are not limited to, obesity, metabolic syndrome or syndrome X, Type II diabetes, complications of Type II diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, Type II diabetes, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of a GCG/GLP-1 receptor co-agonist peptide to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The GCG/GLP-1 receptor co-agonist peptides are useful for treating both Type I and Type II diabetes. The GCG/GLP-1 receptor co-agonist peptides are especially effective for treating Type II diabetes. The GCG/GLP-1 receptor co-agonist peptides are also useful for treating and/or preventing gestational diabetes mellitus.

U.S. Pat. No. 6,852,690, which is incorporated herein in its entirety, discloses methods for enhancing metabolism of nutrients comprising administering to a non-diabetic patient a formulation comprising a nutritively effective amount of one or more nutrients or any combination thereof and one or more insulinotropic peptides. The GCG/GLP-1 receptor co-agonist peptides disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the GCG/GLP-1 receptor co-agonist peptides disclosed herein.

The GCG/GLP-1 receptor co-agonist peptides disclosed herein may be used in a pharmaceutical composition when combined with a pharmaceutically acceptable carrier. Such compositions comprise a therapeutically-effective amount of one or more of the co-agonist peptides disclosed herein and a pharmaceutically acceptable carrier. Such a composition may also be comprised of (in addition to the co-agonist peptides disclosed herein and a carrier) diluents, fillers, salts, buffers, stabilizers, solubilizers, and other materials well known in the art. Compositions comprising the co-agonist peptides disclosed herein can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising a compound as disclosed herein are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, trifluoro acetate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to the GCG/GLP-1 receptor co-agonist peptides disclosed herein are meant to also include the pharmaceutically acceptable salts. The invention also includes counterions, including pharmaceutically acceptable counterions, including but not limited to, sodium, acetate and trifluoro acetate.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The GCG/GLP-1 receptor co-agonist peptides disclosed herein may be in multimers (for example, heterodimers or homodimers) or complexes with itself or other peptides. As a result, pharmaceutical compositions of the invention may comprise one or more co-agonist peptides disclosed herein in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition may comprise one or more co-agonist peptides disclosed herein; one or more co-agonist peptides disclosed herein and one or more other agents for treating a metabolic disorder; or the pharmacological composition comprising the one or more co-agonist peptides disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When a GCG/GLP-1 receptor co-agonist peptide is used contemporaneously with one or more other drugs, peptides, or proteins, a pharmaceutical composition containing such other drugs, peptides, or proteins in addition to the GCG/GLP-1 receptor co-agonist peptide may be provided. Accordingly, the pharmaceutical compositions of the present invention include those that also contain one or more other active ingredients, in addition to a GCG/GLP-1 receptor co-agonist peptide. Examples of other proteins that may be included in the composition include but are not limited to human insulin or human insulin analog such as insulin detemir, insulin glargine (U100 or U300), insulin levemir, insulin glulisine, insulin degludec, or insulin lispro.

Methods of administrating the pharmacological compositions comprising the one or more GCG/GLP-1 receptor co-agonist peptides disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local.

Various delivery systems are known and can be used to administer the GCG/GLP-1 receptor co-agonist peptides disclosed herein including, but not limited to, encapsulation in liposomes, microparticles, microcapsules; minicells; polymers; capsules; tablets; and the like. In one embodiment, the co-agonist peptides disclosed herein may be delivered in a vesicle, in particular a liposome. In a liposome, the co-agonist peptides disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the co-agonist peptides disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the GCG/GLP-1 receptor co-agonist peptides disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more co-agonist peptides disclosed herein are generally about 5-500 micrograms (μg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient. The peptides may be administered on a regimen including, but not limited to, 1 to 4 times per day, once every 2 days, once every 3 days, once every 4 days, once every 5 days once every 6 days or once a week. Ultimately the attending physician will decide on the appropriate duration of therapy using compositions comprising the one or more co-agonist peptides disclosed herein of the present invention. Dosage will also vary according to the age, weight and response of the individual patient.

Further provided is a pharmaceutical pack or kit, comprising one or more containers filled with one or more of the ingredients of the pharmaceutical compositions and co-agonist peptides disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

The present invention further provides a method for treating a patient for a metabolic disease or disorder comprising administering the patient an effective amount of a composition comprising any one or more of the aforementioned GCG/GLP-1 receptor co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned GCG/GLP-1 receptor co-agonist peptides for manufacture of a medicament for the treatment of a metabolic disease or disorder.

The present invention further provides for the use of any one of the aforementioned GCG/GLP-1 receptor co-agonist peptides for manufacture of a medicament for the treatment of a metabolic disease or disorder.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a GCG/GLP-1 receptor co-agonist peptide and administering to the patient or individual an effective amount of a composition comprising an insulin or insulin analog to treat the metabolic disease or disorder in the patient or individual.

In particular aspects, the composition comprising the GCG/GLP-1 receptor co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin is human insulin or a human insulin analog such as insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned GCG/GLP-1 receptor co-agonist peptides; an insulin or insulin analog; and, a pharmaceutically acceptable carrier.

The present invention further provides for the use of a composition comprising any one of the aforementioned GCG/GLP-1 receptor co-agonist peptides; an insulin or insulin analog; and, a pharmaceutically acceptable carrier for the treatment of a metabolic disease or disorder.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition comprising any one of the aforementioned GCG/GLP-1 receptor co-agonist peptides; an insulin or insulin analog; and, a pharmaceutically acceptable carrier for the manufacture of a medicament for the treatment of a metabolic disease or disorder.

In particular aspects, the insulin analog comprises insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The following examples are intended to promote a further understanding of the present invention.

EXAMPLE 1

Peptides in Table 1 were synthesized by solid phase synthesis using Fmoc/t-Bu chemistry on a peptide multisynthesizer Symphony (Protein Technologies Inc.) on a 150 μmol scale, using either a Rink-amide PEG-PS resin (Champion, Biosearch Technologies, loading 0.28 mmol/g) or a Rink-amide PS resin (ChemImpex loading 0.47 mmol/g).

All the amino acids were dissolved at a 0.3 M concentration in DMF. The amino acids were activated with equimolar amounts of HATU (O-(7-azabenzotriazol-1-yl)-N,N,N',N'-tetramethyluronium hexafluorophosphate) solution 0.3 M in DMF, and a 2-fold molar excess of DIEA (N,N-diisopropylethylamine), solution 2M in NMP. The acylation reactions were performed in general for 1 hour with a 5-fold excess of activated amino acid over the resin free amino groups with double 45 minutes acylation reactions performed from $His^1$ to $Thr^7$ and from $F^{22}$ to $V^{23}$ and from $D/E^{15}$ to $Aib^{16}$ for sequences containing $Aib^{16}$.

The side chain protecting groups were: tert-butyl for Asp, αMD, Glu, Ser, αMS, D-Ser, Thr and Tyr; trityl for Gln and His; tert-butoxy-carbonyl for Lys, Trp; and, 2,2,4,6,7-pentamethyldihydrobenzofuran-5-sulfonyl for Arg; His was introduced as Boc-His(Trt)—OH at the end of the sequence assembly. Amino acid 2 (L-methionine-sulphone) was introduced by acylation of Fmoc-L-methionine-sulphone-COOH. For all the sequences containing alpha methyl amino acids, incorporation of the alpha methyl amino acid and the corresponding following residue were performed by manual coupling with HOAt (Hydroxybenzoazatriazole) and DIC (N,N'-diisopropylcarbodiimide). The position used for linker-lipid derivatization, either lysine or pAF (p-aminomethyl-L-phenylalanine) were incorporated with a Dde

[1-(4,4-dimethyl-2,6-dioxocyclohex-1-ylidene)ethyl] or Alloc (Allyloxy-carbonyl) protecting groups on the side chain amino group. In sequence ID 91 the position used for linker derivativation was incorporated as Fmoc-Nle(1,2,3-triazole-5-PEG$_2$-NH-ivDde as manual coupling using HOAt, DIC. For sequences with double lipids, sequences ID 25, 29 and 30, position 10 was incorporated as Lys(Alloc)—OH and the second position for the lipid diacid derivatization was incorporated as Lys(Dde)—OH. The pAF [Fmoc-4-(Dde-aminomethyl)-phenylalanine] and the Fmoc-Nle(1,2,3-triazole-5-PEG$_2$-NH-ivDde amino acids were synthesized as described below.

At the end of the sequence assembly, to proceed with linker/lipid derivatization, the Dde protecting group of either pAF(Dde) or Lys(Dde) or Nle(1,2,3-triazole-5-PEG$_2$-NH-ivDde was removed by treatment of 2% hydrazine in DMF. The side chains of Lys or pAF or Nle(1,2,3-triazole-5-PEG$_2$-NH$_2$ were derivatized with different linkers and fatty diacids by incorporation of Fmoc-Glu-OtBu (γ-glutamic acid), Fmoc-PEG2 [8-(9-Fluorenylmethyloxycarbonyl-amino)-3,6-dioxaoctanoic acid] and the lipid diacids (; Hexadecanedioic acid; Octadecanedioic acid; Eicosanedioic acid) using HOAt and DIC as activators.

For double lipidated sequences ID 25, 29, 30, the Alloc protecting group from Lys10 was first removed by treatment with Pd(PPh3)4 and PhSiH3 in DCM (dichloromethane) followed by derivatization with Fmoc-Glu-OtBu (γ-glutamic acid) and hexanenoic acid. Then deprotection of the Dde from the other Lys followed by derivatization with linker/lipid diacids was performed as described above for the other lapidated analogs.

At the end of the synthesis, the dry peptide-resins were individually treated with 25 mL of the cleavage mixture, 88% TFA, 5% phenol, 2% triisopropylsilane and 5% water for 1.5 hours at room temperature. Each resin was filtered and then added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in H$_2$O, 20% acetonitrile, and lyophilized. The crude peptides (140 mg in 3 mL of DMSO) were purified by reverse-phase HPLC using preparative Waters Deltapak C4 (40×200 mm, 15 μm, 300 Å) and using as eluents (A) 0.1% TFA in water and (B) 0.1% TFA in acetonitrile.

Analytical HPLC was performed on a Acquity UPLC Waters Chromatograph with a BEH300 C$_4$ Acquity Waters column 2.1×100 mm, 1.7 μm, at 45° C., using H$_2$O, 0.1% TFA (A) and CH$_3$CN, 0.1% TFA (B) as solvents. The peptides were characterized by electrospray mass spectrometry on an Acquity SQ Detector.

Synthesis of Fmoc-4-(Dde-aminomethyl)-phenylalanine.

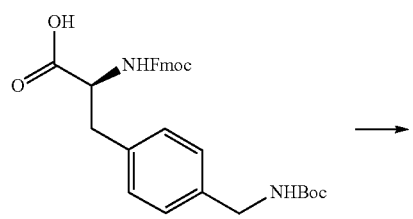

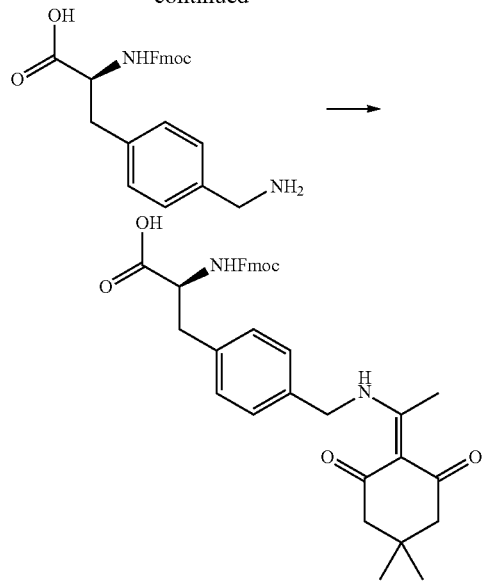

Fmoc-4-(Boc-aminomethyl)-phenylalanine was stirred in DCM/TFA 2/1 for 1 hour. The solvents were removed under reduced pressure and the residue was treated with diethyl ether to obtain a solid. The crude material obtained was dissolved in EtOH (19 mM), DIPEA (5 eq) and Dimedone (1.1 eq) were added to the reaction mixture. After 3 hours at 60° C. the solution was acidified with TFA to pH 4. The solvents were removed under reduced pressure and the residue was treated with AcOEt and washed with HCl 1N. The organic phase was washed with brine and dried over Na$_2$SO$_4$. The solvents were removed under reduced pressure and the final product was obtained as yellow oil which was further treated with Et$_2$O to obtain a solid.

The final compound was characterized on an Acquity UPLC Waters Chromatograph, with BEH300 C$_{18}$ Acquity Waters 2.1×100 mm, 1.7 μm, at 45° C., using H$_2$O, 0.1% TFA (A) and CH$_3$CN, 0.1% TFA (B) as solvents and the following gradient: 10% A to 10% B in 1 min, 10% B over 90% B in 4 min, flow 0.4 mL/min. The protected amino acid was characterized by electrospray mass spectrometry on an Acquity SQ Detector (Mw found: 581.5 Da; Mw expected: 580.67 Da).

Synthesis of Fmoc-Nle(1,2,3-triazole-5-PEG$_2$-NH-ivDde

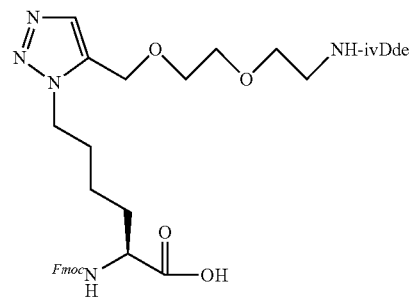

was as follows.

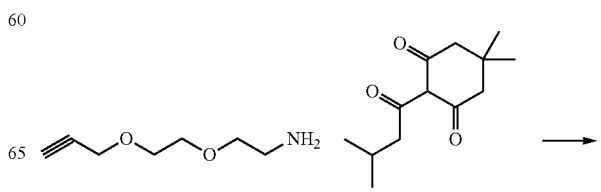

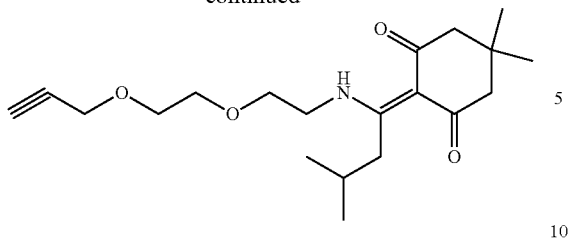

TFA (0.013 mL, 0.175 mmol) was added to a stirred suspension of 2-(2-(prop-2-yn-1-yloxy)ethoxy)ethanamine (250 mg, 1.746 mmol) and 5,5-dimethyl-2-(3-methylbutanoyl)cyclohexane-1,3-dione (0.763 mL, 3.49 mmol) in ethanol (15 mL) at rt. The mixture was then refluxed for 24 hours and the solvent was rotary-evaporated. The residue was purified by silica gel chromatography (eluent: 0-15% methanol in DCM) to give 5,5-dimethyl-2-(3-methyl-1-((2-(2-(prop-2-yn-1-loxy)ethoxy)ethyl)amino)butylidene)cyclohexane-1,3-dione as light yellow oil in 82% yield.

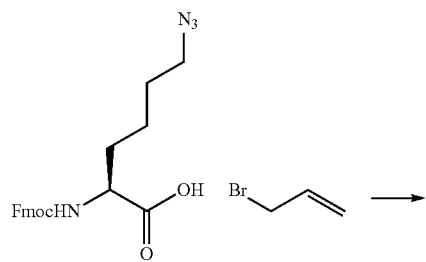

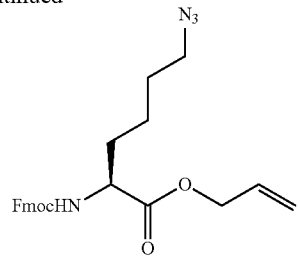

A DCM (dichloromethane) solution of Fmoc-Lys(N3)—OH (500 mg, 1.268 mmol) was slowly added to a solution of NaHCO$_3$ (1 eq) in water (3 mL/mmol NaHCO$_3$). This was added to a solution of TBAB (tetrabutylammonium bromide; 1 eq) and allyl bromide (5.28 eq) in DCM (1.1 mL/mmol allyl bromide). The emulsion was stirred vigorously for 24 h at room temperature and was then extracted with DCM three times. The organic extracts were dried over MgSO$_4$, and solvent was evaporated. The residue was purified by flash chromatography (SiO$_2$, ethyl acetate:hexanes 0-50%) to obtain the product (S)-allyl 2-((((9H-fluoren-9-yl)methoxy)carbonyl)amino)-6-azidohexanoate as white solids in 92% yield.

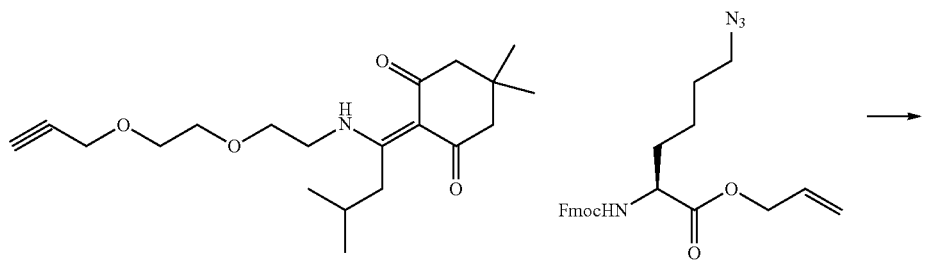

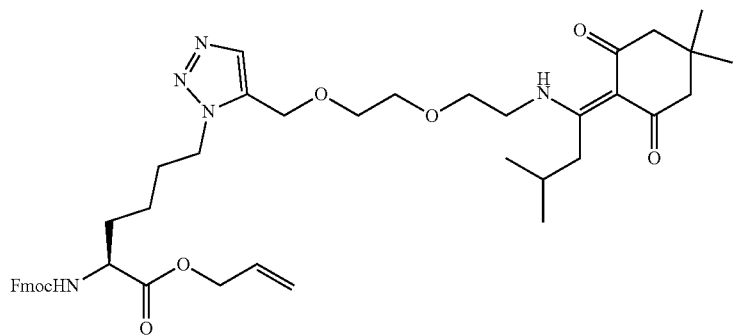

In glovebox, Cp*RuCl(PPh₃)₂ (65.6 mg, 0.082 mmol) was added to a microwave tube with a septa cap. Dioxane (5 mL) was added. 5,5-dimethyl-2-(3-methyl-1-((2-(2-(prop-2-yn-1-yloxy)ethoxy)ethyl)amino)butylidene)cyclohexane-1,3-dione (360 mg, 1.030 mmol) was dissolved in dioxane (2.5 mL) and added to the catalyst solution. Last, (S)-allyl 2-((((9H-fluoren-9-yl)methoxy)carbonyl)amino)-6-azidohexanoate (448 mg, 1.030 mmol) was added in dioxane (2.5 mL) to the reaction mixture. The reaction was heated in an oil bath at 60° C. for 12 hours. The solvent was evaporated and the residue was purified by flash chromatography (80 g SiO₂, ethyl acetate:hexanes 0-60% and then dichloromethane/methanol 0-20%) to give the product (S)-allyl 2-((((9H-fluoren-9-yl)methoxy)carbonyl)amino)-6-(5-((2-(2-((1-(4,4-dimethyl-2,6-dioxocyclohexylidene)-3-methylbutyl)amino)ethoxy)ethoxy)methyl)-1H-1,2,3-triazol-1-yl)hexanoate as light yellow solid in 60% yield.

Synthesis of Nle(1,2,3-triazole-4-C₁₅)

The structure of Nle(1,2,3-triazole-4-C₁₅) wherein the linker is C₁₅ alkyl is represented by

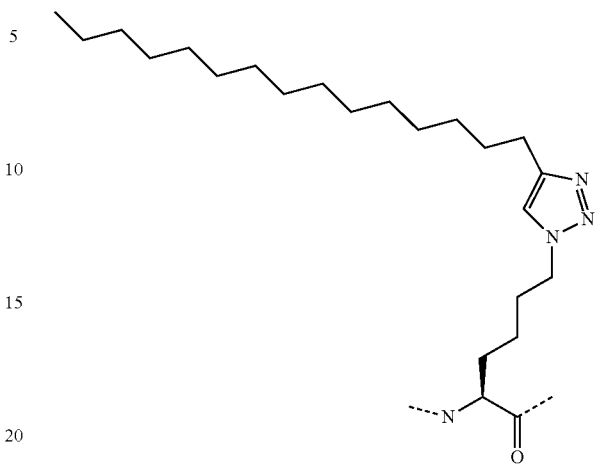

The GCG/GLP-1 receptor co-agonist peptides of the present invention of the following formula: (HsQGTFTSDK(N3)SKYLDARAAQDFVQWLLDT-NH₂) (SEQ ID NO: 126) are connected to the linker through click chemistry described below

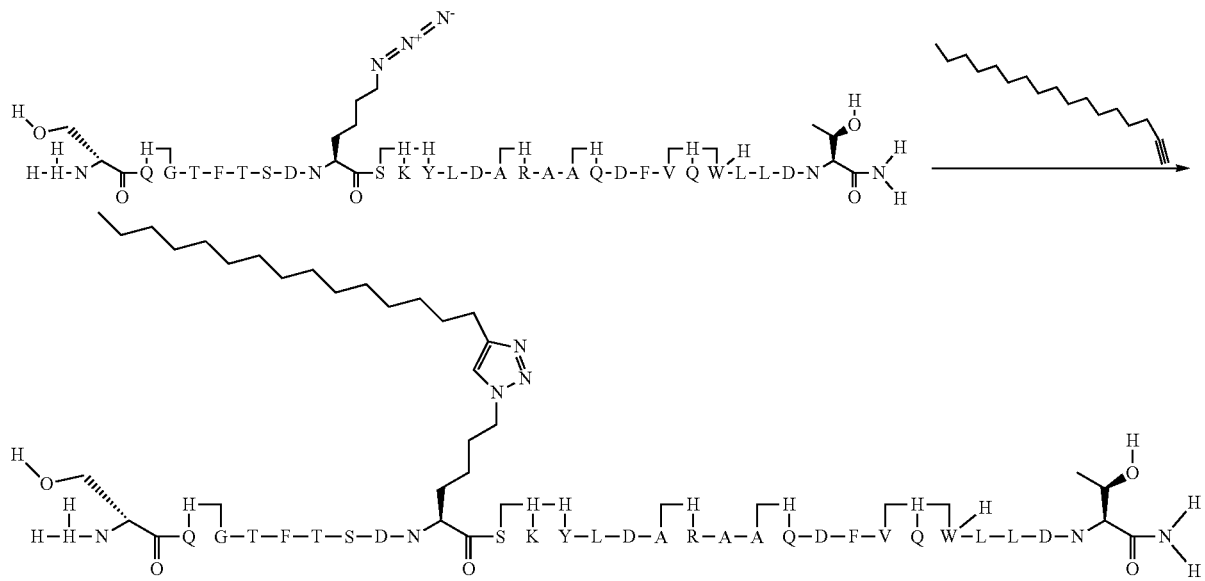

HsQGTFTSD(Lys(N3)}SKYLDARAAQDFVQWLLD (SEQ ID NO: 127) (Biopeptek #173501-2, 100 mg, 0.030 mmol) and heptadec-1-yne (10.57 mg, 0.045 mmol) were dissolved in DMSO (6 mL). To this solution was added dropwise CuSO₄*5H₂O in water (3.0 mg/ml, 1.979 ml, 0.024 mmol) freshly mixed with aqueous sodium ascorbate (5904 μl, 0.119 mmol) in a water bath. The mixture was bubbled with N₂ for 30 seconds, then sealed and shaken at room temperature for 18 hours. Then the reaction pH was adjusted to pH 3 using TFA. The resulting clear solution was filtered for purification (RPLC, column: Waters CSH C18 5μ, 19×150 mm; flowrate: 25 ml/min; gradient: water/ACN (acetonitrile) with 0.05% TFA 35-42%). Fractions containing the desired product were combined and lyophilized to give the title compound (10.1 mg, 2.70 μmol, 9.06% yield, purity 96%).

EXAMPLE 2

Synthetic for peptide of sequence:

(SEQ ID NO: 110)
HUQGTFTSDYSKYLDURAAQDFVK(PEG2PEG2γEC18-OH)WL2DT-NH2 legend: U=aminoisobutyric acid; 2=L-methionine sulphone; PEG2=8-amino-3,6-dioxaoctanoic acid; γE=γ-glutamic acid; C18-OH (Octadecanedioic acid)=—CO—(CH2)16-COOH; tBu=tert butyl; and fmoc=9-fluorenylmethyl chloroformate.

The peptide was synthesized by solid phase synthesis using Fmoc/t-Bu chemistry on a peptide multisynthesizer Symphony (Protein Technologies Inc.) on a 180 μmol scale, using a Rink-amide PS resin (Novabiochem, loading 0.35 mmol/g). All the amino acids were dissolved at a 0.3 M concentration in DMF (dimethyl formamide). The amino acids were activated with equimolar amounts of HATU (O-(7-azabenzotriazol-1-yl)-N,N,N',N'-tetramethyluronium hexafluoro-phosphate) solution 0.3 M in DMF, and a 2-fold molar excess of DIEA (N,N-diisopropyl-ethylamine), solution 2M in NMP (N-methyl pyrrolidine). The acylation reactions were performed in general for 1 hour with a 5-fold excess of activated amino acid over the resin free amino groups with double 45 minutes acylation reactions performed from His$^1$ to Thr$^7$, from F$^{22}$ to V$^{23}$ and from D$^{15}$ to Aib$^{16}$. The side chain protecting groups were: tert-butyl for Glu, Ser, D-Ser (ser), Thr and Tyr; trityl for Asn, Gln and His; tert-butoxy-carbonyl for Lys, Trp; and, 2,2,4,6,7-pentamethyldihydro-benzofuran-5-sulfonyl for Arg. His was introduced as Boc-His(Trt)-OH at the end of the sequence assembly. Amino acid alpha-aminoisobutyric acid (Aib) was introduced by acylation of Fmoc-Aib-OH. Amino acid γ-Glu (γ-glutamic acid) was introduced by acylation of Fmoc-Glu-OtBu. Amino acid 2 (L-methionine-sulphone) was introduced by acylation of Fmoc-L-methionine-sulphone-COOH. The lysine used for linker-lipid derivatization was incorporated with a Dde [1-(4,4-dimethyl-2,6-dioxocyclohex-1-ylidene)ethyl] protecting group on the side chain of amino group. After the assembly the Dde protecting group of Lys (Dde) was removed by treatment of 2% hydrazine in DMF. The side chain of Lys was derivatized with Fmoc-PEG$_2$ [8-(9-Fluorenylmethyloxycarbonyl-amino)-3,6-dioxaoctanoic acid], Fmoc-Glu-OtBu (γ-glutamic acid) using HOAt (1-Hydroxy-7-azabenzotriazole) and DIC as activators in DMF. The lipid diacid (Octadecanedioic acid) was introduced manually using HOAt and DIC as activators in NMP. At the end of the synthesis, the dry peptide-resin was individually treated with 35 mL of the cleavage mixture, 88% TFA (trifluoroacetic acid), 5% phenol, 2% triisopropylsilane and 5% water for 3 hours at room temperature. Each resin was filtered and then added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in H$_2$O, 20% acetonitrile, and lyophilized. The crude peptide was purified by reverse-phase HPLC using preparative Waters Deltapak C4 (40×200 mm, 15 μm, 300 Å) and using as eluents (A) 0.1% TFA in water and (B) 0.1% TFA in acetonitrile in order to obtain pure linear peptide. The final peptide was characterized on an Acquity UPLC Waters Chromatograph, with BEH130 C4 Acquity Waters 2.1×100 mm, 1.7 μm, at 45° C., using H2O, 0.1% TFA (A) and CH$_3$CN, 0.1% TFA (B) as solvents. The peptide was characterized by electrospray mass spectrometry on a Acquity SQ Detector. (MW found: 4140.6 Da; MW expected: 4141.67).

EXAMPLE 3

Activity of the peptides at the Glucagon receptor (GCGR) and GLP-1 receptor (GLP1R) was measured in a cAMP activity assay.

GCG/GLP-1 receptor co-agonist peptides were dissolved in 100% DMSO (dimethyl sulfoxide) and serially diluted to generate 10 point titrations. The peptide solutions were then transferred into 384-well assay plates (150 nL/well). Assay ready frozen cells expressing human GLP1R or human GCGR were suspended in growth media consisting of DMEM medium (GIBCO®), 10% FBS (GIBCO®), 1×NEAA(GIBCO®), 1×P/S (GIBCO®), 10 ug/mL Blasticidin (GIBCO®) and 200 μg/mL Hygromycin (GIBCO®). Cells were then diluted in assay buffer consisting of PBS (GIBCO®), 7.5% BSA (Perkin Elmer), 100 μM RO 20-1724 (Sigma), with or without 20% human serum (MP Biomedical). The cell suspensions (15 μL) were then added to the assay plates containing the peptide solutions (30,000 cells/well for human GCGR; 10,000 cells/well for human GLP1R). The cells were incubated for 1 hour at room temperature in the dark. Production of cAMP was determined using HitHunter™ cAMPXS kits (DiscoverX) following manufacturer protocol. The plates were incubated for overnight at room temperature in the dark. Luminescence was measured using an EnVision Multilabel plate reader (Perkin Elmer). Native GLP-1 and Glucagon (Bachem) are used as control peptides. EC$_{50}$ values were calculated using uses a 4 parameter logistic fit based on the Levenberg-Marquardt algorithm. The results are shown in Table 2.

TABLE 2

| SEQ ID NO: | Peptide Name | GCGR EC50 human (nM) | GLP1R EC50 human (nM) | hGCGR/h GLP1R (hTone) |
|---|---|---|---|---|
| 1 | TP565 | 5.420 | 2.260 | 2.4 |
| 2 | TP579 | >19.9 | 14.7 | |
| 3 | TP583 | 6.37 | 0.74 | 8.6 |
| 4 | TP584 | 6 | 1.3 | 4.6 |
| 5 | TP578 | 0.604 | 4.95 | 0.1 |
| 6 | TP580 | 1.09 | 0.46 | 2.4 |
| 7 | TP581 | 4.95 | 1.69 | 2.9 |
| 8 | TP582 | 4.95 | 2.57 | 1.9 |
| 9 | TP585 | 1.13 | 0.566 | 2.0 |
| 10 | TP588 | 2.67 | 2.92 | 0.9 |
| 11 | TP589 | 19.8 | 2.07 | 9.6 |
| 12 | TP590 | 5.03 | 1.64 | 3.1 |
| 13 | TP592 | 3.39 | 2.42 | 1.4 |
| 14 | TP594 | 4.95 | 2.6 | 1.9 |
| 15 | TP576 | 1.45 | 1.88 | 0.8 |
| 16 | TP577 | 4.54 | 1.67 | 2.7 |
| 17 | TP586 | 4.95 | 1.23 | >4.0 |
| 18 | TP587 | 2.49 | 0.41 | >4.1 |
| 19 | TP591 | 2.88 | 1.31 | 2.2 |
| 20 | TP593 | 0.73 | 4.95 | <0.15 |
| 21 | TP595 | 0.4 | >20 | 0.2 |
| 22 | TP596 | 0.35 | >20 | 0.2 |
| 23 | TP599 | 3.47 | 2.21 | 1.6 |
| 24 | TP600 | 1.75 | 0.57 | 3.1 |
| 25 | TP601 | 1.8 | 8.5 | 0.2 |
| 26 | TP602 | 2.17 | 0.36 | 6.3 |
| 27 | TP603 | 1.88 | 1.17 | 1.6 |
| 28 | TP605 | 3.75 | 1.98 | 1.9 |
| 29 | TP606 | 1.01 | 1.84 | 0.5 |
| 30 | TP607 | 0.57 | 1.06 | 0.5 |
| 31 | TP610 | 0.19 | >5 | <0.01 |
| 32 | TP611 | 0.2 | >5 | <0.02 |

TABLE 2-continued

| SEQ ID NO: | Peptide Name | GCGR EC50 human (nM) | GLP1R EC50 human (nM) | hGCGR/hGLP1R (hTone) |
|---|---|---|---|---|
| 33 | TP612 | 2.04 | 4.95 | <0.41 |
| 34 | TP613 | >5 | 3.34 | >6 |
| 35 | TP614 | 0.86 | 1.4 | 0.6 |
| 36 | TP615 | 0.26 | 0.4 | 0.6 |
| 37 | TP616 | 1.39 | 1.96 | 0.7 |
| 38 | TP617 | 0.56 | 0.76 | 0.8 |
| 39 | TP618 | 0.36 | 2.48 | 0.1 |
| 40 | TP619 | 0.05 | 0.38 | 0.1 |
| 41 | TP620 | 1.26 | 8.58 | 0.1 |
| 42 | TP621 | 0.25 | 1.94 | 0.1 |
| 43 | TP622 | 0.03 | 0.09 | 0.4 |
| 44 | TP623 | 0.09 | 0.17 | 0.5 |
| 45 | TP624 | 1 | 0.89 | 1.1 |
| 46 | TP625 | 1.3 | 0.39 | 3.4 |
| 47 | TP626 | 0.39 | 0.77 | 0.6 |
| 48 | TP627 | 0.14 | 0.25 | 0.6 |
| 49 | TP629 | 3.17 | 2.23 | 1.4 |
| 50 | TP631 | 1.65 | 1.32 | 1.3 |
| 51 | TP632 | 5.9 | 6.6 | 0.9 |
| 52 | TP633 | 0.12 | 0.19 | 0.7 |
| 53 | TP634 | 0.77 | 0.49 | 1.6 |
| 54 | TP635 | 0.46 | 2.13 | 0.2 |
| 55 | TP636 | 0.11 | 0.52 | 0.2 |
| 56 | TP637 | 0.94 | 0.53 | 1.8 |
| 57 | TP638 | 5.05 | 1.55 | 3.3 |
| 58 | TP639 | 3.38 | 2.09 | 1.6 |
| 59 | TP657 | 0.14 | 2.18 | 0.1 |
| 60 | TP658 | 3.2 | 1.66 | 1.9 |
| 61 | TP659 | 0.46 | >4.9 | NA |
| 62 | TP660 | 4.54 | 3.59 | 1.3 |
| 63 | TP661 | 0.61 | >19.8 | NA |
| 64 | TP662 | 1.45 | 0.52 | 2.8 |
| 65 | TP663 | 0.22 | 0.38 | 0.6 |
| 66 | TP664 | 0.36 | 0.22 | 1.7 |
| 67 | TP665 | 0.79 | 1.6 | 4.9 |
| 68 | TP666 | >19.8 | >19.8 | NA |
| 69 | TP667 | >19.8 | >19.8 | NA |
| 70 | TP672 | 0.35 | 0.51 | 0.7 |
| 71 | TP673 | 0.22 | 0.67 | 0.3 |
| 72 | TP674 | 1.08 | 0.45 | 2.4 |
| 73 | TP675 | 0.3 | 0.71 | 0.4 |
| 74 | TP676 | 0.82 | 0.26 | 3.1 |
| 75 | TP677 | 1.42 | 0.76 | 1.9 |
| 76 | TP678 | 0.25 | 0.91 | 0.3 |
| 77 | TP679 | 0.13 | 0.18 | 0.7 |
| 78 | TP680 | 0.59 | 0.19 | 3.0 |
| 79 | TP681 | 0.27 | 0.15 | 1.8 |
| 80 | TP682 | 2.35 | 2.31 | 1.0 |
| 81 | TP683 | 4.97 | 0.62 | NA |
| 82 | TP685 | 4.97 | 1.12 | 7.9 |
| 83 | TP693 | 1.1 | >4.9 | NA |
| 84 | TP699 | >19.8 | >19.8 | NA |
| 85 | TP700 | >4.9 | 0.35 | NA |
| 86 | TP701 | >4.9 | 0.18 | NA |
| 87 | TP702 | 0.35 | 0.27 | 1.4 |
| 88 | TP703 | >19.8 | >19.8 | NA |
| 89 | TP704 | 0.27 | 0.37 | 0.7 |
| 90 | TP705 | 1.48 | 0.41 | 3.6 |
| 91 | TP712 | 0.25 | 0.45 | 0.6 |
| 92 | TP713 | 1.52 | 0.71 | 2.2 |
| 93 | TP735 | 0.895 | 0.648 | 1.4 |
| 94 | TP736 | 3.19 | 1.145 | 2.8 |
| 95 | TP737 | 1.56 | 2.67 | 0.6 |
| 96 | TP811 | 0.21 | 0.26 | 0.8 |
| 97 | TP812 | 0.2 | 0.088 | 2.3 |
| 98 | TP813 | 0.21 | 0.14 | 1.6 |
| 99 | TP814 | 0.156 | 0.078 | 2.0 |
| 100 | TP815 | 0.084 | 0.12 | 0.7 |
| 101 | TP825 | 0.07 | 0.036 | 2.0 |
| 102 | TP826 | 0.67 | 0.253 | 2.7 |
| 103 | TP827 | 0.133 | 0.081 | 1.6 |
| 104 | TP828 | 0.228 | 0.587 | 0.4 |
| 109 | TP564 | 1.250 | 1.220 | 1.0 |
| 110 | TP575 | 0.595 | 0.866 | 0.7 |
| 111 | TP597 | 0.74 | 0.61 | 1.2 |
| 112 | TP598 | 1.14 | 0.5 | 2.3 |
| 113 | TP604 | 1.09 | 0.47 | 2.3 |
| 114 | TP443 | 0.18 | 0.1 | 1.8 |
| 115 | TP608 | 0.21 | 0.23 | 0.9 |
| 116 | TP609 | 0.36 | 0.42 | 0.9 |
| 117 | TP628 | 0.86 | 1.39 | 0.6 |
| 118 | TP630 | 0.89 | 0.29 | 3.0 |
| 119 | TP640 | 0.69 | 0.84 | 0.8 |
| 120 | TP829 | 1.06 | 0.68 | 1.56 |
| 121 | TP830 | 0.14 | 0.22 | 0.64 |
| 122 | TP831 | 0.14 | 0.08 | 1.66 |

EXAMPLE 4

Diet induced obesity (DIO) mice have long been used as surrogates for humans in the study of the efficacy of anti-obesity compounds. The results obtained from such mice in the study of obesity compounds are translatable to humans (See for example, Nilsson et al. Acta Pharmacologia Sinica 33: 173-181 (2012), which is incorporated herein by reference in its entirety). Thus, DIO mice are useful surrogates for humans for the testing the efficacy of compounds intended to treat obesity.

DIO mice are divided into groups of eight mice per group and the initial average body weight, food intake and basal glucose of each group were matched. Each group of mice is subcutaneously (sc) injected with a single dose of peptide or vehicle control. The administered doses may vary between 3 and 300 nmol/kg. Body weight and food intake are measured daily for four days after the initial dosing. Blood glucose is measured 5 hours post dose, and then daily for four days. A separate set of mice were treated with same dose of each peptide. Serial blood was taken at five hours, 24 hours, 48 hours and 72 hours post sc injection to measure drug exposure.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A GCG/GLP-1 receptor co-agonist peptide comprising the formula $$HX^2QGTFTSX^9X^{10}SLYLDX^{16}RAAX^{20}X^{21}FVX^{24}X^{25}LX^{27}X^{28}TX^{30}\text{-}NH_2$$ (SEQ ID NO: 123)

or a pharmaceutically acceptable salt or counterion thereof, wherein $X^2$ is alpha-aminoisobutyric acid (aib), D-Ser, or alpha-Methyl-L-Serine (alpha-MS);

$X^9$ is Asp, or Glu;

$X^{10}$ is Lys or p-aminomethyl-L-phenylalanine (pAF) conjugated to a fatty acid provided that the amino acid at position 20 or 24 is a Lys conjugated to a fatty diacid, or Tyr;

$X^{16}$ is aib, Ala, Ser, or Glu;

$X^{20}$ is Lys is conjugated to a fatty diacid, pAF conjugated to a fatty diacid, norleucine (Nle) conjugated to a fatty diacid, or Gln;

$X^{21}$ is Lys conjugated to a fatty diacid, pAF conjugated to a fatty diacid, Asp, alpha-methyl-L-phenylalanine (alpha-MF), or alpha-MD;

$X^{24}$ is Gln, Lys conjugated to a fatty diacid, or pAF conjugated to a fatty diacid;

$X^{25}$ is Trp or alpha-methyl-L-tryptophan (alpha-MW);

$X^{27}$ is L-Met sulphone or Leu;

$X^{28}$ is Glu, Asp, alpha-MD, Lys, aib, Ala, Lys conjugated to a fatty diacid or pAF conjugated to a fatty diacid;

$X^{30}$ is absent, or Lys linked at the C-terminus to gamma-Glu when $X^{27}$ is Leu or L-Met-sulphone and $X^{28}$ is Ala, aib, alpha-MD, or Lys conjugated to a fatty diacid;

with the proviso that for each co-agonist peptide only one of $X^{10}$, $X^{20}$, $X^{21}$, $X^{24}$, or $X^{28}$ is conjugated to a fatty diacid; and wherein the GCG/GLP-1 receptor co-agonist peptide comprises at:
1) $X^{10}$ a Lys conjugated to a C16 fatty acid and a Lys at position 20 or 24 conjugated to a fatty diacid;
2) $X^{20}$ a pAF conjugated to a fatty diacid or a Lys conjugated to a fatty diacid;
3) $X^{21}$ a pAF conjugated to a fatty diacid or a Lys conjugated to a fatty diacid;
4) $X^{24}$ a pAF conjugated to a fatty diacid or a Lys conjugated to a fatty diacid; or
5) $X^{28}$ a pAF conjugated to a fatty diacid or a Lys conjugated to a fatty diacid.

2. The GCG/GLP-1 receptor co-agonist peptide of claim 1, wherein the fatty diacid comprises a C14, C15, C16, C17, C18, C19, or C20 fatty diacid.

3. The GCG/GLP-1 receptor co-agonist peptide of claim 1, wherein the GCG/GLP-1 receptor co-agonist peptide comprises the fatty diacid conjugated to Lys or pAF via a gamma-Glu linker.

4. The GCG/GLP-1 receptor co-agonist peptide of claim 1, wherein the GCG/GLP-1 receptor co-agonist peptide comprises the fatty diacid conjugated to Lys or pAF via a $PEG_2PEG_2$-gamma-Glu linker wherein $PEG_2$ is 8-amino-3,6-dioxaoctanoic acid.

5. The GCG/GLP-1 receptor co-agonist peptide of claim 1, wherein the GCG/GLP-1 receptor co-agonist peptide comprises at $X^{10}$ a pAF conjugated to a fatty diacid.

6. The GCG/GLP-1 receptor co-agonist peptide of claim 1, wherein the GCG/GLP-1 receptor co-agonist peptide has activity at the glucagon receptor and the GLP-1 receptor.

7. A composition comprising one or more of the GCG/GLP-1 receptor co-agonist peptides of claim 1, or pharmaceutically acceptable salt thereof, and a pharmaceutically acceptable carrier.

8. A method for treating a patient for a metabolic disease or disorder comprising administering to a patient in need thereof an effective amount of one or more of the GCG/GLP-1 receptor co-agonist peptides of claim 1 to treat the metabolic disease or disorder in the patient, wherein the metabolic disease or disorder comprises diabetes, non-alcoholic fatty liver disease (NAFLD), non-alcoholic steatohepatitis (NASH), or obesity.

9. The method of claim 8, wherein the diabetes comprises Type I diabetes, Type II diabetes, or gestational diabetes.

10. The method of claim 8, wherein the patient has more than one metabolic disease or disorder.

11. The method of claim 8, wherein the metabolic disease or disorder comprises (i) diabetes and NASH, NAFLD, or obesity; (ii) obesity and NASH or NAFLD; (iii) diabetes, NASH, and obesity; (iv) diabetes, NAFLD, and obesity; or (v) diabetes and obesity.

12. A method for treating a patient for a metabolic disease or disorder comprising administering to the patient in need thereof an effective amount of the composition of claim 7 to treat the metabolic disease or disorder in the patient, wherein the metabolic disease or disorder comprises diabetes, non-alcoholic fatty liver disease (NAFLD), non-alcoholic steatohepatitis (NASH), or obesity.

13. The method of claim 12, wherein the patient has more than one metabolic disease or disorder.

14. The method of claim 12, wherein the metabolic disease or disorder comprises (i) diabetes and NASH, NAFLD, or obesity; (ii) obesity and NASH or NAFLD; (iii) diabetes, NASH, and obesity; (iv) diabetes, NAFLD, and obesity; or (v) diabetes and obesity.

15. A method for treating a metabolic disease or disorder in a patient or individual comprising administering to the patient or individual in need thereof an effective amount of a composition comprising a co-agonist peptide agonist of claim 1 and administering to the patient or individual an effective amount of a composition comprising an insulin or insulin analog to treat the metabolic disease or disorder in the patient or individual wherein the metabolic disease or disorder comprises diabetes, non-alcoholic fatty liver disease (NAFLD), non-alcoholic steatohepatitis (NASH), or obesity.

16. The method of claim 15, wherein the insulin analog comprises insulin detemir, insulin glargine, insulin glulisine, insulin degludec, or insulin lispro.

17. The method of claim 15, wherein the diabetes comprises Type I diabetes, Type II diabetes, or gestational diabetes.

18. The method of claim 15, wherein the patient has more than one metabolic disease or disorder selected from (i) diabetes and NASH, NAFLD, or obesity; (ii) obesity and NASH or NAFLD; (iii) diabetes, NASH, and obesity; (iv) diabetes, NAFLD, and obesity; or (v) diabetes and obesity.

19. A GCG/GLP-1 receptor co-agonist peptide comprising the formula

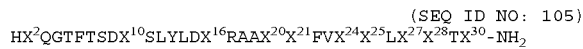
(SEQ ID NO: 105)
HX²QGTFTSDX¹⁰SLYLDX¹⁶RAAX²⁰X²¹FVX²⁴X²⁵LX²⁷X²⁸TX³⁰-NH₂ wherein
X² is alpha-aminoisobutyric acid (aib), D-Ser, or alpha-Methyl-L-Serine (alpha-MS);
X⁹ is Asp or alpha-Methyl-L-Aspartic acid (alpha-MD);
X¹⁰ is Lys or p-aminomethyl-L-phenylalanine (pAF) conjugated to a fatty acid provided that the amino acid at position 20 or 24 is a Lys conjugated to a fatty diacid, or Tyr;
X¹⁶ is aib, Ala, Ser, or Glu;
X²⁰ is Lys is conjugated to a fatty diacid, pAF conjugated to a fatty diacid, norleucine (Nle) conjugated to a fatty diacid, or Gln;
X²¹ is Lys conjugated to a fatty diacid or pAF conjugated to a fatty diacid, Asp, alpha-methyl-L-phenylalanine (alpha-MF), or alpha-MD;
X²⁴ is Gln, Lys conjugated to a fatty diacid, or pAF conjugated to a fatty diacid;
X²⁵ is Trp or alpha-methyl-L-tryptophan (alpha-MW);
X²⁷ is L-Met sulphone or Leu;
X²⁸ is Glu, Asp, alpha-MD, Lys, aib, Ala, Lys conjugated to a fatty diacid or pAF conjugated to a fatty diacid; and
X³⁰ is absent or Lys linked at the C-terminus to gamma-Glu when X²⁷ is Leu or L-Met-sulphone and X²⁸ is Ala, aib, alpha-MD, or Lys conjugated to a fatty diacid;
with the proviso that for each co-agonist peptide, only one of X¹⁰, X²⁰, X²¹, X²⁴, or X²⁸ is conjugated to a fatty diacid.

20. A GCG/GLP-1 receptor co-agonist peptide wherein the GCG/GLP-1 receptor co-agonist peptide is selected from the group consisting of SEQ ID No. NO: 1, SEQ ID NO: 2, SEQ ID NO: 3, SEQ ID NO: 4, SEQ ID NO: 5, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 48, SEQ ID NO: 49, SEQ ID NO: 50, SEQ ID NO: 51, SEQ ID NO: 52, SEQ ID NO: 54, SEQ ID NO: 55, SEQ ID NO: 56, SEQ ID NO: 57, SEQ ID NO: 58, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, and SEQ ID NO: 104, or a pharmaceutically acceptable salt or counterion thereof.

21. A GCG/GLP-1 receptor co-agonist peptide wherein the GCG/GLP-1 receptor co-agonist peptide is selected from the group consisting of SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID No. NO: SEQ ID NO: 41, SEQ ID NO: 42, SEQ ID NO: 43, SEQ ID NO: 44, SEQ ID NO: 45, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, and SEQ ID NO: 104, or a pharmaceutically acceptable salt or counterion thereof.

22. A GCG/GLP-1 receptor co-agonist peptide comprising the formula

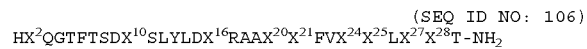
(SEQ ID NO: 106)
HX²QGTFTSDX¹⁰SLYLDX¹⁶RAAX²⁰X²¹FVX²⁴X²⁵LX²⁷X²⁸T-NH₂ wherein
X² is alpha-aminoisobutyric acid (aib), D-Ser, or alpha-Methyl-L-Serine (alpha-MS);
X⁹ is Asp or alpha-Methyl-L-Aspartic acid (alpha-MD);
X¹⁰ is Lys or p-aminomethyl-L-phenylalanine (pAF) conjugated to a fatty acid provided that the amino acid at position 20 or 24 is a Lys conjugated to a fatty diacid, or Tyr;
X¹⁶ is aib, Ala, Ser, or Glu;
X²⁰ is Lys is conjugated to a fatty diacid, pAF conjugated to a fatty diacid, norleucine (Nle) conjugated to a fatty diacid, or Gln;
X²¹ is Lys conjugated to a fatty diacid, pAF conjugated to a fatty diacid, Asp, alpha-methyl-L-phenylalanine (alpha-MF), or alpha-MD;

$X^{24}$ is Gln, Lys conjugated to a fatty diacid, or pAF conjugated to a fatty diacid;

$X^{25}$ is Trp or alpha-methyl-L-tryptophan (alpha-MW);

$X^{27}$ is L-Met sulphone or Leu; and $X^{28}$ is Glu, Asp, alpha-MD, Lys, aib, Ala, Lys conjugated to a fatty diacid or pAF conjugated to a fatty diacid;

with the proviso that for each co-agonist peptide only one of $X^{10}$, $X^{20}$, $X^{21}$, $X^{24}$, or $X^{28}$ is conjugated to a fatty diacid.

23. A GCG/GLP-1 receptor co-agonist peptide comprising the formula

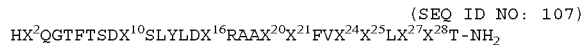
(SEQ ID NO: 107)
$HX^2QGTFTSDX^{10}SLYLDX^{16}RAAX^{20}X^{21}FVX^{24}X^{25}LX^{27}X^{28}T-NH_2$ wherein $X^2$ is alpha-aminoisobutyric acid (aib);

$X^9$ is Asp or alpha-Methyl-L-Aspartic acid (alpha-MD);

$X^{10}$ is Lys or p-aminomethyl-L-phenylalanine (pAF) conjugated to a fatty acid provided that the amino acid at position 20 or 24 is a Lys conjugated to a fatty diacid, or Tyr;

$X^{16}$ is aib, Ala, Ser, or Glu;

$X^{20}$ is Lys is conjugated to a fatty diacid, pAF conjugated to a fatty diacid, norleucine (Nle) conjugated to a fatty diacid, or Gln;

$X^{21}$ is Lys conjugated to a fatty diacid, pAF conjugated to a fatty diacid, Asp, alpha-methyl-L-phenylalanine (alpha-MF), or alpha-MD;

$X^{24}$ is Gln, Lys conjugated to a fatty diacid, or pAF conjugated to a fatty diacid;

$X^{25}$ is Trp or alpha-methyl-L-tryptophan (alpha-MW);

$X^{27}$ is L-Met sulphone or Leucine;

$X^{28}$ is Glu, Asp, alpha-MD, Lys, aib, Ala, Lys conjugated to a fatty diacid or pAF conjugated to a fatty diacid; and $X^{30}$ is absent or Lys linked at the C-terminus to gamma-Glu when $X^{27}$ is Leu or L-Met-sulphone, and $X^{28}$ is Ala, aib, alpha-MD, or Lys conjugated to a fatty diacid;

with the proviso that for each co-agonist peptide, only one of $X^{10}$, $X^{20}$, $X^{21}$, $X^{24}$, or $X^{28}$ is conjugated to a fatty diacid and excludes peptides disclosed in Table 1 of WO2017074798.

24. A GCG/GLP-1 receptor co-agonist peptide wherein the GCG/GLP-1 receptor co-agonist peptide is selected from the group consisting of SEQ ID NO: 46, SEQ ID NO: 59, SEQ ID NO: 60, SEQ ID NO: 61, SEQ ID NO: 62, SEQ ID NO: 63, SEQ ID NO: 120, SEQ ID NO: 121, and SEQ ID NO: 122.

* * * * *

SEQUENCE LISTING

<160> NUMBER OF SEQ ID NOS: 127

<210> SEQ ID NO 1
<211> LENGTH: 29
<212> TYPE: PRT
<213> ORGANISM: Artificial Sequence -continued

```
<220> FEATURE:
<223> OTHER INFORMATION: peptide TP565
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-EC20-OH)
<220> FEATURE:
<221> NAME/KEY: MISC_FEATURE
<222> LOCATION: (27)..(27)
<223> OTHER INFORMATION: Xaa is Lys(PEG2PEG2-gammaGlu-EC20-OH)
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 1

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: peptide TP579
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (28)..(28)
<223> OTHER INFORMATION: Xaa is alpha-aminoisobutyric acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 2

His Xaa Gln Gly Thr Phe Thr Ser Asp Tyr Ser Lys Tyr Leu Glu Xaa
1               5                   10                  15

Arg Ala Ala Xaa Asp Phe Val Gln Trp Leu Leu Xaa Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: peptide TP583
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
```

```
<221> NAME/KEY: MISC_FEATURE
<222> LOCATION: (24)..(24)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 3

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Leu Asp Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: peptide TP584
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is alpha-aminoisobutyric acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 4

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Leu Asp Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: peptide TP578
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa isC-terminal amide

<400> SEQUENCE: 5

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
```

```
              20                  25

<210> SEQ ID NO 6
<211> LENGTH: 29
<212> TYPE: PRT
<213> ORGANISM: Artificial Sequence
<220> FEATURE:
<223> OTHER INFORMATION: peptide TP580
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 6

His Xaa Gln Gly Thr Phe Thr Ser Asp Xaa Ser Lys Tyr Leu Asp Ala
 1               5                  10                  15

Arg Ala Ala Gln Asp Phe Val Gln Trp Leu Xaa Asp Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: peptide TP581
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-EC20-OH)
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 7

His Xaa Gln Gly Thr Phe Thr Ser Asp Xaa Ser Lys Tyr Leu Asp Xaa
 1               5                  10                  15

Arg Ala Ala Gln Asp Phe Val Gln Trp Leu Leu Ala Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: peptide TP582
<220> FEATURE:
<221> NAME/KEY: MISC_FEATURE
<222> LOCATION: (2)..(2)
<223> OTHER INFORMATION: Xaa is alpha-aminoisobutyric acid
```

```
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C20-OH)
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 8

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Leu Ala Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: peptide TP585
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is p-aminomethyl-L-phenylalanine(PEG2PEG2-
      gammaGlu-C20-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 9

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: peptide TP588
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
```

```
<221> NAME/KEY: MISC_FEATURE
<222> LOCATION: (29)..(29)
<223> OTHER INFORMATION: Xaa is C-terminal amide

<400> SEQUENCE: 10

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Xaa Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: peptide TP589
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-EC20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 11

His Xaa Gln Gly Thr Phe Thr Ser Asp Tyr Ser Lys Tyr Leu Asp Glu
1               5                   10                  15

Arg Ala Ala Xaa Asp Phe Val Gln Trp Leu Xaa Xaa Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: peptide TP590
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (22)..(22)
<223> OTHER INFORMATION: Xaa is alpha-Methyl-L-phenylalanine
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 12

His Xaa Gln Gly Thr Phe Thr Ser Asp Tyr Ser Lys Tyr Leu Asp Ala
```

Arg Ala Ala Xaa Asp Xaa Val Gln Trp Leu Xaa Asp Thr
            20              25

<210> SEQ ID NO 13
<211> LENGTH: 29
<212> TYPE: PRT
<213> ORGANISM: Artificial Sequence
<220> FEATURE:
<223> OTHER INFORMATION: peptide TP592
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-EC20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 13

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
            20              25

<210> SEQ ID NO 14
<211> LENGTH: 29
<212> TYPE: PRT
<213> ORGANISM: Artificial Sequence
<220> FEATURE:
<223> OTHER INFORMATION: peptide TP594
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (21)..(21)
<223> OTHER INFORMATION: Xaa is alpha-Methyl-L-Aspartic acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 14

His Xaa Gln Gly Thr Phe Thr Ser Asp Tyr Ser Lys Tyr Leu Asp Ala
1               5                   10                  15

Arg Ala Ala Xaa Xaa Phe Val Gln Trp Leu Xaa Asp Thr
            20              25

<210> SEQ ID NO 15

```
<211> LENGTH: 29
<212> TYPE: PRT
<213> ORGANISM: Artificial Sequence
<220> FEATURE:
<223> OTHER INFORMATION: peptide TP576
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 15

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Asp Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: peptide TP577
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 16

His Xaa Gln Gly Thr Phe Thr Ser Asp Tyr Ser Lys Tyr Leu Asp Ser
1               5                   10                  15

Arg Ala Ala Xaa Asp Phe Val Gln Trp Leu Xaa Asp Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: peptide TP586
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
```

```
<222> LOCATION: (20)..(20)
<223> OTHER INFORMATION: Xaa is p-aminomethyl-L-phenylalanine(PEG2PEG2-
      gammaGlu-C20-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 17

His Xaa Gln Gly Thr Phe Thr Ser Asp Tyr Ser Lys Tyr Leu Asp Glu
1               5                   10                  15

Arg Ala Ala Xaa Asp Phe Val Gln Trp Leu Leu Lys Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: peptide TP587
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 18

His Xaa Gln Gly Thr Phe Thr Ser Asp Tyr Ser Lys Tyr Leu Asp Glu
1               5                   10                  15

Arg Ala Ala Xaa Asp Phe Val Gln Trp Leu Leu Lys Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: peptide TP591
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (22)..(22)
<223> OTHER INFORMATION: Xaa is alpha-Methyl-L-phenylalanine
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 19
```

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: peptide TP593
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 20

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: peptide TP595
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 21

His Xaa Gln Gly Thr Phe Phe Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 22
<211> LENGTH: 29
<212> TYPE: PRT
<213> ORGANISM: Artificial Sequence

```
<220> FEATURE:
<223> OTHER INFORMATION: peptide TP596
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 22

His Xaa Gln Gly Thr Phe Leu Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 23
<211> LENGTH: 29
<212> TYPE: PRT
<213> ORGANISM: Artificial Sequence
<220> FEATURE:
<223> OTHER INFORMATION: peptide TP599
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 23

His Xaa Gln Gly Thr Phe Thr Ser Asp Tyr Ser Lys Tyr Leu Asp Ala
1               5                   10                  15

Leu Ala Ala Xaa Asp Phe Val Gln Trp Leu Xaa Asp Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: peptide TP600
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
```

```
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 24

His Xaa Gln Gly Thr Phe Thr Ser Asp Xaa Ser Lys Tyr Leu Asp Ala
1               5                   10                  15

Arg Ala Ala Xaa Asp Phe Val Gln Trp Leu Xaa Asp Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: peptide TP601
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is Lys(gammaGlu-gammaGlu-C16)
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa isC-terminal amide

<400> SEQUENCE: 25

His Xaa Gln Gly Thr Phe Thr Ser Asp Xaa Ser Lys Tyr Leu Asp Ala
1               5                   10                  15

Arg Ala Ala Xaa Asp Phe Val Gln Trp Leu Xaa Asp Thr
            20                  25

<210> SEQ ID NO 26
<211> LENGTH: 29
<212> TYPE: PRT
<213> ORGANISM: Artificial Sequence
<220> FEATURE:
<223> OTHER INFORMATION: peptide TP602
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is Lys(PEG2PEG2-gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 26

His Xaa Gln Gly Thr Phe Thr Ser Asp Tyr Ser Lys Tyr Leu Asp Ala
```

```
1               5                   10                  15
Arg Ala Ala Gln Asp Phe Val Gln Trp Leu Xaa Xaa Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: peptide TP603
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is Lys(PEG2PEG2-gammaGlu-EC20-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 27

His Xaa Gln Gly Thr Phe Thr Ser Asp Tyr Ser Lys Tyr Leu Asp Ala
1               5                   10                  15

Arg Ala Ala Gln Asp Phe Val Gln Trp Leu Xaa Xaa Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: peptide TP605
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is p-aminomethyl-L-phenylalanine(PEG2PEG2-
      gammaGlu-C20-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 28

His Xaa Gln Gly Thr Phe Thr Ser Asp Tyr Ser Lys Tyr Leu Asp Ala
1               5                   10                  15

Arg Ala Ala Gln Asp Phe Val Gln Trp Leu Xaa Xaa Thr
            20                  25

<210> SEQ ID NO 29
<211> LENGTH: 29
<212> TYPE: PRT
<213> ORGANISM: Artificial Sequence
<220> FEATURE:
<223> OTHER INFORMATION: peptide TP606
<220> FEATURE:
<221> NAME/KEY: MISC_FEATURE
```

```
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is Lys(gammaGlu-gammaGlu-C16)
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 29

His Xaa Gln Gly Thr Phe Thr Ser Asp Xaa Ser Lys Tyr Leu Asp Ala
 1               5                  10                  15

Arg Ala Ala Xaa Asp Phe Val Gln Trp Leu Xaa Asp Thr
                20                  25

<210> SEQ ID NO 30
<211> LENGTH: 29
<212> TYPE: PRT
<213> ORGANISM: Artificial Sequence
<220> FEATURE:
<223> OTHER INFORMATION: peptide TP607
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is Lys(gammaGlu-gammaGlu-C16)
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 30

His Xaa Gln Gly Thr Phe Thr Ser Asp Xaa Ser Lys Tyr Leu Asp Ala
 1               5                  10                  15

Arg Ala Ala Gln Asp Phe Val Xaa Trp Leu Xaa Xaa Thr
                20                  25

<210> SEQ ID NO 31
<211> LENGTH: 29
<212> TYPE: PRT
<213> ORGANISM: Artificial Sequence
<220> FEATURE:
<223> OTHER INFORMATION: peptide TP610
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
```

```
<221> NAME/KEY: MISC_FEATURE
<222> LOCATION: (15)..(15)
<223> OTHER INFORMATION: Xaa is alpha-Methyl-L-Aspartic acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 31

His Xaa Gln Gly Thr Phe Thr Ser Asp Tyr Ser Lys Tyr Leu Xaa Ala
1               5                   10                  15

Arg Ala Ala Xaa Asp Phe Val Gln Trp Leu Xaa Xaa Thr
            20                  25

<210> SEQ ID NO 32
<211> LENGTH: 29
<212> TYPE: PRT
<213> ORGANISM: Artificial Sequence
<220> FEATURE:
<223> OTHER INFORMATION: peptide TP611
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (21)..(21)
<223> OTHER INFORMATION: Xaa is alpha-Methyl-L-Aspartic acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 32

His Xaa Gln Gly Thr Phe Thr Ser Asp Tyr Ser Lys Tyr Leu Asp Ala
1               5                   10                  15

Arg Ala Ala Xaa Xaa Phe Val Gln Trp Leu Xaa Xaa Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: peptide TP612
<220> FEATURE:
<221> NAME/KEY: MISC_FEATURE
<222> LOCATION: (2)..(2)
<223> OTHER INFORMATION: Xaa is alpha-aminoisobutyric acid
```

```
<220> FEATURE:
<221> NAME/KEY: MISC_FEATURE
<222> LOCATION: (15)..(15)
<223> OTHER INFORMATION: Xaa is alpha-Methyl-L-Aspartic acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (21)..(21)
<223> OTHER INFORMATION: Xaa is alpha-Methyl-L-Aspartic acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 33

His Xaa Gln Gly Thr Phe Thr Ser Asp Tyr Ser Lys Tyr Leu Xaa Ala
1               5                   10                  15

Arg Ala Ala Xaa Xaa Phe Val Gln Trp Leu Xaa Xaa Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: peptide TP613
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 34

His Xaa Gln Gly Thr Phe Thr Ser Asp Tyr Ser Lys Tyr Leu Asp Glu
1               5                   10                  15

Arg Ala Ala Xaa Asp Phe Val Gln Trp Leu Xaa Xaa Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: peptide TP614
<220> FEATURE:
<221> NAME/KEY: MISC_FEATURE
<222> LOCATION: (2)..(2)
```

```
<223> OTHER INFORMATION: Xaa is alpha-Methyl-L-serine
<220> FEATURE:
<221> NAME/KEY: MISC_FEATURE
<222> LOCATION: (20)..(20)
<223> OTHER INFORMATION: Xaa is Lys(PEG2PEG2-gammaGlu-EC16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 35

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: peptide TP615
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (21)..(21)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 36

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 37
<211> LENGTH: 29
<212> TYPE: PRT
<213> ORGANISM: Artificial Sequence
<220> FEATURE:
<223> OTHER INFORMATION: peptide TP616
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
```

```
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 37

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 38
<211> LENGTH: 29
<212> TYPE: PRT
<213> ORGANISM: Artificial Sequence
<220> FEATURE:
<223> OTHER INFORMATION: peptide TP617
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (21)..(21)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 38

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 39
<211> LENGTH: 29
<212> TYPE: PRT
<213> ORGANISM: Artificial Sequence
<220> FEATURE:
<223> OTHER INFORMATION: peptide TP618
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
```

```
<221> NAME/KEY: MISC_FEATURE
<222> LOCATION: (28)..(28)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 39

His Xaa Gln Gly Thr Phe Thr Ser Asp Tyr Ser Lys Tyr Leu Asp Xaa
 1               5                  10                  15

Arg Ala Ala Xaa Asp Phe Val Gln Trp Leu Xaa Xaa Thr
            20                  25

<210> SEQ ID NO 40
<211> LENGTH: 29
<212> TYPE: PRT
<213> ORGANISM: Artificial Sequence
<220> FEATURE:
<223> OTHER INFORMATION: peptide TP619
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 40

His Xaa Gln Gly Thr Phe Thr Ser Asp Tyr Ser Lys Tyr Leu Asp Xaa
 1               5                  10                  15

Arg Ala Ala Gln Xaa Phe Val Gln Trp Leu Xaa Xaa Thr
            20                  25

<210> SEQ ID NO 41
<211> LENGTH: 29
<212> TYPE: PRT
<213> ORGANISM: Artificial Sequence
<220> FEATURE:
<223> OTHER INFORMATION: peptide TP620
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
```

```
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 41

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Xaa Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: peptide TP621
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 42

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Xaa Xaa Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: peptide TP622
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2-
      gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
```

```
<222> LOCATION: (29)..(29)
<223> OTHER INFORMATION: Xaa is C-terminal amide

<400> SEQUENCE: 43

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Asp Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: peptide TP623
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (20)..(10)
<223> OTHER INFORMATION: Xaa is p-aminomethyl-L-phenylalanine(PEG2-
      gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 44

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Asp Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: peptide TP624
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 45
```

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Xaa Thr
            20                  25

<210> SEQ ID NO 46
<211> LENGTH: 29
<212> TYPE: PRT
<213> ORGANISM: Artificial Sequence
<220> FEATURE:
<223> OTHER INFORMATION: peptide TP625
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (25)..(25)
<223> OTHER INFORMATION: Xaa is alpha-methyl-L-tryptophan
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 46

His Xaa Gln Gly Thr Phe Thr Ser Asp Xaa Ser Lys Tyr Leu Asp Ala
1               5                   10                  15

Arg Ala Ala Gln Asp Phe Val Gln Xaa Leu Xaa Asp Thr
            20                  25

<210> SEQ ID NO 47
<211> LENGTH: 29
<212> TYPE: PRT
<213> ORGANISM: Artificial Sequence
<220> FEATURE:
<223> OTHER INFORMATION: peptide TP626
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 47

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 48
<211> LENGTH: 29
<212> TYPE: PRT

```
<213> ORGANISM: Artificial Sequence
<220> FEATURE:
<223> OTHER INFORMATION: peptide TP627
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (2)..(2)
<223> OTHER INFORMATION: Xaa is Lys(PEG2-gammaGlu-C16-OH)
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 48

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 49
<211> LENGTH: 29
<212> TYPE: PRT
<213> ORGANISM: Artificial Sequence
<220> FEATURE:
<223> OTHER INFORMATION: peptide TP629
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2-gammaGlu-C20-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 49

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 50
<211> LENGTH: 29
<212> TYPE: PRT
<213> ORGANISM: Artificial Sequence
<220> FEATURE:
<223> OTHER INFORMATION: peptide TP631
```

```
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (25)..(25)
<223> OTHER INFORMATION: Xaa is alpha-methyl-L-tryptophan
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 50

His Xaa Gln Gly Thr Phe Thr Ser Asp Tyr Ser Lys Tyr Leu Asp Ala
1               5                   10                  15

Arg Ala Ala Xaa Asp Phe Val Gln Xaa Leu Xaa Asp Thr
            20                  25

<210> SEQ ID NO 51
<211> LENGTH: 29
<212> TYPE: PRT
<213> ORGANISM: Artificial Sequence
<220> FEATURE:
<223> OTHER INFORMATION: peptide TP632
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (25)..(25)
<223> OTHER INFORMATION: Xaa is alpha-methyl-L-tryptophan
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 51

His Xaa Gln Gly Thr Phe Thr Ser Asp Tyr Ser Lys Tyr Leu Asp Ala
1               5                   10                  15

Arg Ala Ala Xaa Asp Phe Val Gln Xaa Leu Xaa Xaa Thr
            20                  25

<210> SEQ ID NO 52
<211> LENGTH: 29
<212> TYPE: PRT
<213> ORGANISM: Artificial Sequence
<220> FEATURE:
<223> OTHER INFORMATION: peptide TP633
<220> FEATURE:
<221> NAME/KEY: MISC_FEATURE
<222> LOCATION: (2)..(2)
```

```
<223> OTHER INFORMATION: Xaa is p-aminomethyl-L-phenylalanine(PEG2-
      gammaGlu-C18-OH
<220> FEATURE:
<221> NAME/KEY: MISC_FEATURE
<222> LOCATION: (21)..(21)
<223> OTHER INFORMATION: Xaa is p-aminomethyl-L-phenylalanine(PEG2-
      gammaGlu-C18-OH
<220> FEATURE:
<221> NAME/KEY: MISC_FEATURE
<222> LOCATION: (29)..(29)
<223> OTHER INFORMATION: Xaa is C-terminal amide

<400> SEQUENCE: 52

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 53
<211> LENGTH: 29
<212> TYPE: PRT
<213> ORGANISM: Artificial Sequence
<220> FEATURE:
<223> OTHER INFORMATION: peptide TP634
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 53

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 54
<211> LENGTH: 29
<212> TYPE: PRT
<213> ORGANISM: Artificial Sequence
<220> FEATURE:
<223> OTHER INFORMATION: peptide TP635
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is p-aminomethyl-L-phenylalanine(PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 54
```

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Leu Asp Thr
            20                  25

<210> SEQ ID NO 55
<211> LENGTH: 29
<212> TYPE: PRT
<213> ORGANISM: Artificial Sequence
<220> FEATURE:
<223> OTHER INFORMATION: peptide TP636
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 55

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 56
<211> LENGTH: 29
<212> TYPE: PRT
<213> ORGANISM: Artificial Sequence
<220> FEATURE:
<223> OTHER INFORMATION: peptide TP637
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 56

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Xaa Asp Thr
            20                  25

<210> SEQ ID NO 57
<211> LENGTH: 29

```
<212> TYPE: PRT
<213> ORGANISM: Artificial Sequence
<220> FEATURE:
<223> OTHER INFORMATION: peptide TP638
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is p-aminomethyl-L-phenylalanine(PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 57

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Leu Asp Thr
            20                  25

<210> SEQ ID NO 58
<211> LENGTH: 29
<212> TYPE: PRT
<213> ORGANISM: Artificial Sequence
<220> FEATURE:
<223> OTHER INFORMATION: peptide TP639
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is p-aminomethyl-L-phenylalanine(gammaGlu-
      C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 58

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Leu Asp Thr
            20                  25

<210> SEQ ID NO 59
<211> LENGTH: 29
<212> TYPE: PRT
<213> ORGANISM: Artificial Sequence
<220> FEATURE:
<223> OTHER INFORMATION: peptide TP657
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16-OH)
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa is alpha-Methyl-L-Aspartic acid
```

```
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 59

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Leu Xaa Xaa
            20                  25

<210> SEQ ID NO 60
<211> LENGTH: 29
<212> TYPE: PRT
<213> ORGANISM: Artificial Sequence
<220> FEATURE:
<223> OTHER INFORMATION: peptide TP658
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16-OH)
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 60

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Xaa Ala Xaa
            20                  25

<210> SEQ ID NO 61
<211> LENGTH: 29
<212> TYPE: PRT
<213> ORGANISM: Artificial Sequence
<220> FEATURE:
<223> OTHER INFORMATION: peptide TP659
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16OH)
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 61

His Xaa Gln Gly Thr Phe Thr Ser Asp Xaa Ser Lys Tyr Leu Asp Xaa
1               5                   10                  15
```

-continued

```
Arg Ala Ala Gln Asp Phe Val Gln Trp Leu Leu Ala Xaa
            20                  25

<210> SEQ ID NO 62
<211> LENGTH: 29
<212> TYPE: PRT
<213> ORGANISM: Artificial Sequence
<220> FEATURE:
<223> OTHER INFORMATION: peptide TP660
<220> FEATURE:
<221> NAME/KEY: MISC_FEATURE
<222> LOCATION: (2)..(2)
<223> OTHER INFORMATION: Xaa is alpha-Methyl-L-serine
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16-OH)
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 62

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Leu Ala Xaa
            20                  25

<210> SEQ ID NO 63
<211> LENGTH: 29
<212> TYPE: PRT
<213> ORGANISM: Artificial Sequence
<220> FEATURE:
<223> OTHER INFORMATION: peptide TP661
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16-OH)
<220> FEATURE:
<221> NAME/KEY: MISC_FEATURE
<222> LOCATION: (10)..(10)
<223> OTHER INFORMATION: Xaa is p-aminomethyl-L-phenylalanine(PEG2PEG2-
      gammaGlu-C16-OH)
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 63

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Leu Ala Xaa
            20                  25

<210> SEQ ID NO 64
<211> LENGTH: 29
<212> TYPE: PRT
```

```
<213> ORGANISM: Artificial Sequence
<220> FEATURE:
<223> OTHER INFORMATION: peptide TP662
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 64

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Leu Ala Xaa
            20                  25

<210> SEQ ID NO 65
<211> LENGTH: 29
<212> TYPE: PRT
<213> ORGANISM: Artificial Sequence
<220> FEATURE:
<223> OTHER INFORMATION: peptide TP663
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is p-aminomethyl-L-phenylalanine(PEG2PEG2-
      gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 65

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Leu Ala Xaa
            20                  25

<210> SEQ ID NO 66
<211> LENGTH: 29
<212> TYPE: PRT
<213> ORGANISM: Artificial Sequence
<220> FEATURE:
<223> OTHER INFORMATION: peptide TP664
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (21)..(21)
```

```
<223> OTHER INFORMATION: Xaa is Lys(PEG2PEG2-gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 66

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Leu Ala Xaa
            20                  25

<210> SEQ ID NO 67
<211> LENGTH: 29
<212> TYPE: PRT
<213> ORGANISM: Artificial Sequence
<220> FEATURE:
<223> OTHER INFORMATION: peptide TP665
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is p-aminomethyl-L-phenylalanine(PEG2PEG2-
      gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 67

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Leu Ala Xaa
            20                  25

<210> SEQ ID NO 68
<211> LENGTH: 29
<212> TYPE: PRT
<213> ORGANISM: Artificial Sequence
<220> FEATURE:
<223> OTHER INFORMATION: peptide TP666
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 68

His Xaa Gln Gly Thr Phe Thr Ser Asp Tyr Ser Lys Tyr Leu Asp Xaa
1               5                   10                  15

Arg Ala Ala Gln Phe Val Gln Xaa Trp Leu Leu Ala Xaa
            20                  25
```

<210> SEQ ID NO 69
<211> LENGTH: 29
<212> TYPE: PRT
<213> ORGANISM: Artificial Sequence
<220> FEATURE:
<223> OTHER INFORMATION: peptide TP667
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is p-aminomethyl-L-phenylalanine(PEG2PEG2-
    gammaGlu-C16-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 69

His Xaa Gln Gly Thr Phe Thr Ser Asp Tyr Ser Lys Tyr Leu Asp Xaa
1               5                   10                  15

Arg Ala Ala Gln Phe Val Gln Xaa Trp Leu Leu Ala Xaa
            20                  25

<210> SEQ ID NO 70
<211> LENGTH: 29
<212> TYPE: PRT
<213> ORGANISM: Artificial Sequence
<220> FEATURE:
<223> OTHER INFORMATION: peptide TP672
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 70

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Glu Thr
            20                  25

<210> SEQ ID NO 71
<211> LENGTH: 29
<212> TYPE: PRT
<213> ORGANISM: Artificial Sequence
<220> FEATURE:
<223> OTHER INFORMATION: peptide TP673
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)

<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 71

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Glu Thr
            20                  25

<210> SEQ ID NO 72
<211> LENGTH: 29
<212> TYPE: PRT
<213> ORGANISM: Artificial Sequence
<220> FEATURE:
<223> OTHER INFORMATION: peptide TP674
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 72

His Xaa Gln Gly Thr Phe Thr Ser Asp Tyr Ser Lys Tyr Leu Glu Ala
1               5                   10                  15

Arg Ala Ala Xaa Asp Phe Val Gln Trp Leu Xaa Asp Thr
            20                  25

<210> SEQ ID NO 73
<211> LENGTH: 29
<212> TYPE: PRT
<213> ORGANISM: Artificial Sequence
<220> FEATURE:
<223> OTHER INFORMATION: peptide TP675
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 73

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Glu Thr
            20                  25

<210> SEQ ID NO 74
<211> LENGTH: 29
<212> TYPE: PRT
<213> ORGANISM: Artificial Sequence
<220> FEATURE:
<223> OTHER INFORMATION: peptide TP676
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 74

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 75
<211> LENGTH: 29
<212> TYPE: PRT
<213> ORGANISM: Artificial Sequence
<220> FEATURE:
<223> OTHER INFORMATION: peptide TP677
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 75

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

```
<210> SEQ ID NO 76
<211> LENGTH: 29
<212> TYPE: PRT
<213> ORGANISM: Artificial Sequence
<220> FEATURE:
<223> OTHER INFORMATION: peptide TP678
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is
      p-aminomethyl-L-phenylalanine(PEG2PEG2PEG2-gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 76

His Xaa Gln Gly Thr Phe Thr Ser Asp Tyr Ser Lys Tyr Leu Asp Ala
1               5                  10                  15

Arg Ala Ala Xaa Asp Phe Val Gln Trp Leu Leu Asp Thr
            20                  25

<210> SEQ ID NO 77
<211> LENGTH: 29
<212> TYPE: PRT
<213> ORGANISM: Artificial Sequence
<220> FEATURE:
<223> OTHER INFORMATION: peptide TP679
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is
      p-aminomethyl-L-phenylalanine(PEG2PEG2PEG2-gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 77

His Xaa Gln Gly Thr Phe Thr Ser Asp Tyr Ser Lys Tyr Leu Asp Ala
1               5                  10                  15

Arg Ala Ala Gln Xaa Phe Val Gln Trp Leu Leu Asp Thr
            20                  25

<210> SEQ ID NO 78
<211> LENGTH: 29
<212> TYPE: PRT
<213> ORGANISM: Artificial Sequence
<220> FEATURE:
<223> OTHER INFORMATION: peptide TP680
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
```

```
<222> LOCATION: (29)..(29)
<223> OTHER INFORMATION: Xaa is C-terminal amide

<400> SEQUENCE: 78

His Xaa Gln Gly Thr Phe Thr Ser Asp Tyr Ser Lys Tyr Leu Asp Ala
1               5                   10                  15

Arg Ala Ala Gln Asp Phe Val Xaa Trp Leu Xaa Asp Thr
            20                  25

<210> SEQ ID NO 79
<211> LENGTH: 29
<212> TYPE: PRT
<213> ORGANISM: Artificial Sequence
<220> FEATURE:
<223> OTHER INFORMATION: peptide TP681
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 79

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 80
<211> LENGTH: 29
<212> TYPE: PRT
<213> ORGANISM: Artificial Sequence
<220> FEATURE:
<223> OTHER INFORMATION: peptide TP682
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (28)..(28)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 80

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Leu Xaa Xaa
            20                  25
```

```
<210> SEQ ID NO 81
<211> LENGTH: 29
<212> TYPE: PRT
<213> ORGANISM: Artificial Sequence
<220> FEATURE:
<223> OTHER INFORMATION: peptide TP683
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (28)..(28)
<223> OTHER INFORMATION: Xaa is Lys(PEG2PEG2-gammaGlu-C18-OH)
<220> FEATURE:
<221> NAME/KEY: MISC_FEATURE
<222> LOCATION: (29)..(29)
<223> OTHER INFORMATION: Xaa is Thr conjugated to Lys-gammaGlu-NH2

<400> SEQUENCE: 81

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Leu Xaa Xaa
            20                  25

<210> SEQ ID NO 82
<211> LENGTH: 29
<212> TYPE: PRT
<213> ORGANISM: Artificial Sequence
<220> FEATURE:
<223> OTHER INFORMATION: peptide TP685
<220> FEATURE:
<221> NAME/KEY: MISC_FEATURE
<222> LOCATION: (2)..(2)
<223> OTHER INFORMATION: Xaa is D-serine
<220> FEATURE:
<221> NAME/KEY: MISC_FEATURE
<222> LOCATION: (10)..(10)
<223> OTHER INFORMATION: Xaa is p-aminomethyl-L-phenylalanine(gammaGlu-
      gammaGlu-C16)
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 82

His Xaa Gln Gly Thr Phe Thr Ser Asp Xaa Ser Lys Tyr Leu Asp Ala
1               5                   10                  15

Arg Ala Ala Gln Asp Phe Val Xaa Trp Leu Xaa Asp Thr
            20                  25

<210> SEQ ID NO 83
<211> LENGTH: 29
<212> TYPE: PRT
<213> ORGANISM: Artificial Sequence
<220> FEATURE:
<223> OTHER INFORMATION: peptide TP693
<220> FEATURE:
<221> NAME/KEY: MISC_FEATURE
```

```
<222> LOCATION: (2)..(2)
<223> OTHER INFORMATION: Xaa is D-serine
<220> FEATURE:
<221> NAME/KEY: MISC_FEATURE
<222> LOCATION: (10)..(10)
<223> OTHER INFORMATION: Xaa is p-aminomethyl-L-phenylalanine(gammaGlu-
      gammaGlu-C16)
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 83

His Xaa Gln Gly Thr Phe Thr Ser Asp Xaa Ser Lys Tyr Leu Asp Ala
1               5                   10                  15

Arg Ala Ala Gln Asp Phe Val Xaa Trp Leu Xaa Asp Thr
            20                  25

<210> SEQ ID NO 84
<211> LENGTH: 29
<212> TYPE: PRT
<213> ORGANISM: Artificial Sequence
<220> FEATURE:
<223> OTHER INFORMATION: peptide TP699
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 84

His Xaa Gln Gly Thr Phe Thr Ser Glu Tyr Ser Lys Lys Leu Asp Ala
1               5                   10                  15

Arg Ala Ala Gln Asp Phe Val Xaa Trp Leu Xaa Asp Thr
            20                  25

<210> SEQ ID NO 85
<211> LENGTH: 29
<212> TYPE: PRT
<213> ORGANISM: Artificial Sequence
<220> FEATURE:
<223> OTHER INFORMATION: peptide TP700
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
```

```
<220> FEATURE:
<221> NAME/KEY: MISC_FEATURE
<222> LOCATION: (29)..(29)
<223> OTHER INFORMATION: Xaa is C-terminal amide

<400> SEQUENCE: 85

His Xaa Gln Gly Thr Phe Thr Ser Asp Tyr Ser Glu Tyr Leu Asp Lys
1               5                   10                  15

Arg Ala Ala Gln Asp Phe Val Xaa Trp Leu Xaa Asp Thr
            20                  25

<210> SEQ ID NO 86
<211> LENGTH: 29
<212> TYPE: PRT
<213> ORGANISM: Artificial Sequence
<220> FEATURE:
<223> OTHER INFORMATION: peptide TP701
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 86

His Xaa Gln Gly Thr Phe Thr Ser Asp Tyr Ser Lys Tyr Leu Asp Glu
1               5                   10                  15

Arg Ala Ala Lys Asp Phe Val Xaa Trp Leu Xaa Asp Thr
            20                  25

<210> SEQ ID NO 87
<211> LENGTH: 29
<212> TYPE: PRT
<213> ORGANISM: Artificial Sequence
<220> FEATURE:
<223> OTHER INFORMATION: peptide TP702
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 87

His Xaa Gln Gly Thr Phe Thr Ser Asp Tyr Ser Lys Tyr Leu Asp Ala
1               5                   10                  15

Arg Ala Ala Gln Glu Phe Val Xaa Trp Leu Xaa Asp Thr
            20                  25

<210> SEQ ID NO 88
```

```
<211> LENGTH: 29
<212> TYPE: PRT
<213> ORGANISM: Artificial Sequence
<220> FEATURE:
<223> OTHER INFORMATION: peptide TP703
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 88

His Xaa Gln Gly Thr Phe Thr Ser Glu Tyr Ser Lys Lys Leu Asp Ala
 1               5                  10                  15

Arg Ala Ala Xaa Asp Phe Val Gln Trp Leu Xaa Asp Thr
            20                  25

<210> SEQ ID NO 89
<211> LENGTH: 29
<212> TYPE: PRT
<213> ORGANISM: Artificial Sequence
<220> FEATURE:
<223> OTHER INFORMATION: peptide TP704
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 89

His Xaa Gln Gly Thr Phe Thr Ser Asp Tyr Ser Lys Tyr Leu Asp Ala
 1               5                  10                  15

Arg Ala Ala Xaa Glu Phe Val Gln Trp Leu Xaa Asp Thr
            20                  25

<210> SEQ ID NO 90
<211> LENGTH: 29
<212> TYPE: PRT
<213> ORGANISM: Artificial Sequence
<220> FEATURE:
<223> OTHER INFORMATION: peptide TP705
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
```

```
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 90

His Xaa Gln Gly Thr Phe Thr Ser Asp Tyr Ser Lys Tyr Leu Asp Ala
1               5                   10                  15

Arg Ala Ala Xaa Asp Phe Val Glu Trp Leu Xaa Lys Thr
            20                  25

<210> SEQ ID NO 91
<211> LENGTH: 29
<212> TYPE: PRT
<213> ORGANISM: Artificial Sequence
<220> FEATURE:
<223> OTHER INFORMATION: peptide TP712
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Nle(1,2,3-triazole-5- PEG2PEG2-gammaGlu-
      C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 91

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 92
<211> LENGTH: 28
<212> TYPE: PRT
<213> ORGANISM: Artificial Sequence
<220> FEATURE:
<223> OTHER INFORMATION: peptide TP713
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 92

His Xaa Gln Gly Thr Phe Thr Ser Asp Tyr Ser Lys Tyr Leu Asp Ala
```

```
1               5                   10                  15
Arg Ala Ala Xaa Glu Phe Val Gln Trp Leu Xaa Xaa
            20                  25

<210> SEQ ID NO 93
<211> LENGTH: 29
<212> TYPE: PRT
<213> ORGANISM: Artificial Sequence
<220> FEATURE:
<223> OTHER INFORMATION: peptide TP735
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is Thr-OH

<400> SEQUENCE: 93

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Xaa
            20                  25

<210> SEQ ID NO 94
<211> LENGTH: 29
<212> TYPE: PRT
<213> ORGANISM: Artificial Sequence
<220> FEATURE:
<223> OTHER INFORMATION: peptide TP736
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is Thr-OH

<400> SEQUENCE: 94

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Asp Xaa
            20                  25

<210> SEQ ID NO 95
<211> LENGTH: 29
<212> TYPE: PRT
<213> ORGANISM: Artificial Sequence
<220> FEATURE:
```

```
<223> OTHER INFORMATION: peptide TP737
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is Thr-OH

<400> SEQUENCE: 95

His Xaa Gln Gly Thr Phe Thr Ser Asp Tyr Ser Lys Tyr Leu Asp Xaa
 1               5                  10                  15

Arg Ala Ala Gln Asp Phe Val Xaa Trp Leu Xaa Asp Xaa
            20                  25

<210> SEQ ID NO 96
<211> LENGTH: 29
<212> TYPE: PRT
<213> ORGANISM: Artificial Sequence
<220> FEATURE:
<223> OTHER INFORMATION: peptide TP811
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 96

His Xaa Gln Gly Thr Phe Thr Ser Asp Tyr Ser Lys Tyr Leu Asp Xaa
 1               5                  10                  15

Arg Ala Ala Gln Asp Phe Val Xaa Trp Leu Xaa Asp Thr
            20                  25

<210> SEQ ID NO 97
<211> LENGTH: 29
<212> TYPE: PRT
<213> ORGANISM: Artificial Sequence
<220> FEATURE:
<223> OTHER INFORMATION: peptide TP812
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
```

-continued

```
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 97

His Xaa Gln Gly Thr Phe Thr Ser Asp Tyr Ser Lys Tyr Leu Asp Ala
1               5                   10                  15

Arg Ala Ala Xaa Glu Phe Val Gln Trp Leu Xaa Asp Thr
            20                  25

<210> SEQ ID NO 98
<211> LENGTH: 29
<212> TYPE: PRT
<213> ORGANISM: Artificial Sequence
<220> FEATURE:
<223> OTHER INFORMATION: peptide TP813
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 98

His Xaa Gln Gly Thr Phe Thr Ser Asp Tyr Ser Lys Tyr Leu Asp Ala
1               5                   10                  15

Arg Ala Ala Gln Glu Phe Val Xaa Trp Leu Xaa Asp Thr
            20                  25

<210> SEQ ID NO 99
<211> LENGTH: 29
<212> TYPE: PRT
<213> ORGANISM: Artificial Sequence
<220> FEATURE:
<223> OTHER INFORMATION: peptide TP814
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 99

His Xaa Gln Gly Thr Phe Thr Ser Asp Tyr Ser Lys Tyr Leu Asp Ala
1               5                   10                  15
```

```
Arg Ala Ala Xaa Asp Phe Val Gln Trp Leu Xaa Glu Thr
            20                  25

<210> SEQ ID NO 100
<211> LENGTH: 29
<212> TYPE: PRT
<213> ORGANISM: Artificial Sequence
<220> FEATURE:
<223> OTHER INFORMATION: peptide TP815
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 100

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Glu Thr
            20                  25

<210> SEQ ID NO 101
<211> LENGTH: 29
<212> TYPE: PRT
<213> ORGANISM: Artificial Sequence
<220> FEATURE:
<223> OTHER INFORMATION: peptide TP825
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 101

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Glu Thr
            20                  25

<210> SEQ ID NO 102
<211> LENGTH: 29
<212> TYPE: PRT
<213> ORGANISM: Artificial Sequence
<220> FEATURE:
<223> OTHER INFORMATION: peptide TP826
```

-continued

```
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is gammaGlu
<220> FEATURE:
<221> NAME/KEY: MISC_FEATURE
<222> LOCATION: (29)..(29)
<223> OTHER INFORMATION: Xaa is C-terminal amide

<400> SEQUENCE: 102

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 103
<211> LENGTH: 29
<212> TYPE: PRT
<213> ORGANISM: Artificial Sequence
<220> FEATURE:
<223> OTHER INFORMATION: peptide TP827
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is gammaGlu
<220> FEATURE:
<221> NAME/KEY: MISC_FEATURE
<222> LOCATION: (29)..(29)
<223> OTHER INFORMATION: Xaa is C-terminal amide

<400> SEQUENCE: 103

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 104
<211> LENGTH: 29
<212> TYPE: PRT
<213> ORGANISM: Artificial Sequence
<220> FEATURE:
<223> OTHER INFORMATION: peptide TP828
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
```

```
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C16-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is gammaGlu
<220> FEATURE:
<221> NAME/KEY: MISC_FEATURE
<222> LOCATION: (29)..(29)
<223> OTHER INFORMATION: Xaa is C-terminal amide

<400> SEQUENCE: 104

His Xaa Gln Gly Thr Phe Thr Ser Asp Tyr Ser Lys Tyr Leu Asp Xaa
 1               5                  10                  15

Arg Ala Ala Gln Asp Phe Val Xaa Trp Leu Xaa Xaa Thr
                20                  25

<210> SEQ ID NO 105
<211> LENGTH: 30
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid, D-Serine, or
      alpha-Methyl-L-Serine
<220> FEATURE:
<221> NAME/KEY: MISC_FEATURE
<222> LOCATION: (10)..(10)
<223> OTHER INFORMATION: Xaa is Lys or p-aminomethyl-L-phenylalanine
      conjugated to a fatty acid provided that the amino acid at
      position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or
      Glu
<220> FEATURE:
<221> NAME/KEY: MISC_FEATURE
<222> LOCATION: (20)..(20)
<223> OTHER INFORMATION: Xaa is Lys conjugated to a fatty diacid,
      p-aminomethyl-L-phenylalanine conjugated to a fatty diacid,
      norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or
      p-aminomethyl-L-phenylalanine conjugated to a fatty diacid, Asp,
      alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid,
      or p-aminomethyl-L-phenylalanine conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
      Lys, alpha-aminoisobutyric acid, Ala, Lys conjugated to a fatty
``` diacid or p-aminomethyl-L-phenylalanine conjugated to a fatty diacid
<220> FEATURE:
<221> NAME/KEY: MISC_FEATURE
<222> LOCATION: (29)..(29)
<223> OTHER INFORMATION: Tyr has a C-terminal amide when 30 is absent
<220> FEATURE:
<221> NAME/KEY: MISC_FEATURE
<222> LOCATION: (30)..(30)
<223> OTHER INFORMATION: Xaa is absent or Lys linked at the C-terminus to gamma-Glu when 27 is Leu or L-Met-sulphone and 28 is Ala, alpha-aminoisobutyric acid, alpha-Methyl-L-Aspartic acid, or
<220> FEATURE:
<221> NAME/KEY: MISC_FEATURE
<222> LOCATION: (30)..(30)
<223> OTHER INFORMATION: Lys conjugated to a fatty diacid, with the proviso that for each co-agonist peptide, only one of 10, 20, 21, 24, or 28 is conjugated to a fatty diacid
<220> FEATURE:
<221> NAME/KEY: MISC_FEATURE
<222> LOCATION: (30)..(30)
<223> OTHER INFORMATION: Xaa has a C-terminal amide when present

<400> SEQUENCE: 105

His Xaa Gln Gly Thr Phe Thr Ser Asp Xaa Ser Leu Tyr Leu Asp Xaa
1               5                   10                  15

Arg Ala Ala Xaa Xaa Phe Val Xaa Xaa Leu Xaa Xaa Thr Xaa
            20                  25                  30

<210> SEQ ID NO 106
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid, D-Serine, or alpha-Methyl-L-Serine
<220> FEATURE:
<221> NAME/KEY: MISC_FEATURE
<222> LOCATION: (10)..(10)
<223> OTHER INFORMATION: Xaa is Lys or p-aminomethyl-L-phenylalanine conjugated to a fatty acid provided that the amino acid at position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or Glu
<220> FEATURE:
<221> NAME/KEY: MISC_FEATURE
<222> LOCATION: (20)..(20)
<223> OTHER INFORMATION: Xaa is Lys conjugated to a fatty diacid, p-aminomethyl-L-phenylalanine conjugated to a fatty diacid, norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or p-aminomethyl-L-phenylalanine conjugated to a fatty diacid, Asp, alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid, or p-aminomethyl-L-phenylalanine conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine

```
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
      Lys, alpha-aminoisobutyric acid, Ala, Lys conjugated to a fatty
      diacid or p-aminomethyl-L-phenylalanine conjugated to a fatty
      diacid;
<220> FEATURE:
<221> NAME/KEY: MISC_FEATURE
<222> LOCATION: (28)..(28)
<223> OTHER INFORMATION: with the proviso that for each co-agonist
      peptide, only one of 10, 20, 21, 24, or 28 is conjugated to a
      fatty diacid
<220> FEATURE:
<221> NAME/KEY: MISC_FEATURE
<222> LOCATION: (29)..(29)
<223> OTHER INFORMATION: Xaa is C-terminal amide

<400> SEQUENCE: 106

His Xaa Gln Gly Thr Phe Thr Ser Asp Xaa Ser Leu Tyr Leu Asp Xaa
1               5                   10                  15

Arg Ala Ala Xaa Xaa Phe Val Xaa Xaa Leu Xaa Xaa Thr
            20                  25

<210> SEQ ID NO 107
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (10)..(10)
<223> OTHER INFORMATION: Xaa is Lys or p-aminomethyl-L-phenylalanine
      conjugated to a fatty acid provided that the amino acid at
      position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or
      Glu
<220> FEATURE:
<221> NAME/KEY: MISC_FEATURE
<222> LOCATION: (20)..(20)
<223> OTHER INFORMATION: Xaa is Lys conjugated to a fatty diacid,
      p-aminomethyl-L-phenylalanine conjugated to a fatty diacid,
      norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or
      p-aminomethyl-L-phenylalanine conjugated to a fatty diacid, Asp,
      alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid,
      or p-aminomethyl-L-phenylalanine conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
      Lys, alpha-aminoisobutyric acid, Ala, Lys conjugated to a fatty
      diacid or p-aminomethyl-L-phenylalanine conjugated to a fatty
```

```
                diacid
<220> FEATURE:
<221> NAME/KEY: MISC_FEATURE
<222> LOCATION: (29)..(29)
<223> OTHER INFORMATION: Xaa is C-terminal amide

<400> SEQUENCE: 107

His Xaa Gln Gly Thr Phe Thr Ser Asp Xaa Ser Leu Tyr Leu Asp Xaa
1               5                   10                  15

Arg Ala Ala Xaa Xaa Phe Val Xaa Xaa Leu Xaa Xaa Thr
            20                  25

<210> SEQ ID NO 108
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid, D-Serine, or
      alpha-Methyl-L-Serine
<220> FEATURE:
<221> NAME/KEY: MISC_FEATURE
<222> LOCATION: (7)..(7)
<223> OTHER INFORMATION: Xaa is Thr, Phe or Leu
<220> FEATURE:
<221> NAME/KEY: MISC_FEATURE
<222> LOCATION: (9)..(9)
<223> OTHER INFORMATION: Xaa is Asp or Glu
<220> FEATURE:
<221> NAME/KEY: MISC_FEATURE
<222> LOCATION: (10)..(10)
<223> OTHER INFORMATION: Xaa is Tyr, norleucine conjugated to a fatty
      acid, p-aminomethyl-L-phenylalanine conjugated to a fatty diacid,
      Lys conjugated to a fatty acid provided that the amino acid at
      position 20 or 24 is a Lys conjugated to a fatty diacid, or
<220> FEATURE:
<221> NAME/KEY: MISC_FEATURE
<222> LOCATION: (10)..(10)
<223> OTHER INFORMATION: p-aminomethyl-L-phenylalanine conjugated to a
      fatty acid provided that the amino acid at position 24 is a Lys
      conjugated to a fatty diacid
<220> FEATURE:
<221> NAME/KEY: MISC_FEATURE
<222> LOCATION: (12)..(12)
<223> OTHER INFORMATION: Xaa is Lys, or Glu
<220> FEATURE:
<221> NAME/KEY: MISC_FEATURE
<222> LOCATION: (13)..(13)
<223> OTHER INFORMATION: Xaa is Tyr, Leu, or Lys
<220> FEATURE:
<221> NAME/KEY: MISC_FEATURE
<222> LOCATION: (14)..(14)
<223> OTHER INFORMATION: Xaa is Leu, or Asp
<220> FEATURE:
<221> NAME/KEY: MISC_FEATURE
<222> LOCATION: (15)..(15)
<223> OTHER INFORMATION: Xaa is Asp, Glu, alpha-Methyl-L-Aspartic acid,
      or alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid, Ala, Glu,
      Ser, Arg, or Lys
<220> FEATURE:
<221> NAME/KEY: MISC_FEATURE
<222> LOCATION: (17)..(17)
<223> OTHER INFORMATION: Xaa is Arg, Lys, Leu, or Ala
<220> FEATURE:
<221> NAME/KEY: MISC_FEATURE
<222> LOCATION: (19)..(19)
<223> OTHER INFORMATION: Xaa is Ala, or Gln
<220> FEATURE:
<221> NAME/KEY: MISC_FEATURE
```

-continued

```
<222> LOCATION: (20)..(20)
<223> OTHER INFORMATION: Xaa is Gln, Lys, Lys conjugated to a fatty
      diacid, p-aminomethyl-L-phenylalanine conjugated to a fatty
      diacid, or norleucine conjugated to a fatty diacid
<220> FEATURE:
<221> NAME/KEY: MISC_FEATURE
<222> LOCATION: (21)..(21)
<223> OTHER INFORMATION: Xaa is Asp, Phe, Glu, alpha-Methyl-L-Aspartic
      acid, Lys conjugated to a fatty diacid, or p-aminomethyl-L-
      phenylalanine conjugated to a fatty diacid
<220> FEATURE:
<221> NAME/KEY: MISC_FEATURE
<222> LOCATION: (22)..(22)
<223> OTHER INFORMATION: Xaa is Phe, Val, or alpha-methyl-L-
      phenylalanine
<220> FEATURE:
<221> NAME/KEY: MISC_FEATURE
<222> LOCATION: (23)..(23)
<223> OTHER INFORMATION: Xaa is Val, or Gln
<220> FEATURE:
<221> NAME/KEY: MISC_FEATURE
<222> LOCATION: (24)..(24)
<223> OTHER INFORMATION: Xaa is Gln, Glu, Lys conjugated to a fatty
      diacid, or p-aminomethyl-L-phenylalanine  conjugated to a fatty
      diacid
<220> FEATURE:
<221> NAME/KEY: MISC_FEATURE
<222> LOCATION: (25)..(25)
<223> OTHER INFORMATION: Xaa is Trp, or alpha-methyl-L-tryptophan
<220> FEATURE:
<221> NAME/KEY: MISC_FEATURE
<222> LOCATION: (27)..(27)
<223> OTHER INFORMATION: Xaa is L-methionine sulphone, or Leu
<220> FEATURE:
<221> NAME/KEY: MISC_FEATURE
<222> LOCATION: (28)..(28)
<223> OTHER INFORMATION: Xaa is Asp, alpha-Methyl-L-Aspartic acid alpha-
      aminoisobutyric acid, Ala, Lys, Gln, Glu, gamma-glutamic acid, Lys
      conjugated to a fatty diacid, or p-aminomethyl-L-phenylalanine
      conjugated to a fatty diacid
<220> FEATURE:
<221> NAME/KEY: MISC_FEATURE
<222> LOCATION: (29)..(29)
<223> OTHER INFORMATION: Xaa is Thr-OH, Thr-NH2, or Thr(Lys-gamma-
      glutamic acid)NH2 with the proviso that for each co-agonist
      peptide, only one or two of 10, 20, 21, 24, or 28 is conjugated to
      a fatty diacid

<400> SEQUENCE: 108

His Xaa Gln Gly Thr Phe Xaa Ser Xaa Xaa Ser Xaa Xaa Xaa Xaa Xaa
1               5                   10                  15

Xaa Ala Xaa Xaa Xaa Xaa Xaa Xaa Xaa Leu Xaa Xaa Xaa
            20                  25

<210> SEQ ID NO 109
<211> LENGTH: 29
<212> TYPE: PRT
<213> ORGANISM: Artificial Sequence
<220> FEATURE:
<223> OTHER INFORMATION: peptide TP564
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C20-OH)
<220> FEATURE:
<221> NAME/KEY: MISC_FEATURE
<222> LOCATION: (27)..(27)
<223> OTHER INFORMATION: Xaa is Lys(PEG2PEG2-gammaGlu-C20-OH)
```

-continued

```
<220> FEATURE:
<221> NAME/KEY: MISC_FEATURE
<222> LOCATION: (29)..(29)
<223> OTHER INFORMATION: Xaa is C-terminal amide

<400> SEQUENCE: 109

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
            20                  25

<210> SEQ ID NO 110
<211> LENGTH: 29
<212> TYPE: PRT
<213> ORGANISM: Artificial Sequence
<220> FEATURE:
<223> OTHER INFORMATION: peptide TP575
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (24)..(24)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 110

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Asp Thr
            20                  25

<210> SEQ ID NO 111
<211> LENGTH: 29
<212> TYPE: PRT
<213> ORGANISM: Artificial Sequence
<220> FEATURE:
<223> OTHER INFORMATION: peptide TP597
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 111

His Xaa Gln Gly Thr Phe Thr Ser Asp Tyr Ser Lys Leu Leu Asp Ala
1               5                   10                  15

Arg Ala Ala Xaa Asp Phe Val Gln Trp Leu Xaa Asp Thr
```

20              25

<210> SEQ ID NO 112
<211> LENGTH: 29
<212> TYPE: PRT
<213> ORGANISM: Artificial Sequence
<220> FEATURE:
<223> OTHER INFORMATION: peptide TP598
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 112

His Xaa Gln Gly Thr Phe Thr Ser Asp Tyr Ser Lys Tyr Leu Asp Ala
1               5                   10                  15

Lys Ala Ala Xaa Asp Phe Val Gln Trp Leu Xaa Asp Thr
            20                  25

<210> SEQ ID NO 113
<211> LENGTH: 29
<212> TYPE: PRT
<213> ORGANISM: Artificial Sequence
<220> FEATURE:
<223> OTHER INFORMATION: peptide TP604
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 113

His Xaa Gln Gly Thr Phe Thr Ser Asp Tyr Ser Lys Tyr Leu Asp Ala
1               5                   10                  15

Arg Ala Ala Gln Asp Phe Val Gln Trp Leu Xaa Xaa Thr
            20                  25

<210> SEQ ID NO 114
<211> LENGTH: 29
<212> TYPE: PRT
<213> ORGANISM: Artificial Sequence
<220> FEATURE:
<223> OTHER INFORMATION: peptide TP443
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:

-continued

```
<221> NAME/KEY: MISC_FEATURE
<222> LOCATION: (21)..(21)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (29)..(29)
<223> OTHER INFORMATION: Xaa is C-terminal amide

<400> SEQUENCE: 114

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 115
<211> LENGTH: 29
<212> TYPE: PRT
<213> ORGANISM: Artificial Sequence
<220> FEATURE:
<223> OTHER INFORMATION: peptide TP608
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is Lys(PEG5-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 115

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 116
<211> LENGTH: 29
<212> TYPE: PRT
<213> ORGANISM: Artificial Sequence
<220> FEATURE:
<223> OTHER INFORMATION: peptide TP609
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (21)..(21)
<223> OTHER INFORMATION: Xaa is p-aminomethyl-L-phenylalanine(PEG2PEG2-
      gammaGlu-C18-OH)
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 116
```

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Xaa Thr
            20                  25

<210> SEQ ID NO 117
<211> LENGTH: 29
<212> TYPE: PRT
<213> ORGANISM: Artificial Sequence
<220> FEATURE:
<223> OTHER INFORMATION: peptide TP628
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 117

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 118
<211> LENGTH: 29
<212> TYPE: PRT
<213> ORGANISM: Artificial Sequence
<220> FEATURE:
<223> OTHER INFORMATION: peptide TP630
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C16-OH)
<220> FEATURE:
<221> NAME/KEY: MISC_FEATURE
<222> LOCATION: (25)..(25)
<223> OTHER INFORMATION: Xaa is alpha-methyl-L-tryptophan
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: Xaa is C-terminal amide

<400> SEQUENCE: 118

His Xaa Gln Gly Thr Phe Thr Ser Asp Tyr Ser Lys Tyr Leu Asp Ala
1               5                   10                  15

Arg Ala Ala Xaa Asp Phe Val Gln Xaa Leu Xaa Asp Thr
            20                  25

```
<210> SEQ ID NO 119
<211> LENGTH: 29
<212> TYPE: PRT
<213> ORGANISM: Artificial Sequence
<220> FEATURE:
<223> OTHER INFORMATION: peptide TP640
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (20)..(20)
<223> OTHER INFORMATION: Xaa is Lys(PEG2PEG2-gammaGlu-C18-OH)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: Xaa is C-terminal amide

<400> SEQUENCE: 119

His Xaa Gln Gly Thr Phe Thr Ser Asp Tyr Ser Lys Leu Leu Asp Ala
1               5                   10                  15

Arg Ala Ala Xaa Asp Phe Val Gln Trp Leu Xaa Xaa Thr
            20                  25

<210> SEQ ID NO 120
<211> LENGTH: 29
<212> TYPE: PRT
<213> ORGANISM: Artificial Sequence
<220> FEATURE:
<223> OTHER INFORMATION: peptide TP829
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is Nle(1,2,3-triazole-4-C15)
<220> FEATURE:
<221> NAME/KEY: MISC_FEATURE
<222> LOCATION: (29)..(29)
<223> OTHER INFORMATION: Xaa is C-terminal amide

<400> SEQUENCE: 120

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 121
<211> LENGTH: 29
<212> TYPE: PRT
<213> ORGANISM: Artificial Sequence
<220> FEATURE:
<223> OTHER INFORMATION: peptide TP830
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is Nle(1,2,3-triazole-4-gammaGlu-C16)
```

```
<220> FEATURE:
<221> NAME/KEY: MISC_FEATURE
<222> LOCATION: (29)..(29)
<223> OTHER INFORMATION: Xaa is C-terminal amide

<400> SEQUENCE: 121

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 122
<211> LENGTH: 29
<212> TYPE: PRT
<213> ORGANISM: Artificial Sequence
<220> FEATURE:
<223> OTHER INFORMATION: peptide TP831
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is Nle(1,2,3-triazole-4-C4-Lys-C16)
<220> FEATURE:
<221> NAME/KEY: MISC_FEATURE
<222> LOCATION: (29)..(29)
<223> OTHER INFORMATION: Xaa is C-terminal amide

<400> SEQUENCE: 122

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 123
<211> LENGTH: 30
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid, D-Ser, or
      alpha-Methyl-L-Serine
<220> FEATURE:
<221> NAME/KEY: MISC_FEATURE
<222> LOCATION: (9)..(9)
<223> OTHER INFORMATION: Xaa is Asp, or Glu
<220> FEATURE:
<221> NAME/KEY: MISC_FEATURE
<222> LOCATION: (10)..(10)
<223> OTHER INFORMATION: Xaa is Lys or p-aminomethyl-L-phenylalanine
      conjugated to a fatty acid provided that the amino acid at
      position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or
      Glu
<220> FEATURE:
<221> NAME/KEY: MISC_FEATURE
<222> LOCATION: (20)..(20)
<223> OTHER INFORMATION: Xaa is Lys conjugated to a fatty diacid,
      p-aminomethyl-L-phenylalanine conjugated to a fatty diacid,
      norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or
      p-aminomethyl-L-phenylalanine conjugated to a fatty diacid, Asp,
```

```
      alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid,
      or p-aminomethyl-L-phenylalanine conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
      Lys, alpha-aminoisobutyric acid, Ala, Lys conjugated to a fatty
      diacid or p-aminomethyl-L-phenylalanine conjugated to a fatty
      diacid
<220> FEATURE:
<221> NAME/KEY: MISC_FEATURE
<222> LOCATION: (29)..(29)
<223> OTHER INFORMATION: Try has a C-terminal amide when 30 is absent
<220> FEATURE:
<221> NAME/KEY: MISC_FEATURE
<222> LOCATION: (30)..(30)
<223> OTHER INFORMATION: Xaa is absent, or Lys linked at the C-terminus
      to gamma-Glu when 27 is Leu or L-Met-sulphone and 28 is Ala,
      alpha-aminoisobutyric acid, alpha-Methyl-L-Aspartic acid, or Lys
      conjugated to a fatty diacid;
<220> FEATURE:
<221> NAME/KEY: MISC_FEATURE
<222> LOCATION: (30)..(30)
<223> OTHER INFORMATION: with the proviso that for each co-agonist
      peptide, only one of 10, 20, 21, 24, or 28 is conjugated to a
      fatty diacid
<220> FEATURE:
<221> NAME/KEY: MISC_FEATURE
<222> LOCATION: (30)..(30)
<223> OTHER INFORMATION: Xaa has a C-terminal amide when present

<400> SEQUENCE: 123

His Xaa Gln Gly Thr Phe Thr Ser Xaa Xaa Ser Leu Tyr Leu Asp Xaa
1               5                   10                  15

Arg Ala Ala Xaa Xaa Phe Val Xaa Xaa Leu Xaa Xaa Thr Xaa
            20                  25                  30

<210> SEQ ID NO 124
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid, D-Serine, or
      alpha-Methyl-L-Serine
<220> FEATURE:
<221> NAME/KEY: MISC_FEATURE
<222> LOCATION: (9)..(9)
<223> OTHER INFORMATION: Xaa is Asp or Glu
<220> FEATURE:
<221> NAME/KEY: MISC_FEATURE
<222> LOCATION: (10)..(10)
<223> OTHER INFORMATION: Xaa is Lys or p-aminomethyl-L-phenylalanine
      conjugated to a fatty acid provided that the amino acid at
      position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or
      Glu
<220> FEATURE:
```

```
<221> NAME/KEY: MISC_FEATURE
<222> LOCATION: (20)..(20)
<223> OTHER INFORMATION: Xaa is Lys conjugated to a fatty diacid,
      p-aminomethyl-L-phenylalanine conjugated to a fatty diacid,
      norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or
      p-aminomethyl-L-phenylalanine conjugated to a fatty diacid, Asp,
      alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid,
      or p-aminomethyl-L-phenylalanine  conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
      Lys, alpha-aminoisobutyric acid, Ala, Lys conjugated to a fatty
      diacid or p-aminomethyl-L-phenylalanine conjugated to a fatty
      diacid; with the proviso that for each co-agonist peptide,
<220> FEATURE:
<221> NAME/KEY: MISC_FEATURE
<222> LOCATION: (28)..(28)
<223> OTHER INFORMATION: only one of 10, 20, 21, 24, or 28 is conjugated
      to a fatty diacid
<220> FEATURE:
<221> NAME/KEY: MISC_FEATURE
<222> LOCATION: (29)..(29)
<223> OTHER INFORMATION: Xaa is C-terminal amide

<400> SEQUENCE: 124

His Xaa Gln Gly Thr Phe Thr Ser Xaa Xaa Ser Leu Tyr Leu Asp Xaa
1               5                   10                  15

Arg Ala Ala Xaa Xaa Phe Val Xaa Xaa Leu Xaa Xaa Thr
            20                  25

<210> SEQ ID NO 125
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (9)..(9)
<223> OTHER INFORMATION: Xaa is Asp, or Glu
<220> FEATURE:
<221> NAME/KEY: MISC_FEATURE
<222> LOCATION: (10)..(10)
<223> OTHER INFORMATION: Xaa is Lys or p-aminomethyl-L-phenylalanine
      conjugated to a fatty acid provided that the amino acid at
      position 20 or 24 is a Lys conjugated to a fatty diacid or Tyr
<220> FEATURE:
<221> NAME/KEY: MISC_FEATURE
<222> LOCATION: (16)..(16)
<223> OTHER INFORMATION: Xaa is alpha-aminoisobutyric acid, Ala, Ser, or
      Glu
<220> FEATURE:
<221> NAME/KEY: MISC_FEATURE
<222> LOCATION: (20)..(20)
<223> OTHER INFORMATION: Xaa is Lys conjugated to a fatty diacid,
```

```
        p-aminomethyl-L-phenylalanine conjugated to a fatty diacid,
        norleucine conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or
        p-aminomethyl-L-phenylalanine conjugated to a fatty diacid, Asp,
        alpha-methyl-L-phenylalanine, or alpha-Methyl-L-Aspartic acid
<220> FEATURE:
<221> NAME/KEY: MISC_FEATURE
<222> LOCATION: (24)..(24)
<223> OTHER INFORMATION: Xaa is Gln, Lys conjugated to a fatty diacid,
        or p-aminomethyl-L-phenylalanine conjugated to a fatty diacid
<220> FEATURE:
<221> NAME/KEY: MISC_FEATURE
<222> LOCATION: (25)..(25)
<223> OTHER INFORMATION: Xaa is Trp or alpha-methyl-L-tryptophan
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Glu, Asp, alpha-Methyl-L-Aspartic acid,
        Lys, alpha-aminoisobutyric acid, or Ala, Lys conjugated to a fatty
        diacid or p-aminomethyl-L-phenylalanine conjugated to a fatty
        diacid
<220> FEATURE:
<221> NAME/KEY: MISC_FEATURE
<222> LOCATION: (29)..(29)
<223> OTHER INFORMATION: Xaa is C-terminal amide

<400> SEQUENCE: 125

His Xaa Gln Gly Thr Phe Thr Ser Xaa Xaa Ser Leu Tyr Leu Asp Xaa
1               5                   10                  15

Arg Ala Ala Xaa Xaa Phe Val Xaa Xaa Leu Xaa Xaa Thr
            20                  25

<210> SEQ ID NO 126
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is Lys conjugated to N3
<220> FEATURE:
<221> NAME/KEY: MISC_FEATURE
<222> LOCATION: (29)..(29)
<223> OTHER INFORMATION: Xaa is C-terminal amide

<400> SEQUENCE: 126

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 127
<211> LENGTH: 28
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
```

```
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is Lys conjugated to N3

<400> SEQUENCE: 127

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp
            20                  25
```